US012751930B2

(12) United States Patent
Morris et al.

(10) Patent No.: US 12,751,930 B2
(45) Date of Patent: Oct. 6, 2026

(54) CELL-RECEPTOR TARGETED EXOSOMES

(71) Applicant: City of Hope, Duarte, CA (US)

(72) Inventors: Kevin Morris, Duarte, CA (US); Tristan Scott, Duarte, CA (US)

(73) Assignee: City of Hope, Duarte, CA (US)

( * ) Notice: Subject to any disclaimer, the term of this patent is extended or adjusted under 35 U.S.C. 154(b) by 884 days.

(21) Appl. No.: 17/912,450

(22) PCT Filed: Apr. 12, 2021

(86) PCT No.: PCT/US2021/026892
§ 371 (c)(1),
(2) Date: Sep. 16, 2022

(87) PCT Pub. No.: WO2021/211460
PCT Pub. Date: Oct. 21, 2021

(65) Prior Publication Data

US 2023/0149319 A1 May 18, 2023

Related U.S. Application Data

(60) Provisional application No. 63/009,309, filed on Apr. 13, 2020.

(51) Int. Cl.

| | |
|---|---|
| ***A61K 9/51*** | (2006.01) |
| ***C07K 16/114*** | (2026.01) |
| *A61K 9/00* | (2006.01) |

(52) U.S. Cl.
CPC ........ *A61K 9/5184* (2013.01); *C07K 16/1145* (2026.01); *A61K 9/0019* (2013.01); *A61K 9/0043* (2013.01); *C07K 2317/622* (2013.01)

(58) Field of Classification Search
None
See application file for complete search history.

(56) References Cited

U.S. PATENT DOCUMENTS

| | | | | |
|---|---|---|---|---|
| 2018/0298083 A1 | 10/2018 | Connors et al. | | |
| 2020/0109183 A1* | 4/2020 | Wiklander | .............. | A61P 29/00 |

FOREIGN PATENT DOCUMENTS

| | | |
|---|---|---|
| WO | WO-2010/119256 A1 | 10/2010 |
| WO | WO-2013/084000 A2 | 6/2013 |
| WO | WO-2013/084000 A3 | 6/2013 |
| WO | WO-2015/002956 A1 | 1/2015 |
| WO | WO-2016/172598 A1 | 10/2016 |

OTHER PUBLICATIONS

Huang et al., Immunity 45: 1108-1121 (2016).*

Gobbo, J. et al. (Nov. 22, 2015). "Restoring Anticancer Immune Response by Targeting Tumor-Derived Exosomes With a HSP70 Peptide Aptamer," *J Natl Cancer Inst* 108(3).

(Continued)

*Primary Examiner* — Erin M. Bowers

(57) ABSTRACT

Provided herein are, inter alia, recombinant fusion proteins and exosomes comprising recombinant fusion proteins; wherein the recombinant fusion proteins comprises exosome membrane-associated proteins and exogenous target proteins; pharmaceutical compositions; and methods of using the recombinant fusion proteins, exosomes, and pharmaceutical compositions to treat diseases such as cancer, HIV, and COVID-19.

18 Claims, 9 Drawing Sheets

Specification includes a Sequence Listing.

(56) References Cited

OTHER PUBLICATIONS

International Search Report mailed on Sep. 22, 2021 for PCT Application No. PCT/US2021/026892, filed Apr. 12, 2021, 5 pages.
Kojima, R. et al. (Apr. 3, 2018). "Designer exosomes produced by implanted cells intracerebrally deliver therapeutic cargo for Parkinson's disease treatment," *Nat Commun* 9(1):1305.
Walker, L.M. et al. (Sep. 22, 2011). "Broad neutralization coverage of HIV by multiple highly potent antibodies," *Nature* 477(7365):466-470.
Written Opinion mailed on Sep. 22, 2021 for PCT Application No. PCT/US2021/026892, filed Apr. 12, 2021, 5 pages.
Zhou, P. et al. (Jun. 13, 2019). "Broadly resistant HIV-1 against CD4-binding site neutralizing antibodies," *PLoS Pathogens* 15(6):e1007819.
Zou, X. et al. (Jul. 29, 2019). "Extracellular vesicles expressing a single-chain variable fragment of an HIV-1 specific antibody selectively target Env+ tissues," *Theranostics* 9(19):5657-5671.

* cited by examiner

SEQUENCE LISTING

```
<160> NUMBER OF SEQ ID NOS: 37

<210> SEQ ID NO 1
<211> LENGTH: 508
<212> TYPE: PRT
<213> ORGANISM: Artificial sequence
<220> FEATURE:
<223> OTHER INFORMATION: Synthetic polypeptide
```

<400> SEQUENCE: 1

Met Ala Val Glu Gly Gly Met Lys Cys Val Lys Phe Leu Leu Tyr Val
1 5 10 15

Leu Leu Leu Ala Phe Cys Ala Cys Ala Val Gly Leu Ile Ala Val Gly
20 25 30

Val Gly Ala Gln Leu Val Leu Gly Gly Gly Ser Gly Gly Gly Ser Gly
35 40 45

Gly Gly Ser Gly Gly Gly Ser Arg Ala His Leu Val Gln Ser Gly Thr
50 55 60

Ala Met Lys Lys Pro Gly Ala Ser Val Arg Val Ser Cys Gln Thr Ser
65 70 75 80

Gly Tyr Thr Phe Thr Ala His Ile Leu Phe Trp Phe Arg Gln Ala Pro
85 90 95

Gly Arg Gly Leu Glu Trp Val Gly Trp Ile Lys Pro Gln Tyr Gly Ala
100 105 110

Val Asn Phe Gly Gly Gly Phe Arg Asp Arg Val Thr Leu Thr Arg Asp
115 120 125

Val Tyr Arg Glu Ile Ala Tyr Met Asp Ile Arg Gly Leu Lys Pro Asp
130 135 140

Asp Thr Ala Val Tyr Tyr Cys Ala Arg Asp Arg Ser Tyr Gly Asp Ser
145 150 155 160

Ser Trp Ala Leu Asp Ala Trp Gly Gln Gly Thr Thr Val Val Val Ser
165 170 175

Ala Gly Gly Gly Ser Gly Gly Gly Ser Gly Gly Gly Ser Gly Gly Gly
180 185 190

Ser Tyr Ile His Val Thr Gln Ser Pro Ser Ser Leu Ser Val Ser Ile
195 200 205

Gly Asp Arg Val Thr Ile Asn Cys Gln Thr Ser Gln Gly Val Gly Ser
210 215 220

Asp Leu His Trp Tyr Gln His Lys Pro Gly Arg Ala Pro Lys Leu Leu
225 230 235 240

Ile His His Thr Ser Ser Val Glu Asp Gly Val Pro Ser Arg Phe Ser
245 250 255

Gly Ser Gly Phe His Thr Ser Phe Asn Leu Thr Ile Ser Asp Leu Gln
260 265 270

Ala Asp Asp Ile Ala Thr Tyr Tyr Cys Gln Val Leu Gln Phe Phe Gly
275 280 285

Arg Gly Ser Arg Leu His Ile Lys Gly Gly Gly Ser Gly Gly Gly Ser
290 295 300

Gly Gly Gly Ser Gly Gly Gly Ser Ile Ile Gln Gly Ala Thr Pro Gly
305 310 315 320

Ser Leu Leu Pro Val Val Ile Ile Ala Val Gly Val Phe Leu Phe Leu
325 330 335

Val Ala Phe Val Gly Cys Cys Gly Ala Cys Lys Glu Asn Tyr Cys Leu
340 345 350

Met Ile Thr Phe Ala Ile Phe Leu Ser Leu Ile Met Leu Val Glu Val
355 360 365

Ala Ala Ala Ile Ala Gly Tyr Val Phe Arg Asp Lys Val Met Ser Glu
370 375 380

Phe Asn Asn Asn Phe Arg Gln Gln Met Glu Asn Tyr Pro Lys Asn Asn
385 390 395 400

His Thr Ala Ser Ile Leu Asp Arg Met Gln Ala Asp Phe Lys Cys Cys

-continued

```
                405                 410                 415

Gly Ala Ala Asn Tyr Thr Asp Trp Glu Lys Ile Pro Ser Met Ser Lys
            420                 425                 430

Asn Arg Val Pro Asp Ser Cys Cys Ile Asn Val Thr Val Gly Cys Gly
        435                 440                 445

Ile Asn Phe Asn Glu Lys Ala Ile His Lys Glu Gly Cys Val Glu Lys
    450                 455                 460

Ile Gly Gly Trp Leu Arg Lys Asn Val Leu Val Val Ala Ala Ala Ala
465                 470                 475                 480

Leu Gly Ile Ala Phe Val Glu Val Leu Gly Ile Val Phe Ala Cys Cys
                485                 490                 495

Leu Val Lys Ser Ile Arg Ser Gly Tyr Glu Val Met
            500                 505


<210> SEQ ID NO 2
<211> LENGTH: 469
<212> TYPE: PRT
<213> ORGANISM: Artificial sequence
<220> FEATURE:
<223> OTHER INFORMATION: Synthetic polypeptide

<400> SEQUENCE: 2

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Gly Gly Gly Ser Gly Gly Gly Ser Gly Gly Gly Ser Gly
145                 150                 155                 160

Gly Gly Ser Arg Ala His Leu Val Gln Ser Gly Thr Ala Met Lys Lys
                165                 170                 175

Pro Gly Ala Ser Val Arg Val Ser Cys Gln Thr Ser Gly Tyr Thr Phe
            180                 185                 190

Thr Ala His Ile Leu Phe Trp Phe Arg Gln Ala Pro Gly Arg Gly Leu
        195                 200                 205

Glu Trp Val Gly Trp Ile Lys Pro Gln Tyr Gly Ala Val Asn Phe Gly
    210                 215                 220

Gly Gly Phe Arg Asp Arg Val Thr Leu Thr Arg Asp Val Tyr Arg Glu
225                 230                 235                 240

Ile Ala Tyr Met Asp Ile Arg Gly Leu Lys Pro Asp Asp Thr Ala Val
                245                 250                 255

Tyr Tyr Cys Ala Arg Asp Arg Ser Tyr Gly Asp Ser Ser Trp Ala Leu
```

```
            260                 265                 270

Asp Ala Trp Gly Gln Gly Thr Thr Val Val Val Ser Ala Gly Gly Gly
        275                 280                 285

Ser Gly Gly Gly Ser Gly Gly Gly Ser Gly Gly Gly Ser Tyr Ile His
    290                 295                 300

Val Thr Gln Ser Pro Ser Ser Leu Ser Val Ser Ile Gly Asp Arg Val
305                 310                 315                 320

Thr Ile Asn Cys Gln Thr Ser Gln Gly Val Gly Ser Asp Leu His Trp
                325                 330                 335

Tyr Gln His Lys Pro Gly Arg Ala Pro Lys Leu Leu Ile His His Thr
            340                 345                 350

Ser Ser Val Glu Asp Gly Val Pro Ser Arg Phe Ser Gly Ser Gly Phe
        355                 360                 365

His Thr Ser Phe Asn Leu Thr Ile Ser Asp Leu Gln Ala Asp Asp Ile
    370                 375                 380

Ala Thr Tyr Tyr Cys Gln Val Leu Gln Phe Phe Gly Arg Gly Ser Arg
385                 390                 395                 400

Leu His Ile Lys Gly Gly Gly Ser Gly Gly Gly Ser Gly Gly Gly Ser
                405                 410                 415

Gly Gly Gly Ser Gly Cys Val Glu Lys Ile Gly Gly Trp Leu Arg Lys
            420                 425                 430

Asn Val Leu Val Val Ala Ala Ala Ala Leu Gly Ile Ala Phe Val Glu
        435                 440                 445

Val Leu Gly Ile Val Phe Ala Cys Cys Leu Val Lys Ser Ile Arg Ser
    450                 455                 460

Gly Tyr Glu Val Met
465


<210> SEQ ID NO 3
<211> LENGTH: 490
<212> TYPE: PRT
<213> ORGANISM: Artificial sequence
<220> FEATURE:
<223> OTHER INFORMATION: Synthetic polypeptide

<400> SEQUENCE: 3

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Gly Gly Gly Ser Gly Gly Gly Ser Gly Gly Gly Ser Gly
```

-continued

```
145                 150                 155                 160

Gly Gly Ser Arg Ala His Leu Val Gln Ser Gly Thr Ala Met Lys Lys
                165                 170                 175

Pro Gly Ala Ser Val Arg Val Ser Cys Gln Thr Ser Gly Tyr Thr Phe
            180                 185                 190

Thr Ala His Ile Leu Phe Trp Phe Arg Gln Ala Pro Gly Arg Gly Leu
        195                 200                 205

Glu Trp Val Gly Trp Ile Lys Pro Gln Tyr Gly Ala Val Asn Phe Gly
    210                 215                 220

Gly Gly Phe Arg Asp Arg Val Thr Leu Thr Arg Asp Val Tyr Arg Glu
225                 230                 235                 240

Ile Ala Tyr Met Asp Ile Arg Gly Leu Lys Pro Asp Asp Thr Ala Val
                245                 250                 255

Tyr Tyr Cys Ala Arg Asp Arg Ser Tyr Gly Asp Ser Ser Trp Ala Leu
            260                 265                 270

Asp Ala Trp Gly Gln Gly Thr Thr Val Val Val Ser Ala Gly Gly Gly
        275                 280                 285

Ser Gly Gly Gly Ser Gly Gly Gly Ser Gly Gly Gly Ser Tyr Ile His
    290                 295                 300

Val Thr Gln Ser Pro Ser Ser Leu Ser Val Ser Ile Gly Asp Arg Val
305                 310                 315                 320

Thr Ile Asn Cys Gln Thr Ser Gln Gly Val Gly Ser Asp Leu His Trp
                325                 330                 335

Tyr Gln His Lys Pro Gly Arg Ala Pro Lys Leu Leu Ile His His Thr
            340                 345                 350

Ser Ser Val Glu Asp Gly Val Pro Ser Arg Phe Ser Gly Ser Gly Phe
        355                 360                 365

His Thr Ser Phe Asn Leu Thr Ile Ser Asp Leu Gln Ala Asp Asp Ile
    370                 375                 380

Ala Thr Tyr Tyr Cys Gln Val Leu Gln Phe Phe Gly Arg Gly Ser Arg
385                 390                 395                 400

Leu His Ile Lys Gly Gly Gly Ser Gly Gly Gly Ser Gly Gly Gly Ser
                405                 410                 415

Gly Gly Gly Ser Cys Cys Ile Asn Val Thr Val Gly Cys Gly Ile Asn
            420                 425                 430

Phe Asn Glu Lys Ala Ile His Lys Glu Gly Cys Val Glu Lys Ile Gly
        435                 440                 445

Gly Trp Leu Arg Lys Asn Val Leu Val Val Ala Ala Ala Ala Leu Gly
    450                 455                 460

Ile Ala Phe Val Glu Val Leu Gly Ile Val Phe Ala Cys Cys Leu Val
465                 470                 475                 480

Lys Ser Ile Arg Ser Gly Tyr Glu Val Met
                485                 490


<210> SEQ ID NO 4
<211> LENGTH: 492
<212> TYPE: PRT
<213> ORGANISM: Artificial sequence
<220> FEATURE:
<223> OTHER INFORMATION: Synthetic polypeptide

<400> SEQUENCE: 4

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
```

-continued

```
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Gly Gly Gly Ser Gly Gly
                165                 170                 175

Gly Ser Gly Gly Gly Ser Gly Gly Gly Ser Arg Ala His Leu Val Gln
            180                 185                 190

Ser Gly Thr Ala Met Lys Lys Pro Gly Ala Ser Val Arg Val Ser Cys
        195                 200                 205

Gln Thr Ser Gly Tyr Thr Phe Thr Ala His Ile Leu Phe Trp Phe Arg
    210                 215                 220

Gln Ala Pro Gly Arg Gly Leu Glu Trp Val Gly Trp Ile Lys Pro Gln
225                 230                 235                 240

Tyr Gly Ala Val Asn Phe Gly Gly Gly Phe Arg Asp Arg Val Thr Leu
                245                 250                 255

Thr Arg Asp Val Tyr Arg Glu Ile Ala Tyr Met Asp Ile Arg Gly Leu
            260                 265                 270

Lys Pro Asp Asp Thr Ala Val Tyr Tyr Cys Ala Arg Asp Arg Ser Tyr
        275                 280                 285

Gly Asp Ser Ser Trp Ala Leu Asp Ala Trp Gly Gln Gly Thr Thr Val
    290                 295                 300

Val Val Ser Ala Gly Gly Gly Ser Gly Gly Gly Ser Gly Gly Gly Ser
305                 310                 315                 320

Gly Gly Gly Ser Tyr Ile His Val Thr Gln Ser Pro Ser Ser Leu Ser
                325                 330                 335

Val Ser Ile Gly Asp Arg Val Thr Ile Asn Cys Gln Thr Ser Gln Gly
            340                 345                 350

Val Gly Ser Asp Leu His Trp Tyr Gln His Lys Pro Gly Arg Ala Pro
        355                 360                 365

Lys Leu Leu Ile His His Thr Ser Ser Val Glu Asp Gly Val Pro Ser
    370                 375                 380

Arg Phe Ser Gly Ser Gly Phe His Thr Ser Phe Asn Leu Thr Ile Ser
385                 390                 395                 400

Asp Leu Gln Ala Asp Asp Ile Ala Thr Tyr Tyr Cys Gln Val Leu Gln
                405                 410                 415

Phe Phe Gly Arg Gly Ser Arg Leu His Ile Lys Gly Gly Gly Ser Gly
            420                 425                 430

Gly Gly Ser Gly Gly Gly Ser Gly Gly Gly Ser Gly Cys Val Glu Lys
        435                 440                 445
```

Ile Gly Gly Trp Leu Arg Lys Asn Val Leu Val Val Ala Ala Ala Ala
450 455 460

Leu Gly Ile Ala Phe Val Glu Val Leu Gly Ile Val Phe Ala Cys Cys
465 470 475 480

Leu Val Lys Ser Ile Arg Ser Gly Tyr Glu Val Met
485 490

<210> SEQ ID NO 5
<211> LENGTH: 483
<212> TYPE: PRT
<213> ORGANISM: Artificial sequence
<220> FEATURE:
<223> OTHER INFORMATION: Synthetic polypeptide

<400> SEQUENCE: 5

Met Val Arg Gly Val Pro Phe Arg His Leu Leu Leu Val Leu Gln Leu
1 5 10 15

Ala Leu Leu Pro Ala Ala Thr Gln Gly Lys Lys Val Val Leu Gly Lys
20 25 30

Lys Gly Asp Thr Val Glu Leu Thr Cys Thr Ala Ser Gln Lys Lys Ser
35 40 45

Ile Gln Phe His Trp Lys Asn Ser Asn Gln Ile Lys Ile Leu Gly Asn
50 55 60

Gln Gly Ser Phe Leu Thr Lys Gly Pro Ser Lys Leu Asn Asp Arg Ala
65 70 75 80

Asp Ser Arg Arg Ser Leu Trp Asp Gln Gly Asn Phe Pro Leu Ile Ile
85 90 95

Lys Asn Leu Lys Ile Glu Asp Ser Asp Thr Tyr Ile Cys Glu Val Glu
100 105 110

Asp Gln Lys Glu Glu Val Gln Leu Leu Val Phe Gly Leu Thr Ala Asn
115 120 125

Ser Asp Thr His Leu Leu Gln Gly Gln Ser Leu Thr Leu Thr Leu Glu
130 135 140

Ser Pro Pro Gly Ser Ser Pro Ser Val Gln Cys Arg Ser Pro Arg Gly
145 150 155 160

Lys Asn Ile Gln Gly Gly Lys Thr Leu Ser Val Ser Gln Leu Glu Leu
165 170 175

Gln Asp Ser Gly Thr Trp Thr Cys Thr Val Leu Gln Asn Gln Lys Lys
180 185 190

Val Glu Phe Lys Ile Asp Ile Val Val Leu Ala Phe Gln Lys Ala Ser
195 200 205

Gly Gly Gly Gly Ser Gly Gly Gly Gly Ser Met Ala Leu Ile Val Leu
210 215 220

Gly Gly Val Ala Gly Leu Leu Leu Phe Ile Gly Leu Gly Ile Phe Phe
225 230 235 240

Gly Gly Gly Gly Ser Met Ala Val Glu Gly Gly Met Lys Cys Val Lys
245 250 255

Phe Leu Leu Tyr Val Leu Leu Leu Ala Phe Cys Ala Cys Ala Val Gly
260 265 270

Leu Ile Ala Val Gly Val Gly Ala Gln Leu Val Leu Ser Gln Thr Ile
275 280 285

Ile Gln Gly Ala Thr Pro Gly Ser Leu Leu Pro Val Val Ile Ile Ala
290 295 300

Val Gly Val Phe Leu Phe Leu Val Ala Phe Val Gly Cys Cys Gly Ala
305 310 315 320

```
Cys Lys Glu Asn Tyr Cys Leu Met Ile Thr Phe Ala Ile Phe Leu Ser
                325                 330                 335

Leu Ile Met Leu Val Glu Val Ala Ala Ala Ile Ala Gly Tyr Val Phe
            340                 345                 350

Arg Asp Lys Val Met Ser Glu Phe Asn Asn Asn Phe Arg Gln Gln Met
        355                 360                 365

Glu Asn Tyr Pro Lys Asn Asn His Thr Ala Ser Ile Leu Asp Arg Met
    370                 375                 380

Gln Ala Asp Phe Lys Cys Cys Gly Ala Ala Asn Tyr Thr Asp Trp Glu
385                 390                 395                 400

Lys Ile Pro Ser Met Ser Lys Asn Arg Val Pro Asp Ser Cys Cys Ile
                405                 410                 415

Asn Val Thr Val Gly Cys Gly Ile Asn Phe Asn Glu Lys Ala Ile His
            420                 425                 430

Lys Glu Gly Cys Val Glu Lys Ile Gly Gly Trp Leu Arg Lys Asn Val
        435                 440                 445

Leu Val Val Ala Ala Ala Ala Leu Gly Ile Ala Phe Val Glu Val Leu
    450                 455                 460

Gly Ile Val Phe Ala Cys Cys Leu Val Lys Ser Ile Arg Ser Gly Tyr
465                 470                 475                 480

Glu Val Met


<210> SEQ ID NO 6
<211> LENGTH: 681
<212> TYPE: PRT
<213> ORGANISM: Artificial sequence
<220> FEATURE:
<223> OTHER INFORMATION: Synthetic polypeptide

<400> SEQUENCE: 6

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Gly Asn Ser Thr
            20                  25                  30

Met Gly Ser Gly Arg Ala His Leu Val Gln Ser Gly Thr Ala Met Lys
        35                  40                  45

Lys Pro Gly Ala Ser Val Arg Val Ser Cys Gln Thr Ser Gly Tyr Thr
    50                  55                  60

Phe Thr Ala His Ile Leu Phe Trp Phe Arg Gln Ala Pro Gly Arg Gly
65                  70                  75                  80

Leu Glu Trp Val Gly Trp Ile Lys Pro Gln Tyr Gly Ala Val Asn Phe
                85                  90                  95

Gly Gly Gly Phe Arg Asp Arg Val Thr Leu Thr Arg Asp Val Tyr Arg
            100                 105                 110

Glu Ile Ala Tyr Met Asp Ile Arg Gly Leu Lys Pro Asp Asp Thr Ala
        115                 120                 125

Val Tyr Tyr Cys Ala Arg Asp Arg Ser Tyr Gly Asp Ser Ser Trp Ala
    130                 135                 140

Leu Asp Ala Trp Gly Gln Gly Thr Thr Val Val Val Ser Ala Gly Gly
145                 150                 155                 160

Gly Ser Gly Gly Gly Ser Gly Gly Gly Ser Gly Gly Gly Ser Tyr Ile
                165                 170                 175

His Val Thr Gln Ser Pro Ser Ser Leu Ser Val Ser Ile Gly Asp Arg
            180                 185                 190
```

-continued

```
Val Thr Ile Asn Cys Gln Thr Ser Gln Gly Val Gly Ser Asp Leu His
        195                 200                 205

Trp Tyr Gln His Lys Pro Gly Arg Ala Pro Lys Leu Leu Ile His His
    210                 215                 220

Thr Ser Ser Val Glu Asp Gly Val Pro Ser Arg Phe Ser Gly Ser Gly
225                 230                 235                 240

Phe His Thr Ser Phe Asn Leu Thr Ile Ser Asp Leu Gln Ala Asp Asp
                245                 250                 255

Ile Ala Thr Tyr Tyr Cys Gln Val Leu Gln Phe Phe Gly Arg Gly Ser
            260                 265                 270

Arg Leu His Ile Lys Gly Ser Gly Ser Gly Ser Gly Gly Ser Ser Leu
        275                 280                 285

Glu Leu Asn Leu Thr Asp Ser Glu Asn Ala Thr Cys Leu Tyr Ala Lys
    290                 295                 300

Trp Gln Met Asn Phe Thr Val Arg Tyr Glu Thr Thr Asn Lys Thr Tyr
305                 310                 315                 320

Lys Thr Val Thr Ile Ser Asp His Gly Thr Val Thr Tyr Asn Gly Ser
                325                 330                 335

Ile Cys Gly Asp Asp Gln Asn Gly Pro Lys Ile Ala Val Gln Phe Gly
            340                 345                 350

Pro Gly Phe Ser Trp Ile Ala Asn Phe Thr Lys Ala Ala Ser Thr Tyr
        355                 360                 365

Ser Ile Asp Ser Val Ser Phe Ser Tyr Asn Thr Gly Asp Asn Thr Thr
    370                 375                 380

Phe Pro Asp Ala Glu Asp Lys Gly Ile Leu Thr Val Asp Glu Leu Leu
385                 390                 395                 400

Ala Ile Arg Ile Pro Leu Asn Asp Leu Phe Arg Cys Asn Ser Leu Ser
                405                 410                 415

Thr Leu Glu Lys Asn Asp Val Val Gln His Tyr Trp Asp Val Leu Val
            420                 425                 430

Gln Ala Phe Val Gln Asn Gly Thr Val Ser Thr Asn Glu Phe Leu Cys
        435                 440                 445

Asp Lys Asp Lys Thr Ser Thr Val Ala Pro Thr Ile His Thr Thr Val
    450                 455                 460

Pro Ser Pro Thr Thr Thr Pro Thr Pro Lys Glu Lys Pro Glu Ala Gly
465                 470                 475                 480

Thr Tyr Ser Val Asn Asn Gly Asn Asp Thr Cys Leu Leu Ala Thr Met
                485                 490                 495

Gly Leu Gln Leu Asn Ile Thr Gln Asp Lys Val Ala Ser Val Ile Asn
            500                 505                 510

Ile Asn Pro Asn Thr Thr His Ser Thr Gly Ser Cys Arg Ser His Thr
        515                 520                 525

Ala Leu Leu Arg Leu Asn Ser Ser Thr Ile Lys Tyr Leu Asp Phe Val
    530                 535                 540

Phe Ala Val Lys Asn Glu Asn Arg Phe Tyr Leu Lys Glu Val Asn Ile
545                 550                 555                 560

Ser Met Tyr Leu Val Asn Gly Ser Val Phe Ser Ile Ala Asn Asn Asn
                565                 570                 575

Leu Ser Tyr Trp Asp Ala Pro Leu Gly Ser Ser Tyr Met Cys Asn Lys
            580                 585                 590

Glu Gln Thr Val Ser Val Ser Gly Ala Phe Gln Ile Asn Thr Phe Asp
        595                 600                 605

Leu Arg Val Gln Pro Phe Asn Val Thr Gln Gly Lys Tyr Ser Thr Ala
```

```
    610                 615                 620

Gln Glu Cys Ser Leu Asp Asp Asp Thr Ile Leu Ile Pro Ile Ile Val
625                 630                 635                 640

Gly Ala Gly Leu Ser Gly Leu Ile Ile Val Ile Val Ile Ala Tyr Val
                645                 650                 655

Ile Gly Arg Arg Lys Ser Tyr Ala Gly Tyr Gln Thr Leu Gly Ser Gly
            660                 665                 670

Tyr Pro Tyr Asp Val Pro Asp Tyr Ala
        675                 680


<210> SEQ ID NO 7
<211> LENGTH: 555
<212> TYPE: PRT
<213> ORGANISM: Artificial sequence
<220> FEATURE:
<223> OTHER INFORMATION: Synthetic polypeptide

<400> SEQUENCE: 7

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Gly Asn Ser Thr
            20                  25                  30

Met Gly Ser Gly Arg Ala His Leu Val Gln Ser Gly Thr Ala Met Lys
        35                  40                  45

Lys Pro Gly Ala Ser Val Arg Val Ser Cys Gln Thr Ser Gly Tyr Thr
    50                  55                  60

Phe Thr Ala His Ile Leu Phe Trp Phe Arg Gln Ala Pro Gly Arg Gly
65                  70                  75                  80

Leu Glu Trp Val Gly Trp Ile Lys Pro Gln Tyr Gly Ala Val Asn Phe
                85                  90                  95

Gly Gly Gly Phe Arg Asp Arg Val Thr Leu Thr Arg Asp Val Tyr Arg
            100                 105                 110

Glu Ile Ala Tyr Met Asp Ile Arg Gly Leu Lys Pro Asp Asp Thr Ala
        115                 120                 125

Val Tyr Tyr Cys Ala Arg Asp Arg Ser Tyr Gly Asp Ser Ser Trp Ala
    130                 135                 140

Leu Asp Ala Trp Gly Gln Gly Thr Thr Val Val Val Ser Ala Gly Gly
145                 150                 155                 160

Gly Ser Gly Gly Gly Ser Gly Gly Gly Ser Gly Gly Gly Ser Tyr Ile
                165                 170                 175

His Val Thr Gln Ser Pro Ser Ser Leu Ser Val Ser Ile Gly Asp Arg
            180                 185                 190

Val Thr Ile Asn Cys Gln Thr Ser Gln Gly Val Gly Ser Asp Leu His
        195                 200                 205

Trp Tyr Gln His Lys Pro Gly Arg Ala Pro Lys Leu Leu Ile His His
    210                 215                 220

Thr Ser Ser Val Glu Asp Gly Val Pro Ser Arg Phe Ser Gly Ser Gly
225                 230                 235                 240

Phe His Thr Ser Phe Asn Leu Thr Ile Ser Asp Leu Gln Ala Asp Asp
                245                 250                 255

Ile Ala Thr Tyr Tyr Cys Gln Val Leu Gln Phe Phe Gly Arg Gly Ser
            260                 265                 270

Arg Leu His Ile Lys Glu Ser Lys Tyr Gly Pro Pro Cys Pro Pro Cys
        275                 280                 285

Pro Ala Pro Glu Phe Glu Gly Gly Pro Ser Val Phe Leu Phe Pro Pro
```

```
    290                 295                 300

Lys Pro Lys Asp Thr Leu Met Ile Ser Arg Thr Pro Glu Val Thr Cys
305                 310                 315                 320

Val Val Val Asp Val Ser Gln Glu Asp Pro Glu Val Gln Phe Asn Trp
                325                 330                 335

Tyr Val Asp Gly Val Glu Val His Asn Ala Lys Thr Lys Pro Arg Glu
            340                 345                 350

Glu Gln Phe Gln Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
    370                 375                 380

Lys Gly Leu Pro Ser Ser Ile Glu Lys Thr Ile Ser Lys Ala Lys Gly
385                 390                 395                 400

Gln Pro Arg Glu Pro Gln Val Tyr Thr Leu Pro Pro Ser Gln Glu Glu
                405                 410                 415

Met Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
    450                 455                 460

Leu Tyr Ser Arg Leu Thr Val Asp Lys Ser Arg Trp Gln Glu Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Leu Gly Lys Thr Ile Leu Ile Pro Ile
            500                 505                 510

Ile Val Gly Ala Gly Leu Ser Gly Leu Ile Ile Val Ile Val Ile Ala
        515                 520                 525

Tyr Val Ile Gly Arg Arg Lys Ser Tyr Ala Gly Tyr Gln Thr Leu Gly
    530                 535                 540

Ser Gly Tyr Pro Tyr Asp Val Pro Asp Tyr Ala
545                 550                 555


<210> SEQ ID NO 8
<211> LENGTH: 1138
<212> TYPE: PRT
<213> ORGANISM: Artificial sequence
<220> FEATURE:
<223> OTHER INFORMATION: Synthetic polypeptide

<400> SEQUENCE: 8

Met Gly Arg Leu Ala Ser Arg Pro Leu Leu Leu Ala Leu Leu Ser Leu
1               5                   10                  15

Ala Leu Cys Arg Gly Arg Val Val Arg Gly Ser Gly Arg Ala His Leu
            20                  25                  30

Val Gln Ser Gly Thr Ala Met Lys Lys Pro Gly Ala Ser Val Arg Val
        35                  40                  45

Ser Cys Gln Thr Ser Gly Tyr Thr Phe Thr Ala His Ile Leu Phe Trp
    50                  55                  60

Phe Arg Gln Ala Pro Gly Arg Gly Leu Glu Trp Val Gly Trp Ile Lys
65                  70                  75                  80

Pro Gln Tyr Gly Ala Val Asn Phe Gly Gly Gly Phe Arg Asp Arg Val
                85                  90                  95

Thr Leu Thr Arg Asp Val Tyr Arg Glu Ile Ala Tyr Met Asp Ile Arg
```

-continued

```
            100                 105                 110

Gly Leu Lys Pro Asp Asp Thr Ala Val Tyr Tyr Cys Ala Arg Asp Arg
        115                 120                 125

Ser Tyr Gly Asp Ser Ser Trp Ala Leu Asp Ala Trp Gly Gln Gly Thr
    130                 135                 140

Thr Val Val Val Ser Ala Gly Ser Asp Ser Asn Ala Gly His Ala Ser
145                 150                 155                 160

Ala Gly Asn Thr Ser Tyr Ile His Val Thr Gln Ser Pro Ser Ser Leu
                165                 170                 175

Ser Val Ser Ile Gly Asp Arg Val Thr Ile Asn Cys Gln Thr Ser Gln
            180                 185                 190

Gly Val Gly Ser Asp Leu His Trp Tyr Gln His Lys Pro Gly Arg Ala
        195                 200                 205

Pro Lys Leu Leu Ile His His Thr Ser Ser Val Glu Asp Gly Val Pro
    210                 215                 220

Ser Arg Phe Ser Gly Ser Gly Phe His Thr Ser Phe Asn Leu Thr Ile
225                 230                 235                 240

Ser Asp Leu Gln Ala Asp Asp Ile Ala Thr Tyr Tyr Cys Gln Val Leu
                245                 250                 255

Gln Phe Phe Gly Arg Gly Ser Arg Leu His Ile Lys Gly Ser Gly Ser
            260                 265                 270

Gly Ser Gly Val Pro Thr Ala Thr Leu Val Arg Val Val Gly Thr Glu
        275                 280                 285

Leu Val Ile Pro Cys Asn Val Ser Asp Tyr Asp Gly Pro Ser Glu Gln
    290                 295                 300

Asn Phe Asp Trp Ser Phe Ser Ser Leu Gly Ser Ser Phe Val Glu Leu
305                 310                 315                 320

Ala Ser Thr Trp Glu Val Gly Phe Pro Ala Gln Leu Tyr Gln Glu Arg
                325                 330                 335

Leu Gln Arg Gly Glu Ile Leu Leu Arg Arg Thr Ala Asn Asp Ala Val
            340                 345                 350

Glu Leu His Ile Lys Asn Val Gln Pro Ser Asp Gln Gly His Tyr Lys
        355                 360                 365

Cys Ser Thr Pro Ser Thr Asp Ala Thr Val Gln Gly Asn Tyr Glu Asp
    370                 375                 380

Thr Val Gln Val Lys Val Leu Ala Asp Ser Leu His Val Gly Pro Ser
385                 390                 395                 400

Ala Arg Pro Pro Pro Ser Leu Ser Leu Arg Glu Gly Glu Pro Phe Glu
                405                 410                 415

Leu Arg Cys Thr Ala Ala Ser Ala Ser Pro Leu His Thr His Leu Ala
            420                 425                 430

Leu Leu Trp Glu Val His Arg Gly Pro Ala Arg Arg Ser Val Leu Ala
        435                 440                 445

Leu Thr His Glu Gly Arg Phe His Pro Gly Leu Gly Tyr Glu Gln Arg
    450                 455                 460

Tyr His Ser Gly Asp Val Arg Leu Asp Thr Val Gly Ser Asp Ala Tyr
465                 470                 475                 480

Arg Leu Ser Val Ser Arg Ala Leu Ser Ala Asp Gln Gly Ser Tyr Arg
                485                 490                 495

Cys Ile Val Ser Glu Trp Ile Ala Glu Gln Gly Asn Trp Gln Glu Ile
            500                 505                 510

Gln Glu Lys Ala Val Glu Val Ala Thr Val Val Ile Gln Pro Ser Val
        515                 520                 525
```

-continued

```
Leu Arg Ala Ala Val Pro Lys Asn Val Ser Val Ala Glu Gly Lys Glu
    530                 535                 540

Leu Asp Leu Thr Cys Asn Ile Thr Thr Asp Arg Ala Asp Asp Val Arg
545                 550                 555                 560

Pro Glu Val Thr Trp Ser Phe Ser Arg Met Pro Asp Ser Thr Leu Pro
                565                 570                 575

Gly Ser Arg Val Leu Ala Arg Leu Asp Arg Asp Ser Leu Val His Ser
            580                 585                 590

Ser Pro His Val Ala Leu Ser His Val Asp Ala Arg Ser Tyr His Leu
        595                 600                 605

Leu Val Arg Asp Val Ser Lys Glu Asn Ser Gly Tyr Tyr Tyr Cys His
    610                 615                 620

Val Ser Leu Trp Ala Pro Gly His Asn Arg Ser Trp His Lys Val Ala
625                 630                 635                 640

Glu Ala Val Ser Ser Pro Ala Gly Val Gly Val Thr Trp Leu Glu Pro
                645                 650                 655

Asp Tyr Gln Val Tyr Leu Asn Ala Ser Lys Val Pro Gly Phe Ala Asp
            660                 665                 670

Asp Pro Thr Glu Leu Ala Cys Arg Val Val Asp Thr Lys Ser Gly Glu
        675                 680                 685

Ala Asn Val Arg Phe Thr Val Ser Trp Tyr Tyr Arg Met Asn Arg Arg
    690                 695                 700

Ser Asp Asn Val Val Thr Ser Glu Leu Leu Ala Val Met Asp Gly Asp
705                 710                 715                 720

Trp Thr Leu Lys Tyr Gly Glu Arg Ser Lys Gln Arg Ala Gln Asp Gly
                725                 730                 735

Asp Phe Ile Phe Ser Lys Glu His Thr Asp Thr Phe Asn Phe Arg Ile
            740                 745                 750

Gln Arg Thr Thr Glu Glu Asp Arg Gly Asn Tyr Tyr Cys Val Val Ser
        755                 760                 765

Ala Trp Thr Lys Gln Arg Asn Asn Ser Trp Val Lys Ser Lys Asp Val
    770                 775                 780

Phe Ser Lys Pro Val Asn Ile Phe Trp Ala Leu Glu Asp Ser Val Leu
785                 790                 795                 800

Val Val Lys Ala Arg Gln Pro Lys Pro Phe Phe Ala Ala Gly Asn Thr
                805                 810                 815

Phe Glu Met Thr Cys Lys Val Ser Ser Lys Asn Ile Lys Ser Pro Arg
            820                 825                 830

Tyr Ser Val Leu Ile Met Ala Glu Lys Pro Val Gly Asp Leu Ser Ser
        835                 840                 845

Pro Asn Glu Thr Lys Tyr Ile Ile Ser Leu Asp Gln Asp Ser Val Val
    850                 855                 860

Lys Leu Glu Asn Trp Thr Asp Ala Ser Arg Val Asp Gly Val Val Leu
865                 870                 875                 880

Glu Lys Val Gln Glu Asp Glu Phe Arg Tyr Arg Met Tyr Gln Thr Gln
                885                 890                 895

Val Ser Asp Ala Gly Leu Tyr Arg Cys Met Val Thr Ala Trp Ser Pro
            900                 905                 910

Val Arg Gly Ser Leu Trp Arg Glu Ala Ala Thr Ser Leu Ser Asn Pro
        915                 920                 925

Ile Glu Ile Asp Phe Gln Thr Ser Gly Pro Ile Phe Asn Ala Ser Val
    930                 935                 940
```

-continued

His Ser Asp Thr Pro Ser Val Ile Arg Gly Asp Leu Ile Lys Leu Phe
945 950 955 960

Cys Ile Ile Thr Val Glu Gly Ala Ala Leu Asp Pro Asp Asp Met Ala
965 970 975

Phe Asp Val Ser Trp Phe Ala Val His Ser Phe Gly Leu Asp Lys Ala
980 985 990

Pro Val Leu Leu Ser Ser Leu Asp Arg Lys Gly Ile Val Thr Thr Ser
995 1000 1005

Arg Arg Asp Trp Lys Ser Asp Leu Ser Leu Glu Arg Val Ser Val
1010 1015 1020

Leu Glu Phe Leu Leu Gln Val His Gly Ser Glu Asp Gln Asp Phe
1025 1030 1035

Gly Asn Tyr Tyr Cys Ser Val Thr Pro Trp Val Lys Ser Pro Thr
1040 1045 1050

Gly Ser Trp Gln Lys Glu Ala Glu Ile His Ser Lys Pro Val Phe
1055 1060 1065

Ile Thr Val Lys Met Asp Val Leu Asn Ala Phe Lys Tyr Pro Leu
1070 1075 1080

Leu Ile Gly Val Gly Leu Ser Thr Val Ile Gly Leu Leu Ser Cys
1085 1090 1095

Leu Ile Gly Tyr Cys Ser Ser His Trp Cys Cys Lys Lys Glu Val
1100 1105 1110

Gln Glu Thr Arg Arg Glu Arg Arg Arg Leu Met Ser Met Glu Met
1115 1120 1125

Asp Tyr Pro Tyr Asp Val Pro Asp Tyr Ala
1130 1135

<210> SEQ ID NO 9
<211> LENGTH: 553
<212> TYPE: PRT
<213> ORGANISM: Artificial sequence
<220> FEATURE:
<223> OTHER INFORMATION: Synthetic polypeptide

<400> SEQUENCE: 9

Met Gly Arg Leu Ala Ser Arg Pro Leu Leu Leu Ala Leu Leu Ser Leu
1 5 10 15

Ala Leu Cys Arg Gly Arg Val Val Arg Gly Ser Gly Arg Ala His Leu
20 25 30

Val Gln Ser Gly Thr Ala Met Lys Lys Pro Gly Ala Ser Val Arg Val
35 40 45

Ser Cys Gln Thr Ser Gly Tyr Thr Phe Thr Ala His Ile Leu Phe Trp
50 55 60

Phe Arg Gln Ala Pro Gly Arg Gly Leu Glu Trp Val Gly Trp Ile Lys
65 70 75 80

Pro Gln Tyr Gly Ala Val Asn Phe Gly Gly Gly Phe Arg Asp Arg Val
85 90 95

Thr Leu Thr Arg Asp Val Tyr Arg Glu Ile Ala Tyr Met Asp Ile Arg
100 105 110

Gly Leu Lys Pro Asp Asp Thr Ala Val Tyr Tyr Cys Ala Arg Asp Arg
115 120 125

Ser Tyr Gly Asp Ser Ser Trp Ala Leu Asp Ala Trp Gly Gln Gly Thr
130 135 140

Thr Val Val Val Ser Ala Gly Ser Asp Ser Asn Ala Gly His Ala Ser
145 150 155 160

-continued

```
Ala Gly Asn Thr Ser Tyr Ile His Val Thr Gln Ser Pro Ser Ser Leu
            165                 170                 175

Ser Val Ser Ile Gly Asp Arg Val Thr Ile Asn Cys Gln Thr Ser Gln
            180                 185                 190

Gly Val Gly Ser Asp Leu His Trp Tyr Gln His Lys Pro Gly Arg Ala
        195                 200                 205

Pro Lys Leu Leu Ile His His Thr Ser Ser Val Glu Asp Gly Val Pro
    210                 215                 220

Ser Arg Phe Ser Gly Ser Gly Phe His Thr Ser Phe Asn Leu Thr Ile
225                 230                 235                 240

Ser Asp Leu Gln Ala Asp Asp Ile Ala Thr Tyr Tyr Cys Gln Val Leu
            245                 250                 255

Gln Phe Phe Gly Arg Gly Ser Arg Leu His Ile Lys Glu Ser Lys Tyr
            260                 265                 270

Gly Pro Pro Cys Pro Pro Cys Pro Ala Pro Glu Phe Glu Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser Gln Glu Asp
305                 310                 315                 320

Pro Glu Val Gln Phe Asn Trp Tyr Val Asp Gly Val Glu Val His Asn
            325                 330                 335

Ala Lys Thr Lys Pro Arg Glu Glu Gln Phe Gln Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Gly Leu Pro Ser Ser Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
            405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Arg Leu Thr Val Asp Lys
    450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
            485                 490                 495

Lys Leu Leu Ile Gly Val Gly Leu Ser Thr Val Ile Gly Leu Leu Ser
            500                 505                 510

Cys Leu Ile Gly Tyr Cys Ser Ser His Trp Cys Cys Lys Lys Glu Val
        515                 520                 525

Gln Glu Thr Arg Arg Glu Arg Arg Arg Leu Met Ser Met Glu Met Asp
    530                 535                 540

Tyr Pro Tyr Asp Val Pro Asp Tyr Ala
545                 550
```

<210> SEQ ID NO 10
<211> LENGTH: 498
<212> TYPE: PRT

```
<213> ORGANISM: Artificial sequence
<220> FEATURE:
<223> OTHER INFORMATION: Synthetic polypeptide

<400> SEQUENCE: 10

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Gly Gly Gly Ser Gly Gly
                165                 170                 175

Gly Ser Gly Gly Gly Ser Gly Gly Gly Ser Glu Val Gln Leu Val Glu
            180                 185                 190

Ser Gly Gly Asp Leu Val Gln Pro Gly Arg Ser Leu Arg Leu Ser Cys
        195                 200                 205

Ala Ala Ser Gly Phe Ile Phe Ser Asn Tyr Gly Met Ser Trp Val Arg
    210                 215                 220

Gln Ala Pro Gly Lys Gly Leu Glu Trp Val Ala Thr Ile Ser Ser Ala
225                 230                 235                 240

Ser Thr Tyr Ser Tyr Tyr Pro Asp Ser Val Lys Gly Arg Phe Thr Ile
                245                 250                 255

Ser Arg Asp Asn Ala Lys Asn Ser Leu Tyr Leu Gln Met Asn Ser Leu
            260                 265                 270

Arg Val Glu Asp Thr Ala Leu Tyr Tyr Cys Gly Arg His Ser Asp Gly
        275                 280                 285

Asn Phe Ala Phe Gly Tyr Trp Gly Gln Gly Thr Leu Val Thr Val Ser
    290                 295                 300

Ser Gly Gly Gly Ser Gly Gly Gly Ser Gly Gly Gly Ser Gly Gly Gly
305                 310                 315                 320

Ser Asp Val Leu Met Thr Gln Ser Pro Leu Ser Leu Pro Val Thr Pro
                325                 330                 335

Gly Glu Pro Ala Ser Ile Ser Cys Arg Ser Ser Arg Asn Ile Val His
            340                 345                 350

Ile Asn Gly Asp Thr Tyr Leu Glu Trp Tyr Leu Gln Lys Pro Gly Gln
        355                 360                 365

Ser Pro Gln Leu Leu Ile Tyr Lys Val Ser Asn Arg Phe Ser Gly Val
    370                 375                 380

Pro Asp Arg Phe Ser Gly Ser Gly Ser Gly Thr Asp Phe Thr Leu Lys
```

385 390 395 400

Ile Ser Arg Val Glu Ala Glu Asp Val Gly Val Tyr Tyr Cys Phe Gln
405 410 415

Gly Ser Leu Leu Pro Trp Thr Phe Gly Gln Gly Thr Lys Val Glu Ile
420 425 430

Lys Gly Gly Gly Ser Gly Gly Gly Ser Gly Gly Gly Ser Gly Gly Gly
435 440 445

Ser Gly Cys Val Glu Lys Ile Gly Gly Trp Leu Arg Lys Asn Val Leu
450 455 460

Val Val Ala Ala Ala Ala Leu Gly Ile Ala Phe Val Glu Val Leu Gly
465 470 475 480

Ile Val Phe Ala Cys Cys Leu Val Lys Ser Ile Arg Ser Gly Tyr Glu
485 490 495

Val Met

<210> SEQ ID NO 11
<211> LENGTH: 496
<212> TYPE: PRT
<213> ORGANISM: Artificial sequence
<220> FEATURE:
<223> OTHER INFORMATION: Synthetic polypeptide

<400> SEQUENCE: 11

Met Ala Val Glu Gly Gly Met Lys Cys Val Lys Phe Leu Leu Tyr Val
1 5 10 15

Leu Leu Leu Ala Phe Cys Ala Cys Ala Val Gly Leu Ile Ala Val Gly
20 25 30

Val Gly Ala Gln Leu Val Leu Ser Gln Thr Ile Ile Gln Gly Ala Thr
35 40 45

Pro Gly Ser Leu Leu Pro Val Val Ile Ile Ala Val Gly Val Phe Leu
50 55 60

Phe Leu Val Ala Phe Val Gly Cys Cys Gly Ala Cys Lys Glu Asn Tyr
65 70 75 80

Cys Leu Met Ile Thr Phe Ala Ile Phe Leu Ser Leu Ile Met Leu Val
85 90 95

Glu Val Ala Ala Ala Ile Ala Gly Tyr Val Phe Arg Asp Lys Val Met
100 105 110

Ser Glu Phe Asn Asn Asn Phe Arg Gln Gln Met Glu Asn Tyr Pro Lys
115 120 125

Asn Asn His Thr Ala Ser Ile Leu Asp Arg Met Gln Ala Asp Phe Lys
130 135 140

Cys Cys Gly Ala Ala Asn Tyr Thr Asp Trp Glu Lys Ile Pro Ser Met
145 150 155 160

Ser Lys Asn Arg Val Pro Asp Ser Cys Cys Gly Gly Gly Ser Gly Gly
165 170 175

Gly Ser Gly Gly Gly Ser Gly Gly Gly Ser Gln Met Gln Leu Val Gln
180 185 190

Ser Gly Thr Glu Val Lys Lys Pro Gly Glu Ser Leu Lys Ile Ser Cys
195 200 205

Lys Gly Ser Gly Tyr Gly Phe Ile Thr Tyr Trp Ile Gly Trp Val Arg
210 215 220

Gln Met Pro Gly Lys Gly Leu Glu Trp Met Gly Ile Ile Tyr Pro Gly
225 230 235 240

Asp Ser Glu Thr Arg Tyr Ser Pro Ser Phe Gln Gly Gln Val Thr Ile
245 250 255

Ser Ala Asp Lys Ser Ile Asn Thr Ala Tyr Leu Gln Trp Ser Ser Leu
260 265 270

Lys Ala Ser Asp Thr Ala Ile Tyr Tyr Cys Ala Gly Gly Ser Gly Ile
275 280 285

Ser Thr Pro Met Asp Val Trp Gly Gln Gly Thr Thr Val Thr Val Gly
290 295 300

Ser Asp Ser Asn Ala Gly His Ala Ser Ala Gly Asn Thr Ser Asp Ile
305 310 315 320

Gln Leu Thr Gln Ser Pro Asp Ser Leu Ala Val Ser Leu Gly Glu Arg
325 330 335

Ala Thr Ile Asn Cys Lys Ser Ser Gln Ser Val Leu Tyr Ser Ser Ile
340 345 350

Asn Lys Asn Tyr Leu Ala Trp Tyr Gln Gln Lys Pro Gly Gln Pro Pro
355 360 365

Lys Leu Leu Ile Tyr Trp Ala Ser Thr Arg Glu Ser Gly Val Pro Asp
370 375 380

Arg Phe Ser Gly Ser Gly Ser Gly Thr Asp Phe Thr Leu Thr Ile Ser
385 390 395 400

Ser Leu Gln Ala Glu Asp Val Ala Val Tyr Tyr Cys Gln Gln Tyr Tyr
405 410 415

Ser Thr Pro Tyr Thr Phe Gly Gln Gly Thr Lys Val Glu Ile Lys Gly
420 425 430

Gly Gly Ser Gly Gly Gly Ser Gly Gly Gly Ser Gly Gly Gly Ser Gly
435 440 445

Cys Val Glu Lys Ile Gly Gly Trp Leu Arg Lys Asn Val Leu Val Val
450 455 460

Ala Ala Ala Ala Leu Gly Ile Ala Phe Val Glu Val Leu Gly Ile Val
465 470 475 480

Phe Ala Cys Cys Leu Val Lys Ser Ile Arg Ser Gly Tyr Glu Val Met
485 490 495

<210> SEQ ID NO 12
<211> LENGTH: 517
<212> TYPE: PRT
<213> ORGANISM: Artificial sequence
<220> FEATURE:
<223> OTHER INFORMATION: Synthetic polypeptide

<400> SEQUENCE: 12

Met Ala Val Glu Gly Gly Met Lys Cys Val Lys Phe Leu Leu Tyr Val
1 5 10 15

Leu Leu Leu Ala Phe Cys Ala Cys Ala Val Gly Leu Ile Ala Val Gly
20 25 30

Val Gly Ala Gln Leu Val Leu Ser Gln Thr Ile Ile Gln Gly Ala Thr
35 40 45

Pro Gly Ser Leu Leu Pro Val Val Ile Ile Ala Val Gly Val Phe Leu
50 55 60

Phe Leu Val Ala Phe Val Gly Cys Cys Gly Ala Cys Lys Glu Asn Tyr
65 70 75 80

Cys Leu Met Ile Thr Phe Ala Ile Phe Leu Ser Leu Ile Met Leu Val
85 90 95

Glu Val Ala Ala Ala Ile Ala Gly Tyr Val Phe Arg Asp Lys Val Met
100 105 110

Ser Glu Phe Asn Asn Asn Phe Arg Gln Gln Met Glu Asn Tyr Pro Lys
115 120 125

```
Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Gly Gly Gly Ser Gly Gly
                165                 170                 175

Gly Ser Gly Gly Gly Ser Gly Gly Gly Ser Gln Val Gln Leu Gln Glu
            180                 185                 190

Ser Gly Gly Gly Leu Val Gln Ala Gly Gly Ser Leu Arg Leu Ser Cys
        195                 200                 205

Ala Ala Ser Gly Arg Thr Phe Ser Glu Tyr Ala Met Gly Trp Phe Arg
    210                 215                 220

Gln Ala Pro Gly Lys Glu Arg Glu Phe Val Ala Thr Ile Ser Trp Ser
225                 230                 235                 240

Gly Gly Ser Thr Tyr Tyr Thr Asp Ser Val Lys Gly Arg Phe Thr Ile
                245                 250                 255

Ser Arg Asp Asn Ala Lys Asn Thr Val Tyr Leu Gln Met Asn Ser Leu
            260                 265                 270

Lys Pro Asp Asp Thr Ala Val Tyr Tyr Cys Ala Ala Ala Gly Leu Gly
        275                 280                 285

Thr Val Val Ser Glu Trp Asp Tyr Asp Tyr Asp Tyr Trp Gly Gln Gly
    290                 295                 300

Thr Gln Val Thr Val Ser Ser Gly Gly Gly Ser Gly Gly Gly Ser Gly
305                 310                 315                 320

Gly Gly Ser Gly Gly Gly Ser Gln Val Gln Leu Gln Glu Ser Gly Gly
                325                 330                 335

Gly Leu Val Gln Ala Gly Gly Ser Leu Arg Leu Ser Cys Ala Ala Ser
            340                 345                 350

Gly Arg Thr Phe Ser Glu Tyr Ala Met Gly Trp Phe Arg Gln Ala Pro
        355                 360                 365

Gly Lys Glu Arg Glu Phe Val Ala Thr Ile Ser Trp Ser Gly Gly Ser
    370                 375                 380

Thr Tyr Tyr Thr Asp Ser Val Lys Gly Arg Phe Thr Ile Ser Arg Asp
385                 390                 395                 400

Asn Ala Lys Asn Thr Val Tyr Leu Gln Met Asn Ser Leu Lys Pro Asp
                405                 410                 415

Asp Thr Ala Val Tyr Tyr Cys Ala Ala Ala Gly Leu Gly Thr Val Val
            420                 425                 430

Ser Glu Trp Asp Tyr Asp Tyr Asp Tyr Trp Gly Gln Gly Thr Gln Val
        435                 440                 445

Thr Val Ser Ser Gly Gly Gly Ser Gly Gly Gly Ser Gly Gly Gly Ser
    450                 455                 460

Gly Gly Gly Ser Gly Cys Val Glu Lys Ile Gly Gly Trp Leu Arg Lys
465                 470                 475                 480

Asn Val Leu Val Val Ala Ala Ala Ala Leu Gly Ile Ala Phe Val Glu
                485                 490                 495

Val Leu Gly Ile Val Phe Ala Cys Cys Leu Val Lys Ser Ile Arg Ser
            500                 505                 510

Gly Tyr Glu Val Met
        515
```

<210> SEQ ID NO 13
<211> LENGTH: 242

-continued

<212> TYPE: PRT
<213> ORGANISM: Artificial sequence
<220> FEATURE:
<223> OTHER INFORMATION: Synthetic polypeptide

<400> SEQUENCE: 13

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Glu Glu Gln Ala Lys
                165                 170                 175

Thr Phe Leu Asp Lys Phe Asn His Glu Ala Glu Asp Leu Phe Tyr Gln
            180                 185                 190

Ser Gly Cys Val Glu Lys Ile Gly Gly Trp Leu Arg Lys Asn Val Leu
        195                 200                 205

Val Val Ala Ala Ala Ala Leu Gly Ile Ala Phe Val Glu Val Leu Gly
    210                 215                 220

Ile Val Phe Ala Cys Cys Leu Val Lys Ser Ile Arg Ser Gly Tyr Glu
225                 230                 235                 240

Val Met

<210> SEQ ID NO 14
<211> LENGTH: 235
<212> TYPE: PRT
<213> ORGANISM: Artificial sequence
<220> FEATURE:
<223> OTHER INFORMATION: Synthetic polypeptide

<400> SEQUENCE: 14

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ile Ile Gln Gly Ala Thr Pro Gly Ser
        35                  40                  45

Leu Leu Pro Val Val Ile Ile Ala Val Gly Val Phe Leu Phe Leu Val
    50                  55                  60

Ala Phe Val Gly Cys Cys Gly Ala Cys Lys Glu Asn Tyr Cys Leu Met
65                  70                  75                  80

-continued

```
Ile Thr Phe Ala Ile Phe Leu Ser Leu Ile Met Leu Val Glu Val Ala
                85                  90                  95

Ala Ala Ile Ala Gly Tyr Val Phe Arg Asp Lys Val Met Ser Glu Phe
            100                 105                 110

Asn Asn Asn Phe Arg Gln Gln Met Glu Asn Tyr Pro Lys Asn Asn His
        115                 120                 125

Thr Ala Ser Ile Leu Asp Arg Met Gln Ala Asp Phe Lys Cys Cys Gly
    130                 135                 140

Ala Ala Asn Tyr Thr Asp Trp Glu Lys Ile Pro Ser Met Ser Lys Asn
145                 150                 155                 160

Arg Val Pro Asp Ser Cys Cys Ile Asn Val Thr Val Gly Cys Gly Ile
                165                 170                 175

Asn Phe Asn Glu Lys Ala Ile His Lys Glu Gly Cys Val Glu Lys Ile
            180                 185                 190

Gly Gly Trp Leu Arg Lys Asn Val Leu Val Val Ala Ala Ala Ala Leu
        195                 200                 205

Gly Ile Ala Phe Val Glu Val Leu Gly Ile Val Phe Ala Cys Cys Leu
    210                 215                 220

Val Lys Ser Ile Arg Ser Gly Tyr Glu Val Met
225                 230                 235


<210> SEQ ID NO 15
<211> LENGTH: 196
<212> TYPE: PRT
<213> ORGANISM: Artificial sequence
<220> FEATURE:
<223> OTHER INFORMATION: Synthetic polypeptide

<400> SEQUENCE: 15

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Gly Cys Val Glu Lys Ile Gly Gly Trp Leu Arg Lys Asn
145                 150                 155                 160

Val Leu Val Val Ala Ala Ala Ala Leu Gly Ile Ala Phe Val Glu Val
                165                 170                 175

Leu Gly Ile Val Phe Ala Cys Cys Leu Val Lys Ser Ile Arg Ser Gly
            180                 185                 190

Tyr Glu Val Met
        195
```

-continued

<210> SEQ ID NO 16
<211> LENGTH: 217
<212> TYPE: PRT
<213> ORGANISM: Artificial sequence
<220> FEATURE:
<223> OTHER INFORMATION: Synthetic polypeptide

<400> SEQUENCE: 16

```
Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Cys Cys Ile Asn Val Thr Val Gly Cys Gly Ile Asn Phe
145                 150                 155                 160

Asn Glu Lys Ala Ile His Lys Glu Gly Cys Val Glu Lys Ile Gly Gly
                165                 170                 175

Trp Leu Arg Lys Asn Val Leu Val Val Ala Ala Ala Ala Leu Gly Ile
            180                 185                 190

Ala Phe Val Glu Val Leu Gly Ile Val Phe Ala Cys Cys Leu Val Lys
        195                 200                 205

Ser Ile Arg Ser Gly Tyr Glu Val Met
    210                 215
```

<210> SEQ ID NO 17
<211> LENGTH: 219
<212> TYPE: PRT
<213> ORGANISM: Artificial sequence
<220> FEATURE:
<223> OTHER INFORMATION: Synthetic polypeptide

<400> SEQUENCE: 17

```
Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95
```

```
Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Gly Cys Val Glu Lys Ile
                165                 170                 175

Gly Gly Trp Leu Arg Lys Asn Val Leu Val Val Ala Ala Ala Ala Leu
            180                 185                 190

Gly Ile Ala Phe Val Glu Val Leu Gly Ile Val Phe Ala Cys Cys Leu
        195                 200                 205

Val Lys Ser Ile Arg Ser Gly Tyr Glu Val Met
    210                 215


<210> SEQ ID NO 18
<211> LENGTH: 418
<212> TYPE: PRT
<213> ORGANISM: Artificial sequence
<220> FEATURE:
<223> OTHER INFORMATION: Synthetic polypeptide

<400> SEQUENCE: 18

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Gly Asn Ser Thr
            20                  25                  30

Met Gly Ser Ser Leu Glu Leu Asn Leu Thr Asp Ser Glu Asn Ala Thr
        35                  40                  45

Cys Leu Tyr Ala Lys Trp Gln Met Asn Phe Thr Val Arg Tyr Glu Thr
    50                  55                  60

Thr Asn Lys Thr Tyr Lys Thr Val Thr Ile Ser Asp His Gly Thr Val
65                  70                  75                  80

Thr Tyr Asn Gly Ser Ile Cys Gly Asp Asp Gln Asn Gly Pro Lys Ile
                85                  90                  95

Ala Val Gln Phe Gly Pro Gly Phe Ser Trp Ile Ala Asn Phe Thr Lys
            100                 105                 110

Ala Ala Ser Thr Tyr Ser Ile Asp Ser Val Ser Phe Ser Tyr Asn Thr
        115                 120                 125

Gly Asp Asn Thr Thr Phe Pro Asp Ala Glu Asp Lys Gly Ile Leu Thr
    130                 135                 140

Val Asp Glu Leu Leu Ala Ile Arg Ile Pro Leu Asn Asp Leu Phe Arg
145                 150                 155                 160

Cys Asn Ser Leu Ser Thr Leu Glu Lys Asn Asp Val Val Gln His Tyr
                165                 170                 175

Trp Asp Val Leu Val Gln Ala Phe Val Gln Asn Gly Thr Val Ser Thr
            180                 185                 190

Asn Glu Phe Leu Cys Asp Lys Asp Lys Thr Ser Thr Val Ala Pro Thr
        195                 200                 205

Ile His Thr Thr Val Pro Ser Pro Thr Thr Thr Pro Thr Pro Lys Glu
    210                 215                 220

Lys Pro Glu Ala Gly Thr Tyr Ser Val Asn Asn Gly Asn Asp Thr Cys
225                 230                 235                 240
```

-continued

Leu Leu Ala Thr Met Gly Leu Gln Leu Asn Ile Thr Gln Asp Lys Val
245 250 255

Ala Ser Val Ile Asn Ile Asn Pro Asn Thr Thr His Ser Thr Gly Ser
260 265 270

Cys Arg Ser His Thr Ala Leu Leu Arg Leu Asn Ser Ser Thr Ile Lys
275 280 285

Tyr Leu Asp Phe Val Phe Ala Val Lys Asn Glu Asn Arg Phe Tyr Leu
290 295 300

Lys Glu Val Asn Ile Ser Met Tyr Leu Val Asn Gly Ser Val Phe Ser
305 310 315 320

Ile Ala Asn Asn Asn Leu Ser Tyr Trp Asp Ala Pro Leu Gly Ser Ser
325 330 335

Tyr Met Cys Asn Lys Glu Gln Thr Val Ser Val Ser Gly Ala Phe Gln
340 345 350

Ile Asn Thr Phe Asp Leu Arg Val Gln Pro Phe Asn Val Thr Gln Gly
355 360 365

Lys Tyr Ser Thr Ala Gln Glu Cys Ser Leu Asp Asp Asp Thr Ile Leu
370 375 380

Ile Pro Ile Ile Val Gly Ala Gly Leu Ser Gly Leu Ile Ile Val Ile
385 390 395 400

Val Ile Ala Tyr Val Ile Gly Arg Arg Lys Ser Tyr Ala Gly Tyr Gln
405 410 415

Thr Leu

<210> SEQ ID NO 19
<211> LENGTH: 879
<212> TYPE: PRT
<213> ORGANISM: Artificial sequence
<220> FEATURE:
<223> OTHER INFORMATION: Synthetic polypeptide

<400> SEQUENCE: 19

Met Gly Arg Leu Ala Ser Arg Pro Leu Leu Leu Ala Leu Leu Ser Leu
1 5 10 15

Ala Leu Cys Arg Gly Arg Val Val Arg Val Pro Thr Ala Thr Leu Val
20 25 30

Arg Val Val Gly Thr Glu Leu Val Ile Pro Cys Asn Val Ser Asp Tyr
35 40 45

Asp Gly Pro Ser Glu Gln Asn Phe Asp Trp Ser Phe Ser Ser Leu Gly
50 55 60

Ser Ser Phe Val Glu Leu Ala Ser Thr Trp Glu Val Gly Phe Pro Ala
65 70 75 80

Gln Leu Tyr Gln Glu Arg Leu Gln Arg Gly Glu Ile Leu Leu Arg Arg
85 90 95

Thr Ala Asn Asp Ala Val Glu Leu His Ile Lys Asn Val Gln Pro Ser
100 105 110

Asp Gln Gly His Tyr Lys Cys Ser Thr Pro Ser Thr Asp Ala Thr Val
115 120 125

Gln Gly Asn Tyr Glu Asp Thr Val Gln Val Lys Val Leu Ala Asp Ser
130 135 140

Leu His Val Gly Pro Ser Ala Arg Pro Pro Pro Ser Leu Ser Leu Arg
145 150 155 160

Glu Gly Glu Pro Phe Glu Leu Arg Cys Thr Ala Ala Ser Ala Ser Pro
165 170 175

-continued

```
Leu His Thr His Leu Ala Leu Leu Trp Glu Val His Arg Gly Pro Ala
            180                 185                 190

Arg Arg Ser Val Leu Ala Leu Thr His Glu Gly Arg Phe His Pro Gly
        195                 200                 205

Leu Gly Tyr Glu Gln Arg Tyr His Ser Gly Asp Val Arg Leu Asp Thr
    210                 215                 220

Val Gly Ser Asp Ala Tyr Arg Leu Ser Val Ser Arg Ala Leu Ser Ala
225                 230                 235                 240

Asp Gln Gly Ser Tyr Arg Cys Ile Val Ser Glu Trp Ile Ala Glu Gln
                245                 250                 255

Gly Asn Trp Gln Glu Ile Gln Glu Lys Ala Val Glu Val Ala Thr Val
            260                 265                 270

Val Ile Gln Pro Ser Val Leu Arg Ala Ala Val Pro Lys Asn Val Ser
        275                 280                 285

Val Ala Glu Gly Lys Glu Leu Asp Leu Thr Cys Asn Ile Thr Thr Asp
    290                 295                 300

Arg Ala Asp Asp Val Arg Pro Glu Val Thr Trp Ser Phe Ser Arg Met
305                 310                 315                 320

Pro Asp Ser Thr Leu Pro Gly Ser Arg Val Leu Ala Arg Leu Asp Arg
                325                 330                 335

Asp Ser Leu Val His Ser Ser Pro His Val Ala Leu Ser His Val Asp
            340                 345                 350

Ala Arg Ser Tyr His Leu Leu Val Arg Asp Val Ser Lys Glu Asn Ser
        355                 360                 365

Gly Tyr Tyr Tyr Cys His Val Ser Leu Trp Ala Pro Gly His Asn Arg
    370                 375                 380

Ser Trp His Lys Val Ala Glu Ala Val Ser Ser Pro Ala Gly Val Gly
385                 390                 395                 400

Val Thr Trp Leu Glu Pro Asp Tyr Gln Val Tyr Leu Asn Ala Ser Lys
                405                 410                 415

Val Pro Gly Phe Ala Asp Asp Pro Thr Glu Leu Ala Cys Arg Val Val
            420                 425                 430

Asp Thr Lys Ser Gly Glu Ala Asn Val Arg Phe Thr Val Ser Trp Tyr
        435                 440                 445

Tyr Arg Met Asn Arg Arg Ser Asp Asn Val Val Thr Ser Glu Leu Leu
    450                 455                 460

Ala Val Met Asp Gly Asp Trp Thr Leu Lys Tyr Gly Glu Arg Ser Lys
465                 470                 475                 480

Gln Arg Ala Gln Asp Gly Asp Phe Ile Phe Ser Lys Glu His Thr Asp
                485                 490                 495

Thr Phe Asn Phe Arg Ile Gln Arg Thr Thr Glu Glu Asp Arg Gly Asn
            500                 505                 510

Tyr Tyr Cys Val Val Ser Ala Trp Thr Lys Gln Arg Asn Asn Ser Trp
        515                 520                 525

Val Lys Ser Lys Asp Val Phe Ser Lys Pro Val Asn Ile Phe Trp Ala
    530                 535                 540

Leu Glu Asp Ser Val Leu Val Val Lys Ala Arg Gln Pro Lys Pro Phe
545                 550                 555                 560

Phe Ala Ala Gly Asn Thr Phe Glu Met Thr Cys Lys Val Ser Ser Lys
                565                 570                 575

Asn Ile Lys Ser Pro Arg Tyr Ser Val Leu Ile Met Ala Glu Lys Pro
            580                 585                 590

Val Gly Asp Leu Ser Ser Pro Asn Glu Thr Lys Tyr Ile Ile Ser Leu
```

```
        595                 600                 605

Asp Gln Asp Ser Val Val Lys Leu Glu Asn Trp Thr Asp Ala Ser Arg
    610                 615                 620

Val Asp Gly Val Val Leu Glu Lys Val Gln Glu Asp Glu Phe Arg Tyr
625                 630                 635                 640

Arg Met Tyr Gln Thr Gln Val Ser Asp Ala Gly Leu Tyr Arg Cys Met
                645                 650                 655

Val Thr Ala Trp Ser Pro Val Arg Gly Ser Leu Trp Arg Glu Ala Ala
            660                 665                 670

Thr Ser Leu Ser Asn Pro Ile Glu Ile Asp Phe Gln Thr Ser Gly Pro
        675                 680                 685

Ile Phe Asn Ala Ser Val His Ser Asp Thr Pro Ser Val Ile Arg Gly
    690                 695                 700

Asp Leu Ile Lys Leu Phe Cys Ile Ile Thr Val Glu Gly Ala Ala Leu
705                 710                 715                 720

Asp Pro Asp Asp Met Ala Phe Asp Val Ser Trp Phe Ala Val His Ser
                725                 730                 735

Phe Gly Leu Asp Lys Ala Pro Val Leu Leu Ser Ser Leu Asp Arg Lys
            740                 745                 750

Gly Ile Val Thr Thr Ser Arg Arg Asp Trp Lys Ser Asp Leu Ser Leu
        755                 760                 765

Glu Arg Val Ser Val Leu Glu Phe Leu Leu Gln Val His Gly Ser Glu
    770                 775                 780

Asp Gln Asp Phe Gly Asn Tyr Tyr Cys Ser Val Thr Pro Trp Val Lys
785                 790                 795                 800

Ser Pro Thr Gly Ser Trp Gln Lys Glu Ala Glu Ile His Ser Lys Pro
                805                 810                 815

Val Phe Ile Thr Val Lys Met Asp Val Leu Asn Ala Phe Lys Tyr Pro
            820                 825                 830

Leu Leu Ile Gly Val Gly Leu Ser Thr Val Ile Gly Leu Leu Ser Cys
        835                 840                 845

Leu Ile Gly Tyr Cys Ser Ser His Trp Cys Cys Lys Lys Glu Val Gln
    850                 855                 860

Glu Thr Arg Arg Glu Arg Arg Arg Leu Met Ser Met Glu Met Asp
865                 870                 875


<210> SEQ ID NO 20
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 20

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
```

```
                85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120


<210> SEQ ID NO 21
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 21

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100


<210> SEQ ID NO 22
<211> LENGTH: 208
<212> TYPE: PRT
<213> ORGANISM: Artificial sequence
<220> FEATURE:
<223> OTHER INFORMATION: Synthetic polypeptide

<400> SEQUENCE: 22

Met Val Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160
```

```
Lys Asn Ile Gln Gly Gly Lys Thr Leu Ser Val Ser Gln Leu Glu Leu
            165                 170                 175

Gln Asp Ser Gly Thr Trp Thr Cys Thr Val Leu Gln Asn Gln Lys Lys
        180                 185                 190

Val Glu Phe Lys Ile Asp Ile Val Val Leu Ala Phe Gln Lys Ala Ser
    195                 200                 205


<210> SEQ ID NO 23
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 23

Met Ala Leu Ile Val Leu Gly Gly Val Ala Gly Leu Leu Leu Phe Ile
1               5                   10                  15

Gly Leu Gly Ile Phe Phe
            20


<210> SEQ ID NO 24
<211> LENGTH: 229
<212> TYPE: PRT
<213> ORGANISM: Artificial sequence
<220> FEATURE:
<223> OTHER INFORMATION: Synthetic polypeptide

<400> SEQUENCE: 24

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 25
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 25

```
Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Ile Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Ser Ala Ser Thr Tyr Ser Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Gly Arg His Ser Asp Gly Asn Phe Ala Phe Gly Tyr Trp Gly Gln Gly
            100                 105                 110

Thr Leu Val Thr Val Ser Ser
        115
```

<210> SEQ ID NO 26
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 26

```
Asp Val Leu Met Thr Gln Ser Pro Leu Ser Leu Pro Val Thr Pro Gly
1               5                   10                  15

Glu Pro Ala Ser Ile Ser Cys Arg Ser Ser Arg Asn Ile Val His Ile
            20                  25                  30

Asn Gly Asp Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Leu Pro Trp Thr Phe Gly Gln Gly Thr Lys Val Glu Ile Lys
            100                 105                 110
```

<210> SEQ ID NO 27
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 27

```
Gln Met Gln Leu Val Gln Ser Gly Thr Glu Val Lys Lys Pro Gly Glu
1               5                   10                  15
```

-continued

```
Ser Leu Lys Ile Ser Cys Lys Gly Ser Gly Tyr Gly Phe Ile Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Glu Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Ala Gly Gly Ser Gly Ile Ser Thr Pro Met Asp Val Trp Gly Gln Gly
            100                 105                 110

Thr Thr Val Thr Val
        115
```

<210> SEQ ID NO 28
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 28

```
Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Ile Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys
```

<210> SEQ ID NO 29
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 29

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Glu Tyr
            20                  25                  30

Ala Met Gly Trp Phe Arg Gln Ala Pro Gly Lys Glu Arg Glu Phe Val
        35                  40                  45

Ala Thr Ile Ser Trp Ser Gly Gly Ser Thr Tyr Tyr Thr Asp Ser Val
    50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Asp Asp Thr Ala Val Tyr Tyr Cys
                85                  90                  95

Ala Ala Ala Gly Leu Gly Thr Val Val Ser Glu Trp Asp Tyr Asp Tyr
            100                 105                 110

Asp Tyr Trp Gly Gln Gly Thr Gln Val Thr Val Ser Ser
        115                 120                 125


<210> SEQ ID NO 30
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 30

Ile Glu Glu Gln Ala Lys Thr Phe Leu Asp Lys Phe Asn His Glu Ala
1               5                   10                  15

Glu Asp Leu Phe Tyr Gln Ser
            20


<210> SEQ ID NO 31
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 31

Gly Gly Gly Ser Gly Gly Gly Ser Gly Gly Gly Ser Gly Gly Gly Ser
1               5                   10                  15


<210> SEQ ID NO 32
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 32

Gly Gly Gly Gly Ser Gly Gly Gly Gly Ser
1               5                   10


<210> SEQ ID NO 33
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 33

Gly Gly Gly Gly Ser
1               5


<210> SEQ ID NO 34
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 34

Gly Ser Gly
1


<210> SEQ ID NO 35
```

-continued

```
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 35

Gly Ser Gly Ser Gly Ser Gly
1               5


<210> SEQ ID NO 36
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 36

Gly Ser Asp Ser Asn Ala Gly His Ala Ser Ala Gly Asn Thr Ser
1               5                   10                  15


<210> SEQ ID NO 37
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 37

Tyr Pro Tyr Asp Val Pro Asp Tyr Ala
1               5
```

CELL-RECEPTOR TARGETED EXOSOMES

CROSS-REFERENCE TO RELATED APPLICATIONS

This application is a Section 371 US national phase of PCT/US2021/026892 filed Apr. 12, 2021, which claims priority to U.S. Application No. 63/009,309 filed Apr. 13, 2020, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under grant no. RMH113407 awarded by National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-749001WO_SequenceListing_ST25.txt, created Apr. 6, 2021, 95,244 bytes, machine format IBM-PC, MS Windows operating system, is hereby incorporated by reference.

BACKGROUND

Exosomes are derived from cells and contain both proteins and various cellular transcripts. Notably, exosomes are host specific and are generated by virtually every cell in the human body and are able to bind to cells, become internalized and pass the endosome delivering payloads that facilitate cell-to-cell communication. Exosomes can also be designed and developed to deliver therapeutic payloads, including some that can transit across the blood brain barrier. Methods to direct exosomes to particular cell types would be useful in developing strategies to utilize exosomes as targeted therapeutics. The disclosure is directed to this, as well as other, important ends.

BRIEF SUMMARY

The disclosure provides exosome comprising a recombinant fusion protein, wherein the recombinant fusion protein comprises an exosome membrane-associated protein and an exogenous target protein. The disclosure also provides pharmaceutical compositions and cells comprising the exosomes; and methods of treating diseases with the exosomes. These and other embodiments and aspects of the disclosure are provided in detail herein.

BRIEF DESCRIPTION OF THE DRAWINGS

FIG. 1A is a schematic is shown depicting the approach to developing N6-CD63 gp160 expressing cells. FIG. 1B shows various extracellular loci in the CD63 exosome expressed transmembrane protein were assessed for tolerance of the HIV gp120 targeted N6 broadly neutralizing scFv.

FIG. 3A: exosomes were harvested from 293HEK cells transfected with the CD63 vectors fused to Nanoluc, quantified and added in equal amounts to 293HEK or 293HEK-GP160 expressing cells and luciferase measured 18 hours later. Luciferase was normalized between the cell lines and made relative to the control (CD63 only), which was set to 1.0. The results of a single experiment are shown. FIG. 3B: HEK293 stably expressing GP160 cells were transfected and treated with exosomes expression variants of N6-CD63 or a D1-D2 and compared to control exosomes. The levels of nluc was assessed 18 hrs after addition. Errors bars represent standard deviation and were generated by treatments performed in triplicate. P values were generated by a one-way ANOVA (**$p<0.005$).

FIG. 4A is a CD63 fusion which involves the generation of a CD63 fusion to the N6-ScFv in either loop 1 or loop 2. FIG. 4B is a Lamp2b fusion and FIG. 4C is PTGFRN fusion. FIGS. 4A and 4B contain two versions; a first version which contains the wild-type receptor with the N6 ScFv embedded after the leader peptide (LP), or a second version which involves the replacement of the receptor with IgG but retains the LP and transmembrane domain (TM) in order to maintain those signals required for exosome localization.

FIG. 5A: detection of the nanoluciferase (Nluc), as a proxy for VHH72-CD63-nluc incorporation, and exosomal markers (CD63, TSG101, ALIX, CD81) in exosomes and cell lysate that express the VHH72-CD63 and CD63 control vector. FIGS. 5B-5C: HEK293 cells were transfected with a spike expressing vector, and high levels of spike protein were detected (FIG. 5B), and exosomes were added to the spike expressing cells and the levels of Nluc was assessed 4 hrs after addition. FIG. 5D: bead coated with anti-CD63 antibodies were bound exosomes which were incubated with a COV-2 RBD-His tag and then detected by an anti-His antibody conjugated to a fluorophore. Errors bars represent standard deviation and were generated by treatments performed in triplicate. P values were generated by a one-way ANOVA (*$p<0.05$).

FIG. 6A: lentiviral vector pseudotyped with WT spike, spike-D614G, or spike-D614G-R682Q were transduced with increasing amounts of lentiviral particles on HEK293 with stable hACE2 or hACE2 and TMPRSS2 and compared to WT HEK293 cells. The lentiviral particles were packaged with a GFP-Fluc transgene and the levels of luciferase was assessed at 48-72 hrs after transduction. FIG. 6B: VHH72-CD63 exosomes were pre-incubated with pseudotyped spike lentiviral (D614G and D614G-R682Q) and then used to infect HEK293-hACE2-TMPRSS2 and the levels of Fluc were assessed at 48 hrs post transduction. Exosomes expressing CD63 were included as a negative control. FIG. 6C: a dose response effect was observed with VHH72-CD63 exosome against the D614G-R682Q pseudotyped virus. Errors bars represent standard deviation and were generated by treatments performed in triplicate.

DETAILED DESCRIPTION

Definitions

Figure 1A:
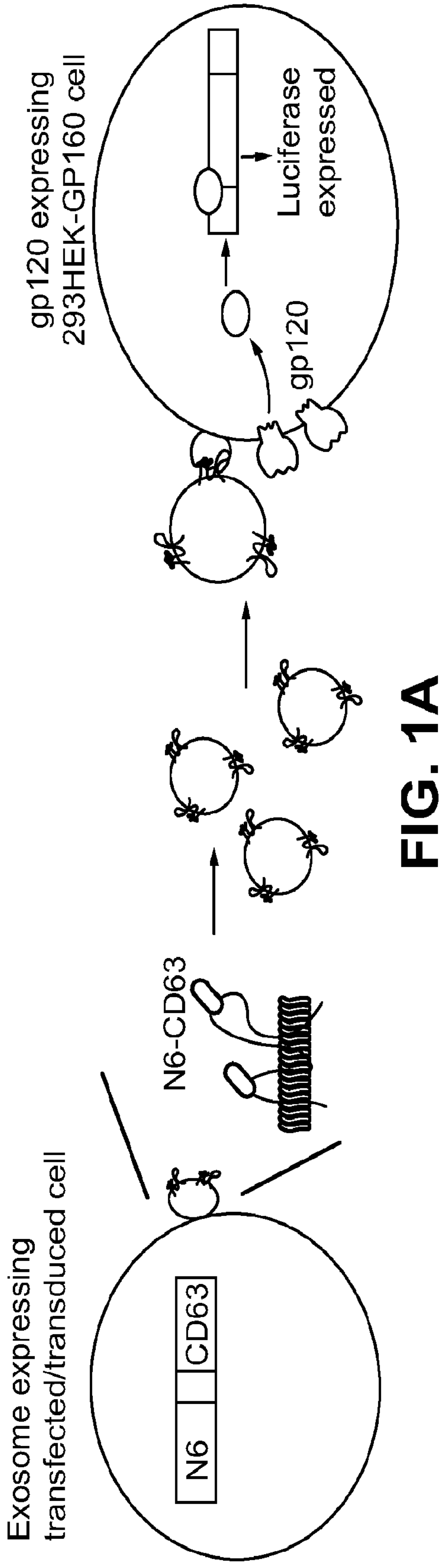
FIGS. 1A-1B show graphics for receptor targeted exosomes.

The abbreviations used herein have their conventional meaning within the chemical and biological arts. The chemical structures and formulae set forth herein are constructed according to the standard rules of chemical valency known in the chemical arts.

The term "extracellular vesicle" refers to a cell-derived vesicle comprising a membrane that encloses an internal space. Extracellular vesicles comprise all membrane-bound vesicles that have a smaller diameter than the cell from which they are derived. Generally extracellular vesicles range in diameter from 20 nm to 1000 nm, and can comprise various macromolecular cargo either within the internal space, displayed on the external surface of the extracellular vesicle, and/or spanning the membrane. The cargo can comprise nucleic acids, proteins, carbohydrates, lipids, small molecules, and/or combinations thereof. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, and cultured cells.

The term "exosome" refers to a cell-derived small (between 20-300 nm in diameter) vesicle comprising a membrane that encloses an internal space, and which is generated from the cell by direct plasma membrane budding or by fusion of the late endosome with the plasma membrane. The exosome comprises lipid and/or fatty acid and optionally comprises a payload (e.g., a therapeutic agent), a receiver (e.g., a targeting peptide), a polynucleotide (e.g., a nucleic acid, RNA, or DNA), a sugar (e.g., a simple sugar, polysaccharide, or glycan) or other molecules or drugs. The exosome can be derived from a producer cell, and isolated from the producer cell based on its size, density, biochemical parameters, or a combination thereof. An exosome is a species of extracellular vesicle.

An "exosome membrane-associated protein" refers to a membrane protein on the exosome, such as a transmembrane protein, an integral protein, or a peripheral protein. Exosome membrane-associated protein include various CD proteins, transporters, integrins, lectins and cadherins. Exemplary membrane-associated proteins include CD9, CD37, CD53, CD63, CD68, CD81, CD82, LAMP-1, LAMP-2A, LAMP-2B, LAMP-2C, lactadherin, PTGFRN, BSG, IGSF3, IGSF8, ITGB1, ITGA4, SLC3A2, IGSF2, and ATP transporter proteins (ATP1A1, ATP1A2, ATP1A3, ATP1A4, ATP1B3, ATP2B1, ATP2B2, ATP2B3, ATP2B4).

An "exogenous target protein" refers to a protein that can be used to target the exosome to a specific organ, tissue, cell, virus, protein, or bacteria for a treatment using the exosomes described herein. In aspects, the exogenous target protein binds to or is capable of binding to a cell, protein, virus, or bacteria of interest. In aspects, the exogenous target protein is a receptor agonist. In aspects, the exogenous target protein is a cytokine. In aspects, the exogenous target protein is a chemokine. In aspects, the exogenous protein is an RNA binding protein. In aspects, the targeting protein is an antibody or antigen-binding fragment thereof. Antibodies and antigen-binding fragments thereof include whole antibodies, polyclonal, monoclonal and recombinant antibodies, fragments thereof, and further include single-chain antibodies, humanized antibodies, murine antibodies, chimeric, mouse-human, mouse-primate, primate-human monoclonal antibodies, anti-idiotype antibodies, antibody fragments, such as, e.g., scFv, $(scFv)_2$, Fab, Fab', and $F(ab')_2$, $F(ab1)_2$, Fv, dAb, and Fd fragments, diabodies, and antibody-related polypeptides. Antibodies and antigen-binding fragments thereof also includes bispecific antibodies and multispecific antibodies so long as they exhibit the desired biological activity or function.

The terms "bind" and "bound" as used herein is used in accordance with its plain and ordinary meaning and refers to the association between atoms or molecules. The association can be direct or indirect. For example, bound atoms or molecules may be bound, e.g., by covalent bond, linker (e.g. a first linker or second linker), or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "capable of binding" as used herein refers to a moiety (e.g. a target protein as described herein) that is able to measurably bind to a target (e.g., a NF-κB, a Toll-like receptor protein). In aspects, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

The term "exogenous" refers to a molecule or substance (e.g., peptide, protein) that originates from outside a given cell or organism. For example, an "exogenous protein" as referred to herein is a protein that does not originate from the cell or organism. The term "endogenous protein" refers to a protein that is native to, or originates within, a given cell or organism.

The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express proteins that are not found within the native (non-recombinant) form of the cell.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

A "fusion protein" refers to a chimeric protein encoding two or more separate protein sequences that are recombinantly expressed as a single moiety. Because the different proteins in fusion proteins may affect the functionality of other proteins under certain circumstances, peptide linkers may be used between different proteins within the same fusion protein. These peptide linkers may have a flexible structure and separate the proteins within the fusion protein so that each protein in the fusion proteins substantially retains its function. Peptide linkers are known in the art and described, for example, in Chen et al, Adv Drug Deliv Rev, 65(10); 1357-1369 (2013).

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M) (see, e.g., Creighton, Proteins (1984)).

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain. In embodiments, the amino acid side chain is H,

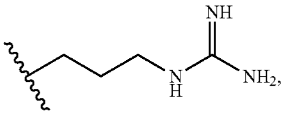, 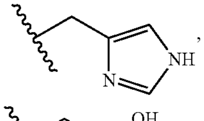, 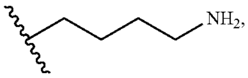, 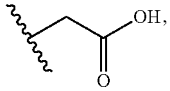, 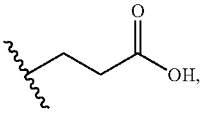, 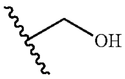, 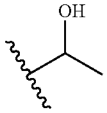, 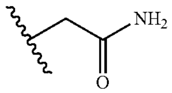, 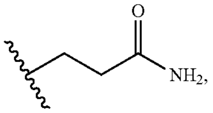, 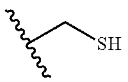, 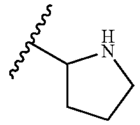, 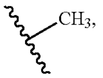, 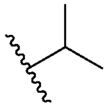, 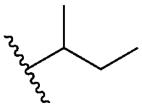, 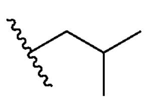, 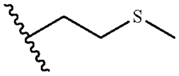, 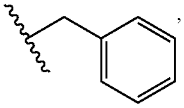, 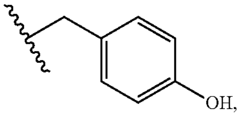, or 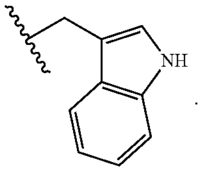.

The term "non-natural amino acid side chain" refers to the functional substituent of compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium, allylalanine, 2 -aminoisobutryric acid. Non-natural amino acids are non-proteinogenic amino acids that either occur naturally or are chemically synthesized. Such analogs have modified R groups (e.g., norleucine) or modified peptide backbones, but retain the same basic chemical structure as a naturally occurring amino acid. Non-limiting examples include exo-cis-3-aminobicyclo[2.2.1]-hept-5-ene-2-carboxylic acid hydrochloride, cis-2-aminocycloheptanecarboxylic acid hydrochloride,cis-6-amino-3-cyclohexene-1-carboxylic acid hydrochloride, cis-2-amino-2-methylcyclohexane-carboxylic acid hydrochloride, cis-2-amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe (4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl] acetic acid purum, Boc-β-(2-quinolyl)-Ala-OH, N-Boc-1,2,3,6-tetrahydro-2-pyridinecarboxylic acid, Boc-β-(4-thiazolyl)-Ala-OH, Boc-β-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, Fmoc-β-(2-thienyl)-Ala-OH, 4-(Hydroxymethyl)-D-phenylalanine.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain" or "$V_H$," refers to the variable region of an immunoglobulin heavy chain, including an Fv, scFv, dsFv or Fab; while the terms "variable light chain" or "$V_L$" refers to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., Fundamental Immunology (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody includes antibody fragments either produced by the modification of whole antibodies, or those synthesized de novo using recombinant DNA methodologies (e.g., single chain Fv) or those identified using phage display libraries (see, e.g., McCafferty et al., (1990) Nature 348:552). The term "antibody" also includes bivalent or bispecific molecules, diabodies, triabodies, and tetrabodies. Bivalent and bispecific molecules are described in, e.g., Kostelny et al. (1992) J. Immunol. 148:1547, Pack and Pluckthun (1992) Biochemistry 31:1579, Hollinger et al. (1993), PNAS. USA 90:6444, Gruber et al. (1994) J Immunol. 152:5368, Zhu et al. (1997) Protein Sci. 6:781, Hu et al. (1996) Cancer Res. 56:3055, Adams et al. (1993) Cancer Res. 53:4026, and McCartney, et al. (1995) Protein Eng. 8:301.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

The term "CD63" refers to a protein that, in humans, is encoded by the CD63 gene. CD63 is associated with membranes of extracellular vesicles, intracellular vesicles, and exosomes. The term "CD63" as provided herein includes any of the protein naturally occurring forms, homologs or variants that maintain the activity of CD63 (e.g., within at least 50%, 80%, 90%, 95%, 96%, 97%, 98%, 99% or 100% activity compared to the native protein). In aspects, variants or homologs have at least 90%, 95%, 96%, 97%, 98%, 99% or 100% amino acid sequence identity across the whole sequence or a portion of the sequence (e.g. a 10, 20, 25, 30, 40, 50, 100, 150 or 200 continuous amino acid portion) compared to a naturally occurring form. In aspects, the CD63 protein has the amino acid sequence identified as UniProtKB Reference Number P08962. In aspects, the CD63 protein has the amino acid sequence identified as UniProtKB Reference Number A0A024RB05.

The terms "LAMP-2B" and "Lamp2b" and "lysosome-associated membrane glycoprotein 2B" refer to a protein that, in humans, is encoded by the LAMP2 gene. Lamp2b is associated with membranes of extracellular vesicles, intracellular vesicles, and exosomes. The term "Lamp2b" as provided herein includes any of the protein naturally occurring forms, homologs or variants that maintain the activity of Lamp2b (e.g., within at least 50%, 80%, 90%, 95%, 96%, 97%, 98%, 99% or 100% activity compared to the native protein). In aspects, variants or homologs have at least 90%, 95%, 96%, 97%, 98%, 99% or 100% amino acid sequence identity across the whole sequence or a portion of the sequence (e.g. a 10, 20, 25, 30, 40, 50, 100, 150 or 200 continuous amino acid portion) compared to a naturally occurring form. In aspects, the Lamp2b protein has the amino acid sequence identified as UniProtKB Reference Number P13473.

The terms "PTGFRN" and "prostaglandin F2 receptor negative regulator" refer to a protein that, in humans, is encoded by the PTGFRN gene. PTGFRN is associated with membranes of extracellular vesicles, intracellular vesicles, and exosomes. The term "PTGFRN" as provided herein includes any of the protein naturally occurring forms, homologs or variants that maintain the activity of PTGFRN (e.g., within at least 50%, 80%, 90%, 95%, 96%, 97%, 98%, 99% or 100% activity compared to the native protein). In aspects, variants or homologs have at least 90%, 95%, 96%, 97%, 98%, 99% or 100% amino acid sequence identity across the whole sequence or a portion of the sequence (e.g. a 10, 20, 25, 30, 40, 50, 100, 150 or 200 continuous amino acid portion) compared to a naturally occurring form. In aspects, the PTGFRN protein has the amino acid sequence identified as UniProtKB Reference Number Q9P2B2.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of nucleic acids contemplated herein include single and double stranded DNA, single and double stranded RNA, and hybrid molecules having mixtures of single and double stranded DNA and RNA. Examples of nucleic acids contemplated herein include any types of RNA (e.g., antisense RNA, mRNA, siRNA, miRNA, shRNA, guide RNA, dicer substrate RNA, dicer substrate siRNAs (dsiRNAs) (dsiRNA are cleaved by the RNase III class endoribonuclease dicer into 21-23 base duplexes having 2-base 3'-overhangs siRNA), and any type of DNA, genomic DNA, plasmid DNA, and minicircle DNA, and any fragments thereof. The term "duplex" in the context of nucleic acids refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as 2'O-methyl, 2'O-methoxyethoxy, 2'fluoro, 5-methyl cytidine or pseudouridine; and peptide nucleic acid backbones and linkages. Other analog nucleic acids include those with positive backbones; non-ionic backbones, modified sugars (e.g., deoxyribose), and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In aspects, the internucleotide linkages in DNA are phosphodiester, phosphodiester derivatives, or a combination of both.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

An "antisense nucleic acid" as referred to herein is a nucleic acid (e.g., DNA or RNA molecule) that is complementary to at least a portion of a specific target nucleic acid and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. See, e.g., Weintraub, Scientific American, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid. In aspects, the antisense nucleic acid hybridizes to the target nucleic acid in vitro. In aspects, the antisense nucleic acid hybridizes to the target nucleic acid in a cell. In aspects, the antisense nucleic acid hybridizes to the target nucleic acid in an organism. In aspects, the antisense nucleic acid hybridizes to the target nucleic acid under physiological conditions. Antisense nucleic acids may comprise naturally occurring nucleotides or modified nucleotides such as, e.g., phosphorothioate, methylphosphonate, and anomeric sugar-phosphate, backbone-modified nucleotides.

In the cell, the antisense nucleic acids hybridize to the corresponding RNA forming a double-stranded molecule. The antisense nucleic acids interfere with the endogenous behavior of the RNA and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, Anal. Biochem., 172:289, (1988)). Further, antisense molecules which bind directly to the DNA may be used. Antisense nucleic acids may be single or double stranded nucleic acids. Non-limiting examples of antisense nucleic acids include small interfering RNAs (siRNAs)(including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

"siRNA" and "small interfering RNA" as provided herein refers to a double-stranded or single-stranded ribonucleic acid that has the ability to reduce or inhibit expression of a gene or the activity of a target nucleic acid (e.g., a single-stranded or double-stranded RNA or a single-stranded or doubles-stranded DNA) when expressed in the same cell as the gene or target gene. Where the siRNA is a double-stranded RNA, the complementary portions of the ribonucleic acid that hybridize to form the double stranded molecule typically have substantial or complete identity. In aspects, an siRNA is a nucleic acid that has substantial or complete identity to a target RNA and forms a double stranded siRNA. In aspects, the siRNA inhibits gene expression by interacting with a complementary cellular RNA thereby interfering with the endogenous behavior of the complementary cellular RNA. Typically, the siRNA is about 15-50 nucleotides in length (e.g., each complementary sequence of the double stranded siRNA is 15-50 nucleotides in length, and the double stranded siRNA is about 15-50 base pairs in length). The siRNAs provided herein regulate expression of a target gene or activity of a target nucleic by hybridizing to the mRNA of the gene or by hybridizing to the promoter of the target nucleic or the target nucleic acid itself. Where the siRNA hybridizes to a promoter of a gene thereby modulating the expression of said gene, the siRNA may be referred to as "antigen RNA" or "agRNA." In aspects, the nucleic acid sequences provided herein are siRNA.

"Hybridize" and "hybridization" refer to the pairing of complementary (including partially complementary) nucleic acid strands. Hybridization and the strength of hybridization (e.g., the strength of the association between nucleic acid strands) is impacted by factors known in the art including the degree of complementarity between the nucleic acid, stringency of the conditions involved affected by such conditions as the concentration of salts, the melting temperature (Tm) of the formed hybrid, the presence of other components, the molarity of the hybridizing strands and the G:C content of the nucleic acid strands. When one nucleic acid is said to "hybridize" to another nucleic acid, it means that there is some complementarity between the two nucleic acids or that the two nucleic acids form a hybrid under high or low stringency conditions.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The phrase "hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary hybridization conditions can be as follows: 50% formamide, 5×SSC, and 1% SDS, incubating at 42° C., or 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For PCR amplification, a temperature of about 62° C. is typical, although high stringency annealing temperatures can range from about 50° C. to about 65° C. depending on the primer length and specificity. Typical cycle conditions for both high and low stringency amplifications include a denaturation phase of 90° C.-95° C. for 30 seconds to 2 minutes, an annealing phase lasting 30 seconds to 2 minutes, and an extension phase of about 72° C. for 1-2 min. Protocols and guidelines for low and high stringency amplification reactions are provided, e.g., in Innis et al., PCR Protocols, A Guide to Methods and Applications, Academic Press, Inc. N.Y. (1990).

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In aspects, the nucleic acids described herein are isolated nucleic acids.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "activation", "activate", "activating", "activator" and the like in reference to a protein-inhibitor interaction means positively affecting (e.g. increasing) the activity or function of the protein relative to the activity or function of the protein in the absence of the activator. In aspects activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

The term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In aspects inhibition means negatively affecting (e.g. decreasing) the concentration or levels of the protein relative to the concentration or level of the protein in the absence of the inhibitor. In aspects inhibition refers to reduction of a disease or symptoms of disease. In aspects, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In aspects, inhibition refers to a reduction of activity of a target protein resulting from a direct interaction (e.g. an inhibitor binds to the target protein). In aspects, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "target gene" refers to any nucleic acid sequence which contains an identified genes or a target region within a gene, including intergenic regions, non-coding regions, untranscribed regions, introns, exons, and transgenes. The target gene (or a target site within the gene) can be a gene derived from a cell, an endogenous gene, a transgene, or exogenous genes such as genes of a pathogen, for example a virus, which is present in the cell after infection thereof. The cell containing the target gene can be derived from or contained in any organism.

Exosomes

The disclosure provides exosomes comprising a recombinant fusion protein, wherein the recombinant fusion protein comprises an exosome membrane-associated protein and an exogenous target protein. In aspects, the target protein is within the membrane-associated protein. In aspects, the recombinant fusion protein further comprises a peptide linker, an epitope tag, an IgG scFv, or a combination of two or more thereof. In aspects, the recombinant fusion protein further comprises at least one peptide linker, an epitope tag, an IgG scFv, or a combination of two or more thereof. In aspects, the recombinant fusion protein further comprises at least one peptide linker. In aspects, the recombinant fusion protein further comprises at least one peptide linker and an epitope tag. In aspects, the recombinant fusion protein further comprises at least one peptide linker, an epitope tag, and an IgG scFv. In aspects, the recombinant fusion protein further comprises at least one peptide linker and an IgG scFv. In aspects, the recombinant fusion protein further comprises an epitope tag and an IgG scFv. In aspects, the recombinant fusion protein further comprises an epitope tag. In aspects, the recombinant fusion protein further comprises an IgG scFv.

Exosome membrane-associated proteins are known in the art and any exosome membrane-associated protein can be used in the recombinant fusion protein described herein. In aspects, the exosome membrane-associated protein is CD9, CD37, CD53, CD63, CD68, CD81, CD82, LAMP-1, LAMP-2A, LAMP-2B, LAMP-2C, lactadherin, or PTGFRN. In aspects, the exosome membrane-associated protein is CD63, LAMP-2B, or PTGFRN. In aspects, the exosome membrane-associated protein is CD63. In aspects, the exosome membrane-associated protein is LAMP-2B. In aspects, the exosome membrane-associated protein is PTGFRN. In aspects, the exosome membrane-associated protein is an endogenous membrane-associated protein. In aspects, the exosome membrane-associated protein is an exogenous protein. In aspects, the membrane-associated protein is an integral part of the exosome (e.g., an endogenous membrane-associated protein).

The disclosure provides exosomes comprising a recombinant fusion protein, wherein the recombinant fusion protein comprises an exosome membrane-associated protein and an exogenous target protein, wherein the membrane-associated protein is CD63 and the target protein is within the CD63 membrane-associated protein. In aspects, the target protein is within an extracellular loop of the CD63 membrane-associated protein. In aspects, the CD63 membrane-associated protein has at least 80%, 85%, 90%, 95%, or 100% identity to SEQ ID NO:14, SEQ ID NO:15, SEQ ID NO:16, or SEQ ID NO:17.

The disclosure provides exosomes comprising a recombinant fusion protein, wherein the recombinant fusion protein comprises an exosome membrane-associated protein and an exogenous target protein, wherein the membrane-associated protein is CD63 and the target protein is within extracellular loop 1 of CD63. In aspects, extracellular loop 1 of CD63 has an amino acid sequence that is at least 75% identical to SEQ ID NO:14. In aspects, extracellular loop 1 of CD63 has an amino acid sequence that is at least 80% identical to SEQ ID NO:14. In aspects, extracellular loop 1 of CD63 has an amino acid sequence that is at least 85% identical to SEQ ID NO:14. In aspects, extracellular loop 1 of CD63 has an amino acid sequence that is at least 90% identical to SEQ ID NO:14. In aspects, extracellular loop 1 of CD63 has an amino acid sequence that is at least 92% identical to SEQ ID NO:14. In aspects, extracellular loop 1 of CD63 has an amino acid sequence that is at least 94% identical to SEQ ID NO:14. In aspects, extracellular loop 1 of CD63 has an amino acid sequence that is at least 95% identical to SEQ ID NO:14. In aspects, extracellular loop 1 of CD63 has an amino acid sequence that is at least 96% identical to SEQ ID NO:14. In aspects, extracellular loop 1 of CD63 has an amino acid sequence that is at least 98% identical to SEQ ID NO:14. In aspects, extracellular loop 1 of CD63 has an amino acid sequence that is 100% identical to SEQ ID NO:14.

The disclosure provides exosomes comprising a recombinant fusion protein, wherein the recombinant fusion protein comprises an exosome membrane-associated protein and an exogenous target protein, wherein the membrane-associated protein is CD63 and the target protein is within extracellular loop 2 of CD63. In aspects, extracellular loop 2 of CD63 has an amino acid sequence that is at least 75% identical to SEQ ID NO:15. In aspects, extracellular loop 2 of CD63 has an amino acid sequence that is at least 80% identical to SEQ ID NO:15. In aspects, extracellular loop 2 of CD63 has an amino acid sequence that is at least 85% identical to SEQ ID NO:15. In aspects, extracellular loop 2 of CD63 has an amino acid sequence that is at least 90% identical to SEQ ID NO:15. In aspects, extracellular loop 2 of CD63 has an amino acid sequence that is at least 92% identical to SEQ ID NO:15. In aspects, extracellular loop 2 of CD63 has an amino acid sequence that is at least 94% identical to SEQ ID NO:15. In aspects, extracellular loop 2 of CD63 has an amino acid sequence that is at least 95% identical to SEQ ID NO:15. In aspects, extracellular loop 2 of CD63 has an amino acid sequence that is at least 96% identical to SEQ ID NO:15. In aspects, extracellular loop 2 of CD63 has an amino acid sequence that is at least 98% identical to SEQ ID NO:15. In aspects, extracellular loop 2 of CD63 has an amino acid sequence that is 100% identical to SEQ ID NO:15.

The disclosure provides exosomes comprising a recombinant fusion protein, wherein the recombinant fusion protein comprises an exosome membrane-associated protein and an exogenous target protein, wherein the membrane-associated protein is CD63 and the target protein is within extracellular loop 2 of CD63. In aspects, extracellular loop 2 of CD63 has an amino acid sequence that is at least 75% identical to SEQ ID NO:16. In aspects, extracellular loop 2 of CD63 has an amino acid sequence that is at least 80% identical to SEQ ID NO:16. In aspects, extracellular loop 2 of CD63 has an amino acid sequence that is at least 85% identical to SEQ ID NO:16. In aspects, extracellular loop 2 of CD63 has an amino acid sequence that is at least 90% identical to SEQ ID NO:16. In aspects, extracellular loop 2 of CD63 has an amino acid sequence that is at least 92% identical to SEQ ID NO:16. In aspects, extracellular loop 2 of CD63 has an amino acid sequence that is at least 94% identical to SEQ ID NO:16. In aspects, extracellular loop 2 of CD63 has an amino acid sequence that is at least 95% identical to SEQ ID NO:16. In aspects, extracellular loop 2 of CD63 has an amino acid sequence that is at least 96% identical to SEQ ID NO:16. In aspects, extracellular loop 2 of CD63 has an amino acid sequence that is at least 98% identical to SEQ ID NO:16. In aspects, extracellular loop 2 of CD63 has an amino acid sequence that is 100% identical to SEQ ID NO:16.

The disclosure provides exosomes comprising a recombinant fusion protein, wherein the recombinant fusion protein comprises an exosome membrane-associated protein and an exogenous target protein, wherein the membrane-associated protein is CD63 and the target protein is within an extracellular loop 2 of CD63. In aspects, extracellular loop 2 of CD63 has an amino acid sequence that is at least 75% identical to SEQ ID NO:17. In aspects, extracellular loop 2 of CD63 has an amino acid sequence that is at least 80% identical to SEQ ID NO:17. In aspects, extracellular loop 2 of CD63 has an amino acid sequence that is at least 85% identical to SEQ ID NO:17. In aspects, extracellular loop 2 of CD63 has an amino acid sequence that is at least 90% identical to SEQ ID NO:17. In aspects, extracellular loop 2 of CD63 has an amino acid sequence that is at least 92% identical to SEQ ID NO:17. In aspects, extracellular loop 2 of CD63 has an amino acid sequence that is at least 94% identical to SEQ ID NO:17. In aspects, extracellular loop 2 of CD63 has an amino acid sequence that is at least 95% identical to SEQ ID NO:17. In aspects, extracellular loop 2 of CD63 has an amino acid sequence that is at least 96% identical to SEQ ID NO:17. In aspects, extracellular loop 2 of CD63 has an amino acid sequence that is at least 98% identical to SEQ ID NO:17. In aspects, extracellular loop 2 of CD63 has an amino acid sequence that is 100% identical to SEQ ID NO:17.

The disclosure provides exosomes comprising a recombinant fusion protein, wherein the recombinant fusion protein comprises an exosome membrane-associated protein and an exogenous target protein, wherein the membrane-associated protein is LAMP-2B and the target protein is within the membrane-associated protein. In aspects, LAMP-2B has an amino acid sequence that is at least 75% identical to SEQ ID NO:18. In aspects, LAMP-2B has an amino acid sequence that is at least 80% identical to SEQ ID NO:18. In aspects, LAMP-2B has an amino acid sequence that is at least 85% identical to SEQ ID NO:18. In aspects, LAMP-2B has an amino acid sequence that is at least 90% identical to SEQ ID NO:18. In aspects, LAMP-2B has an amino acid sequence that is at least 92% identical to SEQ ID NO:18. In aspects, LAMP-2B has an amino acid sequence that is at least 94% identical to SEQ ID NO:18. In aspects, LAMP-2B has an amino acid sequence that is at least 95% identical to SEQ ID NO:18. In aspects, LAMP-2B has an amino acid sequence that is at least 96% identical to SEQ ID NO:18. In aspects, LAMP-2B has an amino acid sequence that is at least 98% identical to SEQ ID NO:18. In aspects, LAMP-2B has an amino acid sequence that is 100% identical to SEQ ID NO:18.

The disclosure provides exosomes comprising a recombinant fusion protein, wherein the recombinant fusion protein comprises an exosome membrane-associated protein and an exogenous target protein, wherein the membrane-associated protein is PTGFRN and the target protein is within the membrane-associated protein. In aspects, PTGFRN has an amino acid sequence that is at least 75% identical to SEQ ID NO:19. In aspects, PTGFRN has an amino acid sequence that is at least 80% identical to SEQ ID NO:19. In aspects, PTGFRN has an amino acid sequence that is at least 85% identical to SEQ ID NO:19. In aspects, PTGFRN has an amino acid sequence that is at least 90% identical to SEQ ID NO:19. In aspects, PTGFRN has an amino acid sequence that is at least 92% identical to SEQ ID NO:19. In aspects, PTGFRN has an amino acid sequence that is at least 94% identical to SEQ ID NO:19. In aspects, PTGFRN has an amino acid sequence that is at least 95% identical to SEQ ID NO:19. In aspects, PTGFRN has an amino acid sequence that is at least 96% identical to SEQ ID NO:19. In aspects, PTGFRN has an amino acid sequence that is at least 98% identical to SEQ ID NO:19. In aspects, PTGFRN has an amino acid sequence that is 100% identical to SEQ ID NO:19.

In embodiments, the exogenous target protein within the membrane-associated protein is any protein that is capable of targeting (e.g., binding to, modulating, activating, inhibiting) a cell, a protein, a virus, or a bacteria. In aspects, the target protein is a single chain variable fragment (scFv). In aspects, the scFv comprises a heavy chain variable fragment, a light chain variable fragment, or a combination thereof. In aspects, the scFv comprises a heavy chain variable fragment is covalently bonded to a light chain variable fragment. In aspects, the scFv comprises a heavy chain variable fragment covalently bonded directly to a light chain variable fragment. In aspects, the scFv comprises a heavy chain variable fragment covalently bonded via a peptide linker to a light chain variable fragment. In aspects, the target protein (e.g., scFv) is "within" the membrane-associated protein. In aspects, the term "within" means that the scFv is located between any two amino acids at any location in the membrane-associated protein, e.g., the scFv is after the first amino acid from the 5' end of the membrane associated protein; or after the second amino acid from the 5' end of the membrane-associated protein; or after the tenth, fifteenth, twentieth, or twenty-fifth amino acid from the 5' end of the membrane-associated protein. In aspects, the term "within" is represented by the formula: $-5'-X_1-L_1-V_H-L_2-V_L-L_3-X_2-3'-$, where $V_H$ is the scFv heavy chain variable fragment, $V_L$ is the scFv light chain variable fragment, $L_1$, $L_2$, and $L_3$ are each independently a peptide linker; and $5'-X_1-$ and $-X_2-3'$ together form 5'-X-3', where X is the membrane-associated protein. In aspects, the term "within" can is represented by the following structure: $-5'-X_1-(L_1)_p-V_H-(L_2)_p-V_L-(L_3)_p-X_2-3'-$, where p is 0 or 1. In aspects, the term "within" can is represented by the following structure: $-5'-X_1-(L_1)_p-V_H-(L_2)_p-X_2-3'-$; where p is 0 or 1. In aspects, the term "within" can is represented by the following structure: $-5'-X_1-(L_2)_p-V_L-(L_3)_p-X_2-3'-$; where p is 0 or 1. In aspects, the term "within" can is represented by the following structure: $-5'-X_1-(L_1)_p-V_H-(L_2)_p-V_H-(L_3)_p-X_2-3'-$; where p is 0 or 1. In aspects, the term "within" can is represented by the following structure: $-5'-X_1-(L_1)_p-V_L-(L_2)_p-V_L-(L_3)_p-X_2-3'-$; wherein p is 0 or 1. In other words, the scFv and optionally-associated peptide linkers (e.g., $-L_1-V_H-L_2-V_L-L_3-$) are inserted between any two amino acids within the membrane-associated protein. In aspects, the term "within" means that the scFv is adjacent the 5' end of the membrane-associate protein or adjacent the 3' end of the membrane associated protein. In aspects, the recombinant fusion protein further comprises an epitope tag. In aspects, the epitope tag is an HA epitope tag. In aspects, the scFv targets HIV. In aspects, the scFv targets SARS-CoV-2. In aspects, the scFv targets HTLV-1. In aspects, the scFv targets cancer cells.

In aspects, the term "within" is represented by the formula: $-5'-X_1-(L_1)_p-V_H-(L_2)_p-V_L-(L_3)_p-IgG-(L_4)_p-X_2-3'-$, where $V_H$ is the scFv heavy chain variable fragment, $V_L$ is the scFv light chain variable fragment, $L_1$, $L_2$, $L_3$, and $L_4$ are each independently a peptide linker; IgG is an IgG antibody scFv (e.g., SEQ ID NO:24), p is 0 or 1, and $5'-X_1-$ and $-X_2-3'$ together form 5'-X-3', where X is the membrane-associated protein. In aspects, the term "within" is represented by the formula $-5'-X_1-(L_1)_p-V_H-(L_2)_p-V_L-IgG-X_2-3'-$. In aspects, the term "within" is represented by the formula $-5'-X_1-(L_1)_p-V_H-(L_2)_p-V_L-L_3-IgG-X_2-3'-$. In aspects, the term "within" is represented by the formula $-5'-X_1-(L_1)_p-V_H-(L_2)_p-V_L-IgG-L_4-X_2-3'-$. In aspects, the term "within" is represented by the formula $-5'-X_1-(L_1)_p-V_H-(L_2)_p-V_L-L_3-IgG-L_4-X_2-3'-$. In aspects, the IgG is an IgG heavy chain variable region, an IgG light chain variable region, or a combination thereof. In aspects, the IgG is an IgG heavy chain variable region. In aspects, the IgG is an IgG light chain variable region. In aspects, the IgG has at least 80% sequence identity to SEQ ID NO:24. In aspects, the IgG has at least 85% sequence identity to SEQ ID NO:24. In aspects, the IgG has at least 90% sequence identity to SEQ ID NO:24. In aspects, the IgG has at least 92% sequence identity to SEQ ID NO:24. In aspects, the IgG has at least 94% sequence identity to SEQ ID NO:24. In aspects, the IgG has at least 95% sequence identity to SEQ ID NO:24. In aspects, the IgG has at least 96% sequence identity to SEQ ID NO:24. In aspects, the IgG has at least 98% sequence identity to SEQ ID NO:24. In aspects, the IgG has 100% sequence identity to SEQ ID NO:24. In aspects, the recombinant fusion protein further comprises an epitope tag. In aspects, the epitope tag is an HA epitope tag.

In aspects, the target protein is an scFv that targets the human immunodeficiency virus (HIV). Any scFv known in the art that targets HIV can be used in the exosomes and recombinant fusion proteins described herein. In aspects, the scFv is N6. In aspects, the scFv has a heavy chain variable fragment with an amino acid sequence having least 80% identity to SEQ ID NO:20; and the light chain variable fragment has an amino acid sequence with at least 80% identity to SEQ ID NO:21. In aspects, the heavy chain variable fragment has an amino acid sequence with at least 85% identity to SEQ ID NO:20; and the light chain variable fragment has an amino acid sequence with at least 85% identity to SEQ ID NO:21. In aspects, the heavy chain variable fragment has an amino acid sequence with at least 90% identity to SEQ ID NO:20; and the light chain variable fragment has an amino acid sequence with at least 90% identity to SEQ ID NO:21. In aspects, the heavy chain variable fragment has an amino acid sequence with at least 95% identity to SEQ ID NO:20; and the light chain variable fragment has an amino acid sequence with at least 95% identity to SEQ ID NO:21. In aspects, the heavy chain variable fragment has an amino acid sequence with 100% identity to SEQ ID NO:20; and the light chain variable fragment has an amino acid sequence with 100% identity to SEQ ID NO:21.

In aspects, the target protein is an scFv that targets a severe acute respiratory syndrome (SARS) virus. In aspects the SARS virus is SARS-coronavirus. In aspects, the SARS-coronavirus is SARS-coronavirus 1 (SARS-CoV-1). In aspects, the SARS-coronavirus is MERS-coronavirus (MERS-CoV). In aspects, the SARS-coronavirus is SARS-coronavirus 2 (SARS-CoV-2). In aspects, the scFv is VHH-72. In aspects, the scFv is CR3022. In aspects, the scFv has a heavy chain variable fragment, a light chain variable fragment, or both heavy chain and light chain variable fragments that target Spike expressing cells on SARS-CoV. In aspects, the scFv has a heavy chain variable fragment, a light chain variable fragment, or both heavy chain and light chain variable fragments that target the Spike (S) glycoprotein on SARS-CoV. In aspects, the scFv has a heavy chain variable fragment, a light chain variable fragment, or both heavy chain and light chain variable fragments that target the nucleocapsid protein (N) on SARS-CoV. In aspects, the scFv has a heavy chain variable fragment, a light chain variable fragment, or both heavy chain and light chain variable fragments that target the membrane protein (M) on SARS-CoV. In aspects, the scFv has a heavy chain variable fragment, a light chain variable fragment, or both heavy chain and light chain variable fragments that target the envelope protein (E) on SARS-CoV. In aspects, the fusion protein further comprises an epitope tag. In aspects, the fusion protein further comprises an IgG scFv. In aspects, the scFv has a heavy chain variable fragment with an amino acid sequence having least 80% identity to SEQ ID NO:27; and the light chain variable fragment has an amino acid sequence with at least 80% identity to SEQ ID NO:28. In aspects, the heavy chain variable fragment has an amino acid sequence with at least 85% identity to SEQ ID NO:27; and the light chain variable fragment has an amino acid sequence with at least 85% identity to SEQ ID NO:28. In aspects, the heavy chain variable fragment has an amino acid sequence with at least 90% identity to SEQ ID NO:27; and the light chain variable fragment has an amino acid sequence with at least 90% identity to SEQ ID NO:28. In aspects, the heavy chain variable fragment has an amino acid sequence with at least 95% identity to SEQ ID NO:27; and the light chain variable fragment has an amino acid sequence with at least 95% identity to SEQ ID NO:28. In aspects, the heavy chain variable fragment has an amino acid sequence with 100% identity to SEQ ID NO:27; and the light chain variable fragment has an amino acid sequence with 100% identity to SEQ ID NO:28. In aspects, the scFv has a heavy chain variable fragment with an amino acid sequence having least 80% identity to SEQ ID NO:29. In aspects, the scFv has a heavy chain variable fragment with an amino acid sequence having least 85% identity to SEQ ID NO:29. In aspects, the scFv has a heavy chain variable fragment with an amino acid sequence having least 90% identity to SEQ ID NO:29. In aspects, the scFv has a heavy chain variable fragment with an amino acid sequence having least 92% identity to SEQ ID NO:29. In aspects, the scFv has a heavy chain variable fragment with an amino acid sequence having least 94% identity to SEQ ID NO:29. In aspects, the scFv has a heavy chain variable fragment with an amino acid sequence having least 95% identity to SEQ ID NO:29. In aspects, the scFv has a heavy chain variable fragment with an amino acid sequence having least 96% identity to SEQ ID NO:29. In aspects, the scFv has a heavy chain variable fragment with an amino acid sequence having least 98% identity to SEQ ID NO:29. In aspects, the scFv has a heavy chain variable fragment with an amino acid sequence has 100% identity to SEQ ID NO:29. In aspects, the fusion protein further comprises an epitope tag. In aspects, the fusion protein further comprises an IgG scFv. Accordingly, the disclosure provides methods of treating COVID-19 in a subject in need thereof by administering an effective amount of the exosomes described herein.

In aspects, the target protein is a protein that targets (e.g., binds to) a severe acute respiratory syndrome (SARS) virus (e.g., SARS-coronavirus, SARS-coronavirus 1 (SARS-CoV-1), MERS-coronavirus (MERS-CoV), or SARS-coronavirus 2 (SARS-CoV-2)). In aspects the SARS is SARS-CoV-2. In aspects, the target protein is an angiotensin-converting enzyme 2 (ACE2) peptide. In aspects, the ACE2 peptide has at least 80% sequence identity to SEQ ID NO:30. In aspects, the ACE2 peptide has at least 85% sequence identity to SEQ ID NO:30. In aspects, the ACE2 peptide has at least 90% sequence identity to SEQ ID NO:30. In aspects, the ACE2 peptide has at least 92% sequence identity to SEQ ID NO:30. In aspects, the ACE2 peptide has at least 94% sequence identity to SEQ ID NO:30. In aspects, the ACE2 peptide has at least 95% sequence identity to SEQ ID NO:30. In aspects, the ACE2 peptide has at least 96% sequence identity to SEQ ID NO:30. In aspects, the ACE2 peptide has at least 98% sequence identity to SEQ ID NO:30. In aspects, the ACE2 peptide has at least 100% sequence identity to SEQ ID NO:30.

In aspects, the target protein is an scFv that targets human T-cell lymphotropic virus type 1 (HTLV-1). In aspects, the target protein is an scFv that targets T-cell leukemia (ATL) cancer cells. In aspects, the scFv is targeted to CCR4. In aspects, the scFv has a heavy chain variable fragment with an amino acid sequence having at least 80% identity to SEQ ID NO:25; and the light chain variable fragment has an amino acid sequence with at least 80% identity to SEQ ID NO:26. In aspects, the heavy chain variable fragment has an amino acid sequence with at least 85% identity to SEQ ID NO:25; and the light chain variable fragment has an amino acid sequence with at least 85% identity to SEQ ID NO:26. In aspects, the heavy chain variable fragment has an amino acid sequence with at least 90% identity to SEQ ID NO:25; and the light chain variable fragment has an amino acid sequence with at least 90% identity to SEQ ID NO:26. In aspects, the heavy chain variable fragment has an amino acid sequence with at least 95% identity to SEQ ID NO:25; and the light chain variable fragment has an amino acid sequence with at least 95% identity to SEQ ID NO:26. In aspects, the heavy chain variable fragment has an amino acid sequence with 100% identity to SEQ ID NO:25; and the light chain variable fragment has an amino acid sequence with 100% identity to SEQ ID NO:26.

In embodiments, the exogenous target protein is a protein receptor agonists. Exemplary protein receptor agonists include a CD4 domain (e.g., D1D2, CD4 transmembrane domain), a chemokine (e.g., CCR4, CCL22, CCL17, MIP-1-α, MIP-1-β, C-X-C motif chemokine), or a cytokine (e.g., an interleukin, e.g., IL-1, IL-1 IL-1α, IL-1β, IL-2, IL-3, IL-4, IL-5, IL-6, IL-7, IL-8, IL-9, IL-10, IL-11, IL-12, IL-13, IL-18). In aspects, the exogenous target protein is a chemokine. In aspects, the exogenous target protein is a cytokine. In aspects, the exogenous target protein is ACE2 (e.g., hACE2). In aspects, the exogenous target protein is hACE2-derived peptide. In aspects, the exogenous target protein is a CCR4. In aspects, the target protein is CCL17. In aspects, the target protein is CCL22. In aspects, the target protein is a nanobody. In aspects, the target protein is an artificial peptide. In aspects, the receptor agonist is a CD4 D1D2 domain having SEQ ID NO:22, a CD4 transmembrane domain having SEQ ID NO:23, or a combination thereof. In aspects, the receptor agonist is an ACE2 peptide having SEQ ID NO:30. In aspects, the receptor agonist is an ACE2 peptide having at least 90% identity to SEQ ID NO:30. In aspects, the receptor agonist is an ACE2 peptide having at least 95% sequence identity to SEQ ID NO:30. In aspects, the target protein (e.g., protein receptor agonist) is "within" the membrane-associated protein. In aspects, the term "within" means that the protein receptor agonist is located between any two amino acids at any location in the membrane-associated protein, e.g., the protein receptor agonist is after the first amino acid from the 5' end of the membrane associated protein; or after the second amino acid from the 5' end of the membrane-associated protein; or after the tenth, fifteenth, twentieth, or twenty-fifth amino acid from the 5' end of the membrane-associated protein. In aspects, the term "within" is represented by the formula: $-5'-X_1-(L_1)_p-P_{RA}-(L_2)_p-X_2-3'-$, where $P_{RA}$ is the protein receptor agonist, $L_1$, $L_2$, and $L_3$ are each independently a peptide linker; p is 0 or 1; and 5'-$X_1$- and -$X_2$-3' together form 5'-X-3', where X is the membrane-associated protein. In aspects, the term "within" is represented by the formula -5'-$X_1$-$P_{RA}$-$X_2$-3'-. In aspects, the term "within" is represented by the formula -5'-$X_1$-$L_1$-$P_{RA}$-$L_2$-$X_2$-3'-. In aspects, the term "within" is represented by the formula -5'-X1-$P_{RA}$-$L_2$-$X_2$-3'-. In aspects, the term "within" is represented by the formula -5'-$X_1$-$L_1$-$P_{RA}$-$X_2$-3'-. In other words, the protein receptor agonist and optionally-associated peptide linkers are inserted between any two amino acids within the membrane-associated protein. In aspects, the term "within" means that the scFv is adjacent the 5' end of the membrane-associate protein or adjacent the 3' end of the membrane associated protein. In aspects, the protein receptor agonist targets HIV. In aspects, the protein receptor agonist targets SARS-CoV. In aspects, the protein receptor agonist targets HTLV-1. In aspects, the protein receptor agonist targets cancer cells.

In embodiments, the exogenous target protein is an RNA binding protein. In aspects, the RNA binding protein is L7ae, L30e, RBM5, RBM6, RBM7, RMB22, RMB32, RBM41, YBX1, YBX2, CSDE1, PTBP1, ZC3H3, ZC3H15, MATR3, SAMD4A, YTHDC2, CUGBP2, PUM2, RC3H2, ZC3H11A, PARP12, CSDA, SFRS8, EIF4B, U2AF2, SFRS14, SPEN, ELVAL1, THUMPD1, DHX8, SRBD1, PABPC1, DAZAP1, IFG2PB2, ZNF638, SART3, MKRN2, MBNL3, SNRPA, SYNJ2, A2BP1, DDX43, KIAA0020, CNOT4, YTHDC1, PPIE, CHERP, KHSRP, or FUS. In aspects, the RNA binding protein is L7ae. In aspects, the RNA binding protein has a least 85% sequence identity to the RNA binding proteins described herein. In aspects, the RNA binding protein has a least 90% sequence identity to the RNA binding proteins described herein. In aspects, the RNA binding protein has a least 95% sequence identity to the RNA binding proteins described herein.

The peptide linker described herein can be any peptide linker known in the art. In aspects, the peptide linker is -$(GGGGS)_n$- where n is an integer from 1 to 6. In aspects, the peptide linker is -$(GGGS)_n$- where n is an integer from 1 to 6. In aspects, the peptide linker is -$(GS)_n$G- where n is an integer from 1 to 6. In aspects, the peptide linker is -$(GGS)_n$G- where n is an integer from 1 to 6. In aspects, the peptide linker is -$(GGS)_n$GG- where n is an integer from 1 to 6. In aspects, n is 1. In aspects, n is 2. In aspects, n is 3. In aspects, n is 4. In aspects, n is 5. In aspects, n is 6. In aspects, the peptide linker is -$(Gly)_m$- where m is an integer from 1 to 12. Other variations of Gly-Ser linkers known in the art can be used. In aspects, the peptide linker is SEQ ID NO:31. In aspects, the peptide linker is SEQ ID NO:32. In aspects, the peptide linker is SEQ ID NO:33. In aspects, the peptide linker is SEQ ID NO:34. In aspects, the peptide linker is SEQ ID NO:35. In aspects, the peptide linker is SEQ ID NO:36.

In aspects, recombinant fusion protein further comprises an epitope tag. In aspects, the epitope tag is HA, HIS, FLAG, AU1, AUS, Myc, Glu-Glu, OLLAS, T7, V5, VSV-G, E-Tag, S-Tag, Avi, HSV, KT3, TK15, GST, or Strep-tag II. In aspects, the epitope tag is HA. The amino acid sequences of epitope tags are known in the art. For example the HA tag is SEQ ID NO:37.

Exosomes can be produced by any method known in the art. For example, exosomes can be produced from a cell grown in vitro or a body fluid of a subject. When exosomes are produced from in vitro cell culture, various producer cells, e.g., HEK293 cells, Chinese hamster ovary (CHO) cells, or mesenchymal stem cells (MSCs), can be used. The producer cell is genetically modified to comprise the recombinant fusion protein described herein. The genetically-modified producer cell can contain the sequence of the recombinant fusion protein introduced by transient or stable transformation. The sequence of the recombinant fusion protein can be introduced to the producer cell as a plasmid. The sequence of the recombinant fusion protein can be stably integrated into a genomic sequence of the producer cell, at a targeted site or in a random site. In aspects, a stable cell line is generated for production of the exosomes described herein. The sequence of the recombinant fusion protein can be inserted into a genomic sequence of the producer cell, located within, upstream (5'-end) or downstream (3'-end) of an endogenous sequence encoding the exosome protein. Various methods known in the art can be used for the introduction of the sequence of the recombinant fusion protein into the producer cell. For example, cells modified using various gene editing methods (e.g., methods using a homologous recombination, transposon-mediated system, loxP-Cre system, CRISPR/Cas9 or TALEN) are within the scope of the disclosure. The sequence of the recombinant fusion protein can comprise a sequence encoding the exosome protein or a variant or a fragment of the exosome protein. An extra copy of the sequence encoding the exosome protein can be introduced to produce the exosomes described herein having the recombinant fusion protein at a higher density. An exogenous sequence encoding a variant or a fragment of the recombinant fusion protein can be introduced to produce the exosomes described herein containing the modification or the fragment of the exosome protein. An exogenous sequence encoding an affinity tag can be introduced to produce the exosomes described herein containing a fusion protein comprising the affinity tag attached.

The disclosure provides cells comprising the exosomes described herein. In aspects, the cells are mammalian cells. In aspects, the cell is a CD4+ T cell, CD8+ T cell, macrophage, liver sinusoidal endothelial cell, CD133+ cell, or a stem cell. In aspects, the stem cell is a hematopoietic stem cell or a mesenchymal stem cell. In aspects, the stem cell is a hematopoietic stem cell is a CD34+ hematopoietic stem cell. In aspects, the cell is a CD4+ T cell. In aspects, the cell is a CD8+ T cell. In aspects, the cell is a macrophage. In aspects, the cell is a liver sinusoidal endothelial cell. In aspects, the cell is a stem cell. In aspects, the stem cell is a hematopoietic stem cell. In aspects, the cell is a mesenchymal stem cell. In aspects, the cell is a CD34+ hematopoietic stem cell.

The disclosure provides exosomes which comprise a recombinant fusion protein, wherein the recombinant fusion protein has an amino acid sequence that is at least 80% identical to any one of SEQ ID NOS:1-13. In aspects, the exosomes comprise a recombinant fusion protein having an amino acid sequence that is at least 85% identical to any one of SEQ ID NOS:1-13. In aspects, the exosomes comprise a recombinant fusion protein having an amino acid sequence that is at least 90% identical to any one of SEQ ID NOS:1-13. In aspects, the exosomes comprise a recombinant fusion protein having has an amino acid sequence that is at least 92% identical to any one of SEQ ID NOS:1-13. In aspects, the exosomes comprise a recombinant fusion protein having an amino acid sequence that is at least 94% identical to any one of SEQ ID NOS:1-13. In aspects, the exosomes comprise a recombinant fusion protein having an amino acid sequence that is at least 95% identical to any one of SEQ ID NOS:1-13. In aspects, the exosomes comprise a recombinant fusion protein having an amino acid sequence that is at least 96% identical to any one of SEQ ID NOS:1-13. In aspects, the exosomes comprise a recombinant fusion protein having an amino acid sequence that is at least 98% identical to any one of SEQ ID NOS:1-13. In aspects, the exosomes comprise a recombinant fusion protein having an amino acid sequence that is 100% identical to any one of SEQ ID NOS:1-13. In aspects, the recombinant fusion protein is SEQ ID NO:1. In aspects, the recombinant fusion protein is SEQ ID NO:2. In aspects, the recombinant fusion protein is SEQ ID NO:3. In aspects, the recombinant fusion protein is SEQ ID NO:4. In aspects, the recombinant fusion protein is SEQ ID NO:5. In aspects, the recombinant fusion protein is SEQ ID NO:6. In aspects, the recombinant fusion protein is SEQ ID NO:7. In aspects, the recombinant fusion protein is SEQ II NO:8. In aspects, the recombinant fusion protein is SEQ ID NO:9. In aspects, the recombinant fusion protein is SEQ ID NO:10. In aspects, the recombinant fusion protein is SEQ II) NO:11. In aspects, the recombinant fusion protein is SEQ ID NO:12. In aspects, the recombinant fusion protein is SEQ ID NO:13.

The disclosure provides recombinant fusion proteins, wherein the recombinant fusion protein has an amino acid sequence that is at least 80% identical to any one of SEQ ID NOS:1-13. In aspects, the recombinant fusion protein has an amino acid sequence that is at least 85% identical to any one of SEQ ID NOS:1-13. In aspects, the recombinant fusion protein has an amino acid sequence that is at least 90% identical to any one of SEQ ID NOS:1-13. In aspects, the recombinant fusion protein has an amino acid sequence that is at least 92% identical to any one of SEQ ID NOS:1-13. In aspects, the recombinant fusion protein has an amino acid sequence that is at least 94% identical to any one of SEQ ID NOS:1-13. In aspects, the recombinant fusion protein has an amino acid sequence that is at least 95% identical to any one of SEQ ID NOS:1-13. In aspects, the recombinant fusion protein has an amino acid sequence that is at least 96% identical to any one of SEQ ID NOS:1-13. In aspects, the recombinant fusion protein has an amino acid sequence that is at least 98% identical to any one of SEQ ID NOS:1-13. In aspects, the recombinant fusion protein has an amino acid sequence that is 100% identical to any one of SEQ ID NOS:1-13. In aspects, the recombinant fusion protein is SEQ ID NO:1. In aspects, the recombinant fusion protein is SEQ ID NO:2. In aspects, the recombinant fusion protein is SEQ ID NO:3. In aspects, the recombinant fusion protein is SEQ NO:41. In aspects, the recombinant fusion protein is SEQ ID NO:5. In aspects, the recombinant fusion protein is SEQ ID NO:6. In aspects, the recombinant fusion protein is SEQ ID NO:7. In aspects, the recombinant fusion protein is SEQ ID NO:8. In aspects, the recombinant fusion protein is SEQ ID NO:9. In aspects, the recombinant fusion protein is SEQ ID NO:10. In aspects, the recombinant fusion protein is SEQ ID NO:11. In aspects, the recombinant fusion protein is SEQ ID NO:12. In aspects, the recombinant fusion protein is SEQ ID NO:13.

Pharmaceutical Compositions

Provided herein are pharmaceutical compositions comprising exosomes and a pharmaceutically acceptable excipient. The compositions are suitable for formulation and administration in vitro or in vivo. Suitable carriers and excipients and their formulations are known in the art and described, e.g., in Remington: The Science and Practice of Pharmacy, 21st Edition, David B. Troy, ed., Lippicott Williams & Wilkins (2005).

"Pharmaceutically acceptable excipient" and "pharmaceutically acceptable carrier" refer to a substance that aids the administration of the exosomes to and absorption by a subject and can be included in the compositions of the disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful.

Solutions of the exosomes can be prepared in water suitably mixed with a lipid or surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions. The intranasal composition can be a spray, aerosol, or inhalant. The inhalable composition can be a spray, aerosol, or inhalant. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate exosomes stabilizers, if required, may be included in the formulation. Various commercial nasal preparations are known in the art.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In aspects, oral pharmaceutical compositions will comprise an inert diluent or edible carrier, or they may be enclosed in hard or soft shell gelatin capsule, or they may be compressed into tablets, or they may be incorporated directly with food. For oral therapeutic administration, the exosomes may be incorporated with excipients and used in the form of ingestible tablets, buccal tablets, troches, capsules, elixirs, suspensions, syrups, wafers, and the like. The percentage of the compositions and preparations may, of course, be varied and may be between about 1 to about 75% of the weight of the unit. The amount of exosomes in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the exosomes in the required amount in the appropriate solvent followed by filtered sterilization. Generally, dispersions are prepared by incorporating the various sterilized exosomes into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. Dimethyl sulfoxide (DMSO) can be used as solvent for extremely rapid penetration, delivering high concentrations of the active agents to a small area.

The formulations of exosomes can be presented in unit-dose or multi-dose sealed containers, such as nebulizers, ventilators, ampules, and vials. Thus, the composition can be in unit dosage form. In such form the preparation is subdivided into unit doses containing appropriate quantities of exosomes. Thus, the compositions can be administered in a variety of unit dosage forms depending upon the method of administration. For example, unit dosage forms suitable for oral administration include, but are not limited to, powder, tablets, pills, capsules and lozenges.

The exosomes and pharmaceutical compositions can be administered to the patient in any manner as described herein. In aspects, the disclosure provides a drug delivery device comprising the exosomes or pharmaceutical compositions described herein. In aspects, the disclosure provides a nebulizer comprising the exosomes or pharmaceutical compositions described herein. In aspects, the disclosure provides a syringe comprising the exosomes or pharmaceutical compositions described herein. In aspects, the disclosure provides a ventilator comprising the exosomes or pharmaceutical compositions described herein. In aspects, the disclosure provides a ventilator which comprises a nebulizer comprising the exosomes or pharmaceutical compositions described herein. Drug delivery devices, such as nebulizers, ventilators, and syringes, are commercially available and well known in the art.

Methods of Treatment

The exosomes can be used to treat any disease by selecting a target protein that will target specific cells, proteins, viruses, or bacteria associated with a particular disease. The skilled artisan could readily recognize what target protein (e.g., scFv) should be selected to treat any particular disease, and can include that target protein within the exosome membrane-associated protein, as described herein.

The terms "disease" refers to a state of being or health status of a patient or subject capable of being treated with the exosomes, fusion proteins, or methods provided herein. The disease may be a cancer, an autoimmune disease, an inflammatory disease, or an infectious disease.

The terms "virus" or "virus particle" are used according to its plain ordinary meaning within virology and refer to a virion including the viral genome (e.g. DNA, RNA, single strand, double strand), viral capsid and associated proteins, and in the case of enveloped viruses (e.g. herpesvirus), an envelope including lipids and optionally components of host cell membranes, and/or viral proteins.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian or human cells.

The disclosure provides methods of treating severe acute respiratory syndrome (SARS) in a subject in need thereof by administering an effective amount of the exosomes described herein. The disclosure provides methods of treating SARS-coronavirus in a subject in need thereof by administering an effective amount of the exosomes described herein. The disclosure provides methods of treating SARS-coronavirus 1 in a subject in need thereof by administering an effective amount of the exosomes described herein. The disclosure provides methods of treating MERS-coronavirus in a subject in need thereof by administering an effective amount of the exosomes described herein. The disclosure provides methods of treating SARS-coronavirus 2 in a subject in need thereof by administering an effective amount of the exosomes described herein. The disclosure provides methods of treating COVID-19 in a subject in need thereof by administering an effective amount of the exosomes described herein.

The disclosure provides methods of treating HIV or AIDS in a subject in need thereof by administering an effective amount of the exosomes described herein. The disclosure provides methods of treating HIV in a subject in need thereof by administering an effective amount of the exosomes described herein. The disclosure provides methods of treating AIDS in a subject in need thereof by administering an effective amount of the exosomes described herein.

The disclosure provides methods of treating HTLV-1 in a subject in need thereof by administering an effective amount of the exosomes described herein. The disclosure provides methods of treating HTLV-1 associated myelopathy/tropical spastic paraparesis in a subject in need thereof by administering an effective amount of the exosomes described herein. The disclosure provides methods of treating leukemia in a subject in need thereof by administering an effective amount of the exosomes described herein. The disclosure provides methods of treating T-cell leukemia in a subject in need thereof by administering an effective amount of the exosomes described herein. The disclosure provides methods of treating adult T-cell leukemia in a subject in need thereof by administering an effective amount of the exosomes described herein. The disclosure provides methods of treating acute T-cell leukemia in a subject in need thereof by administering an effective amount of the exosomes described herein.

The disclosure provides methods of treating a cardiovascular disease in a subject in need thereof by administering an effective amount of the exosomes described herein. As used herein, the term "cardiovascular disease" is used in accordance with its plain ordinary meaning. In embodiments, cardiovascular diseases include stroke, heart failure, hypertension, hypertensive heart disease, myocardial infarction, angina pectoris, tachycardia, cardiomyopathy, rheumatic heart disease, cardiomyopathy, heart arrhythmia, congenital heart disease, valvular heart disease, carditis, aortic aneurysms, peripheral artery disease, thromboembolic disease, and venous thrombosis.

The disclosure provides methods of treating a pulmonary disease in a subject in need thereof by administering an effective amount of the exosomes described herein. The term "pulmonary disease" refers to lung disorders characterized by difficulty breathing, coughing, airway discomfort and inflammation, increased mucus, and/or pulmonary fibrosis. Examples of lung diseases include lung cancer, cystic fibrosis, asthma, chronic obstructive pulmonary disease, bronchitis, emphysema, bronchiectasis, pulmonary edema, pulmonary fibrosis, sarcoidosis, pulmonary hypertension, pneumonia, tuberculosis, interstitial pulmonary fibrosis, interstitial lung disease, acute interstitial pneumonia, respiratory bronchiolitis-associated interstitial lung disease, desquamative interstitial pneumonia, non-specific interstitial pneumonia, idiopathic interstitial pneumonia, bronchiolitis obliterans with organizing pneumonia, restrictive lung disease, or pleurisy.

The disclosure provides methods of treating an inflammatory disease in a subject in need thereof by administering an effective amount of the exosomes described herein. The term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus, myasthenia gravis, juvenile onset diabetes, diabetes mellitus type 1, graft-versus-host disease, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

The disclosure provides methods of treating cancer in a subject in need thereof by administering an effective amount of the exosomes described herein. The term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's Disease, and Non-Hodgkin's lymphoma. Exemplary cancers that may be treated with a compound or method provided herein include cancer of the thyroid, endocrine system, brain, breast, cervix, colon, head and neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The disclosure provides methods of treating an autoimmune disease in a subject in need thereof by administering an effective amount of the exosomes described herein. The term "autoimmune disease" refers to a disease or condition in which a subject's immune system has an aberrant immune response against a substance that does not normally elicit an immune response in a healthy subject. Examples of autoimmune diseases include acute disseminated encephalomyelitis, acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome, autoimmune angioedema, autoimmune aplastic anemia, autoimmune dysautonomia, autoimmune hepatitis, autoimmune hyperlipidemia, autoimmune immunodeficiency, autoimmune inner ear disease, autoimmune myocarditis, autoimmune oophoritis, autoimmune pancreatitis, autoimmune retinopathy, autoimmune thrombocytopenic purpura, autoimmune thyroid disease, autoimmune urticaria, axonal or neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy, chronic recurrent multifocal ostomyelitis, Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura, IgA nephropathy, IgG4-related sclerosing disease, immunoregulatory lipoproteins, inclusion body myositis, interstitial cystitis, juvenile arthritis, type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease, lupus (SLE), Lyme disease, chronic, Meniere's disease, microscopic polyangiitis, mixed connective tissue disease, Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (pediatric autoimmune neuropsychiatric disorders associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis, Susac's syndrome, sympathetic ophthalmia, Takayasu's arteritis, temporal arteritis/giant cell arteritis, thrombocytopenic purpura, Tolosa-Hunt syndrome, transverse myelitis, ulcerative colitis, undifferentiated connective tissue disease, uveitis, vasculitis, vesiculobullous dermatosis, vitiligo, or Wegener's granulomatosis (i.e., granulomatosis with polyangiitis.

The disclosure provides methods of treating an inflammatory disease in a subject in need thereof by administering an effective amount of the exosomes described herein. The term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus, myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

The disclosure provides methods of treating a neurodegenerative disease in a subject in need thereof by administering an effective amount of the exosomes described herein. The term "neurodegenerative disease" refers to a disease or condition in which the function of a subject's nervous system becomes impaired. Examples of neurodegenerative diseases include Alexander's disease, Alper's disease, Alzheimer's disease, amyotrophic lateral sclerosis, ataxia telangiectasia, Batten disease (also known as Spielmeyer-Vogt-Sjogren-Batten disease), bovine spongiform encephalopathy (BSE), Canavan disease, chronic fatigue syndrome, Cockayne syndrome, corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, lewy body dementia, Machado-Joseph disease (spinocerebellar ataxia type 3), multiple sclerosis, multiple system atrophy, myalgic encephalomyelitis, narcolepsy, neuroborreliosis, Parkinson's disease, Pelizaeus-Merzbacher disease, Pick's disease, primary lateral sclerosis, prion diseases, Refsum's disease, Sandhoffs disease, Schilder's disease, subacute combined degeneration of spinal cord secondary to pernicious anaemia, schizophrenia, spinocerebellar ataxia (multiple types with varying characteristics), spinal muscular atrophy, steele-Richardson-Olszewski disease, progressive supranuclear palsy, or tabes dorsalis.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In aspects, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In aspects, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

Dose and Dosing Regimens

The dosage and frequency (single or multiple doses) of the exosomes and pharmaceutical compositions administered to a subject can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and exosomes and pharmaceutical compositions described herein. Adjustment and manipulation of established dosages (e.g., frequency and duration) are within the ability of the skilled artisan.

For any exosomes and pharmaceutical compositions described herein, the effective amount can be initially determined from cell culture assays. Target concentrations will be those concentrations of exosomes that are capable of achieving the methods described herein, as measured using the methods described herein or known in the art. As is known in the art, effective amounts of exosomes for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages of the exosomes and pharmaceutical compositions may be varied depending upon the requirements of the patient. The dose administered to a patient should be sufficient to affect a beneficial therapeutic response in the patient over time. The size of the dose also will be determined by the existence, nature, and extent of any adverse side-effects. Determination of the proper dosage for a particular situation is within the skill of the art. Dosage amounts and intervals can be adjusted individually to provide levels of the exosomes effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical disease or symptoms demonstrated by the particular patient. This planning should involve the careful choice of exosomes by considering factors such as compound potency, relative bioavailability, patient body weight, presence and severity of adverse side effects.

In embodiments, the exosomes or pharmaceutical compositions are administered to a patient at an amount of about 0.001 mg/kg to about 500 mg/kg. In aspects, the exosomes or pharmaceutical compositions are administered to a patient in an amount of about 0.01 mg/kg, 0.1 mg/kg, 0.5 mg/kg, 1 mg/kg, 2 mg/kg, 3 mg/kg, 4 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg, or 300 mg/kg. It is understood that where the amount is referred to as "mg/kg," the amount is milligram per kilogram body weight of the subject being administered with the exosomes or pharmaceutical compositions. In aspects, the exosomes or pharmaceutical compositions are administered to a patient in an amount from about 0.01 mg to about 500 mg per day, as a single dose, or in a dose administered two or three times per day.

Embodiments 1 to 38

Embodiment 1. An exosome comprising a recombinant fusion protein, wherein the recombinant fusion protein comprises an exosome membrane-associated protein and an exogenous target protein.

Embodiment 2. The exosome of Embodiment 1, wherein the fusion protein further comprises at least one peptide linker, an epitope tag, or a combination thereof.

Embodiment 3. The exosome of Embodiment 1 or 2, wherein the exogenous target protein is within an extracellular loop of the exosome membrane-associated protein.

Embodiment 4. The exosome of any one of Embodiments 1 to 3, wherein the exosome membrane-associated protein is CD9, CD37, CD53, CD63, CD68, CD81, CD82, LAMP-1, LAMP-2A, LAMP-2B, LAMP-2C, lactadherin, or PTGFRN.

Embodiment 5. The exosome of Embodiment 4, wherein the exosome membrane-associated protein is CD63, LAMP-2B, or PTGFRN.

Embodiment 6. The exosome of Embodiment 5, wherein the exosome membrane-associated protein is CD63.

Embodiment 7. The exosome of Embodiment 6, wherein the fusion protein comprises the exogenous target protein within extracellular loop 1 of CD63.

Embodiment 8. The exosome of Embodiment 7, wherein extracellular loop 1 of CD63 has an amino acid sequence that is at least 80% identical to SEQ ID NO:14.

Embodiment 9. The exosome of Embodiment 6, wherein the fusion protein comprises the exogenous target protein within extracellular loop 2 of CD63.

Embodiment 10. The exosome of Embodiment 9, wherein extracellular loop 2 of CD63 has an amino acid sequence that is at least 80% identical to SEQ ID NO:15.

Embodiment 11. The exosome of Embodiment 9, wherein extracellular loop 2 of CD63 has an amino acid sequence that is at least 80% identical to SEQ ID NO:16.

Embodiment 12. The exosome of Embodiment 9, wherein extracellular loop 2 of CD63 has an amino acid sequence that is at least 80% identical to SEQ ID NO:17.

Embodiment 13. The exosome of Embodiment 5, wherein the exosome membrane-associated protein is LAMP-2B.

Embodiment 14. The exosome of Embodiment 13, wherein LAMP-2B has an amino acid sequence that is at least 80% identical to SEQ ID NO:18.

Embodiment 15. The exosome of Embodiment 5, wherein the exosome membrane-associated protein is PTGFRN.

Embodiment 16. The exosome of Embodiment 15, wherein PTGFRN has an amino acid sequence that is at least 80% identical to SEQ ID NO:19.

Embodiment 17. The exosome of any one of Embodiments 1 to 3, wherein the exogenous target protein is a single chain variable fragment.

Embodiment 18. The exosome of any one of Embodiments 1 to 17, wherein the exogenous target protein is an anti-HIV single chain variable fragment, an anti-SARS-CoV-2 single chain variable fragment, or an anti-HTLV-1 single chain variable fragment.

Embodiment 19. The exosome of Embodiment 18, wherein the anti-HIV heavy chain variable fragment has an amino acid sequence with at least 80% identity to SEQ ID NO:20; and wherein the anti-HIV light chain variable fragment has an amino acid sequence with at least 80% identity to SEQ ID NO:21.

Embodiment 20. The exosome of Embodiment 18, wherein the anti-SARS-CoV-2 heavy chain variable fragment has an amino acid sequence with at least 80% identity to SEQ ID NO:27; and wherein the anti-SARS-CoV-2 light chain variable fragment has an amino acid sequence with at least 80% identity to SEQ ID NO:28.

Embodiment 21. The exosome of Embodiment 18, wherein the anti-HTLV-1 heavy chain variable fragment has an amino acid sequence with at least 80% identity to SEQ ID NO:25; and wherein the anti-HTLV-1 light chain variable fragment has an amino acid sequence with at least 80% identity to SEQ ID NO:26.

Embodiment 22. The exosome of any one of Embodiments 1 to 16, wherein the exogenous target protein is a cytokine.

Embodiment 23. The exosome of any one of Embodiments 1 to 16, wherein the exogenous target protein is a chemokine.

Embodiment 24. The exosome of any one of Embodiments 1 to 16, wherein the exogenous target protein is an ACE2 peptide, N6 scFv, CR3022 scFv, CCR4 scFv, CCL17 scFv, CCL22, D1D2 domain of CD4, CD4 transmembrane domain, VHH-72 heavy chain, MIP-1-a, SDF-1, IL-8, or a combination of two or more thereof.

Embodiment 25. The exosome of any one of Embodiments 1 to 16, wherein the exogenous target protein is an RNA binding protein.

Embodiment 26. The exosome of Embodiment 25, wherein the RNA binding protein is L7ae, L30e, RBM5, RBM6, RBM7, RMB22, RMB32, RBM41, YBX1, YBX2, CSDE1, PTBP1, ZC3H3, ZC3H15, MATR3, SAMD4A, YTHDC2, CUGBP2, PUM2, RC3H2, ZC3H11A, PARP12, CSDA, SFRS8, EIF4B, U2AF2, SFRS14, SPEN, ELVAL1, THUMPD1, DHX8, SRBD1, PABPC1, DAZAP1, IFG2PB2, ZNF638, SART3, MKRN2, MBNL3, SNRPA, SYNJ2, A2BP1, DDX43, KIAA0020, CNOT4, YTHDC1, PPIE, CHERP, KHSRP, or FUS.

Embodiment 27. An exosome comprising a recombinant fusion protein, wherein the recombinant fusion protein has an amino acid sequence that is at least 80% identical to any one of SEQ ID NOS:1-13.

Embodiment 28. A pharmaceutical composition comprising the exosome of any one of Embodiments 1 to 27 and a pharmaceutically acceptable excipient.

Embodiment 29. A cell comprising the exosome of any one of Embodiments 1 to 27.

Embodiment 30. The cell of Embodiment 29, wherein the cell is a mammalian cell.

Embodiment 31. The cell of Embodiment 29 or 30, wherein the cell is a CD4+ T cell, CD8+ T cell, macrophage, liver sinusoidal endothelial cell, CD34+ hematopoietic stem cell, CD133+ cell, or a stem cell.

Embodiment 32. The cell of Embodiment 31, wherein the stem cell is a hematopoietic stem cell or a mesenchymal stem cell.

Embodiment 33. A method for treating COVID-19 or SARS-CoV-2 in a subject in need thereof, the method comprising administering to the subject an effective amount of the exosome of any one of Embodiments 1 to 27.

Embodiment 34. A method for treating HIV in a subject in need thereof, the method comprising administering to the subject an effective amount of the exosome of any one of Embodiments 1 to 27.

Embodiment 35. A method for treating HTLV-1 in a subject in need thereof, the method comprising administering to the subject an effective amount of the exosome of any one of Embodiments 1 to 27.

Embodiment 36. A method for treating cancer in a subject in need thereof, the method comprising administering to the subject an effective amount of the exosome of any one of Embodiments 1 to 27.

Embodiment 37. A method for treating a disease in a subject in need thereof, the method comprising administering to the subject an effective amount of the exosome of any one of Embodiments 1 to 27.

Embodiment 38. A recombinant fusion protein having an amino acid sequence that is at least 80% identical to any one of SEQ ID NOS:1-13.

Informal Sequence Listing

SEQ ID NO: 1 CD63 Ex1. 1 amino acid sequence with N6-ScFv
CD6 Ex1.1 = capital letters; N6 heavy chain variable fragment = bold, underlined, capital letters;
N6 light chain variable fragment = underlined capital letters; Peptide linker = lower case letters.
MAVEGGMKCVKFLLYVLLLAFCACAVGLIAVGVGAQLVLgggsgggsgggsgggsRAHLVQ
SGTAMKKPGASVRVSCQTSGYTFTAHILFWFRQAPGRGLEWVGWIKPQYGAVNF
GGGFRDRVTLTRDVYREIAYMDIRGLKPDDTAVYYCARDRSYGDSSWALDAWGQ
GTTVVVSAgggsgggsgggsgggsYIHVTQSPSSLSVSIGDRVTINCQTSQGVGSDLHWYQHK
PGRAPKLLIHHTSSVEDGVPSRFSGSGFHTSFNLTISDLQADDIATYYCQVLQFFGRGSRL
HIKgggsgggsgggsgggsIIQGATPGSLLPVVIIAVGVFLFLVAFVGCCGACKENYCLMITFAIF
LSLIMLVEVAAAIAGYVFRDKVMSEFNNNFRQQMENYPKNNHTASILDRMQADFKCC
GAANYTDWEKIPSMSKNRVPDSCCINVTVGCGINFNEKAIHKEGCVEKIGGWLRKNVL
VVAAAALGIAFVEVLGIVFACCLVKSIRSGYEVM SEQ ID NO: 2 CD63 Ex2.2 amino acid sequence with N6 ScFv
CD6 Ex2.2 = capital letters; N6 heavy chain variable fragment = bold, underlined, capital letters;
N6 light chain variable fragment = underlined capital letters; Peptide linker = lower case letters.
MAVEGGMKCVKFLLYVLLLAFCACAVGLIAVGVGAQLVLSQTIIQGATPGSLLPVVIIA
VGVFLFLVAFVGCCGACKENYCLMITFAIFLSLIMLVEVAAAIAGYVFRDKVMSEFNNN
FRQQMENYPKNNHTASILDRMQADFKCCGgggsgggsgggsgggsRAHLVQSGTAMKKPG
ASVRVSCQTSGYTFTAHILFWFRQAPGRGLEWVGWIKPQYGAVNFGGGFRDRVT
LTRDVYREIAYMDIRGLKPDDTAVYYCARDRSYGDSSWALDAWGQGTTVVVSAgg
gsgggsgggsgggsYIHVTQSPSSLSVSIGDRVTINCQTSQGVGSDLHWYQHKPGRAPKLLIHH
TSSVEDGVPSRFSGSGFHTSFNLTISDLQADDIATYYCQVLQFFGRGSRLHIKgggsgggsgg
gsgggsGCVEKIGGWLRKNVLVVAAAALGIAFVEVLGIVFACCLVKSIRSGYEVM SEQ ID NO: 3 CD63 Ex2.3 amino acid sequence with N6 ScFv
CD6 Ex2.3 = capital letters; N6 heavy chain variable fragment = bold, underlined, capital letters;
N6 light chain variable fragment = underlined capital letters; Peptide linker = lower case letters.
MAVEGGMKCVKFLLYVLLLAFCACAVGLIAVGVGAQLVLSQTIIQGATPGSLLPVVIIA
VGVFLFLVAFVGCCGACKENYCLMITFAIFLSLIMLVEVAAAIAGYVFRDKVMSEFNNN
FRQQMENYPKNNHTASILDRMQADFKCCGgggsgggsgggsgggsRAHLVQSGTAMKKPG
ASVRVSCQTSGYTFTAHILFWFRQAPGRGLEWVGWIKPQYGAVNFGGGFRDRVT
LTRDVYREIAYMDIRGLKPDDTAVYYCARDRSYGDSSWALDAWGOGTTVVVSAgg
gsgggsgggsgggsYIHVTQSPSSLSVSIGDRVTINCQTSQGVGSDLHWYQHKPGRAPKLLIHH
TSSVEDGVPSRFSGSGFHTSFNLTISDLQADDIATYYCQVLQFFGRGSRLHIKgggsgggsgg
gsgggsCCINVTVGCGINFNEKAIHKEGCVEKIGGWLRKNVLVVAAAALGIAFVEVLGIVF
ACCLVKSIRSGYEVM SEQ ID NO: 4 CD63 Ex2.4 amino acid sequence with N6 ScFv
CD6 Ex2.4 = capital letters; N6 heavy chain variable fragment = bold, underlined, capital letters;
N6 light chain variable fragment = underlined capital letters; Peptide linker = lower case letters.
MAVEGGMKCVKFLLYVLLLAFCACAVGLIAVGVGAQLVLSQTIIQGATPGSLLPVVIIA
VGVFLFLVAFVGCCGACKENYCLMITFAIFLSLIMLVEVAAAIAGYVFRDKVMSEFNNN
FRQQMENYPKNNHTASILDRMQADFKCCGAANYTDWEKIPSMSKNRVPDSCCgggsggg
sgggsgggsRAHLVQSGTAMKKPGASVRVSCQTSGYTFTAHILFWFRQAPGRGLEWV
GWIKPQYGAVNFGGGFRDRVTLTRDVYREIAYMDIRGLKPDDTAVYYCARDRSY
GDSSWALDAWGQGTTVVVSAgggsgggsgggsgggsYIHVTQSPSSLSVSIGDRVTINCQSTQ
GVGSDLHWYQHKPGRAPKLLIHHTSSVEDGVPSRFSGSGFHTSFNLTISDLQADDIATY
YCQVLQFFGRGSRLHIKgggsgggsgggsgggsGCVEKIGGWLRKNVLVVAAAALGIAFVEVL
GIVFACCLVKSIRSGYEVM SEQ ID NO: 5 tCD4(D1D2)-CD63 amino acid sequence
CD63 = capital letters; CD4 D1D2 domain = bold, underlined, capital letters; CD4
transmembrane domain = underlined capital letters; Peptide linker = lower case letters.
MVRGVPFRHLLLVLQLALLPAATQGKKVVLGKKGDTVELTCTASQKKSIQFHWK
NSNQIKILGNQGSFLTKGPSKLNDRADSRRSLWDQGNFPLIIKNLKIEDSDTYICEVE
DQKEEVQLLVFGLTANSDTHLLQGQSLTLTLESPPGSSPSVQCRSPRGKNIQGGKT
LSVSQLELQDSGTWTCTVLQNQKKVEFKIDIVVLAFQKASggggsggggsMALIVLGGV
AGLLLFIGLGIFFggggsMAVEGGMKCVKFLLYVLLLAFCACAVGLIAVGVGAQLVLSQT
IIQGATPGSLLPVVIIAVGVFLFLVAFVGCCGACKENYCLMITFAIFLSLIMLVEVAAAIA -continued Informal Sequence Listing GYVFRDKVMSEFNNNFRQQMENYPKNNHTASILDRMQADFKCCGAANYTDWEKIPS
MSKNRVPDSCCINVTVGCGINFNEKAIHKEGCVEKIGGWLRKNVLVVAAAALGIAFVE
VLGIVFACCLVKSIRSGYEVM SEQ ID NO: 6 Lamp2b-N6 version 1 amino acid sequence
Lamp2b = capital letters; N6 heavy chain variable fragment = bold, underlined, capital letters;
N6 light chain variable fragment = underlined capital letters; Peptide linker = lower case letters.
HA tag = lower case underlined letters.
MVCFRLFPVPGSGLVLVCLVLGAVRSYAGNSTMgsgRAHLVQSGTAMKKPGASVRVS
CQTSGYTFTAHILFWFRQAPGRGLEWVGWIKPQYGAVNFGGGFRDRVTLTRDVY
REIAYMDIRGLKPDDTAVYYCARDRSYGDSSWALDAWGQGTTVVVSAgggsgggsggg
sgggsYIHVTQSPSSLSVSIGDRVTINCQTSQGVGSDLHWYQHKPGRAPKLLIHHTSSVED
GVPSRFSGSGFHTSFNLTISDLQADDIATYYCQVLQFFGRGSRLHIKgsgsgsgGSSLELNLT
DSENATCLYAKWQMNFTVRYETTNKTYKTVTISDHGTVTYNGSICGDDQNGPKIAVQF
GPGFSWIANFTKAASTYSIDSVSFSYNTGDNTTFPDAEDKGILTVDELLAIRIPLNDLFRC
NSLSTLEKNDVVQHYWDVLVQAFVQNGTVSTNEFLCDKDKTSTVAPTIHTTVPSPTTTP
TPKEKPEAGTYSVNNGNDTCLLATMGLQLNITQDKVASVININPNTTHSTGSCRSHTAL
LRLNSSTIKYLDFVFAVKNENRFYLKEVNISMYLVNGSVFSIANNNLSYWDAPLGSSYM
CNKEQTVSVSGAFQINTFDLRVQPFNVTQGKYSTAQECSLDDDTILIPIIVGAGLSGLIIVI
VIAYVIGRRKSYAGYQTLgsgypydvpdya SEQ ID NO: 7 Lamp2b-N6 version 2 amino acid sequence
Lamp2b = capital letters; N6 heavy chain variable fragment = bold, underlined, capital letters;
N6 light chain variable fragment = underlined capital letters; IgG = bold capital letters; Peptide
linker = lower case letters; HA tag = lower case underlined letters.
MVCFRLFPVPGSGLVLVCLVLGAVRSYAGNSTMgsgRAHLVQSGTAMKKPGASVRVS
CQTSGYTFTAHILFWFRQAPGRGLEWVGWIKPQYGAVNFGGGFRDRVTLTRDVY
REIAYMDIRGLKPDDTAVYYCARDRSYGDSSWALDAWGQGTTVVVSAgggsgggsggg
sgggsYIHVTQSPSSLSVSIGDRVTINCQTSQGVGSDLHWYQHKPGRAPKLLIHHTSSVED
GVPSRFSGSGFHTSFNLTISDLQADDIATYYCQVLQFFGRGSRLHIKESKYGPPCPPCPA
PEFEGGPSVFLFPPKPKDTLMISRTPEVTCVVVDVSQEDPEVQFNWYVDGVEVHNA
KTKPREEQFQSTYRVVSVLTVLHQDWLNGKEYKCKVSNKGLPSSIEKTISKAKGQ
PREPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLGKTILIPIIVG
AGLSGLIIVIVIAYVIGRRKSYAGYQTLgsgypydvpdya SEQ ID NO: 8 PTGFRN-N6 version 1 amino acid sequence
Lamp2b = capital letters; N6 heavy chain variable fragment = bold, underlined, capital letters;
N6 light chain variable fragment = underlined capital letters; Peptide linker = lower case letters;
HA tag = lower case underlined letters.
MGRLASRPLLLALLSLALCRGRVVRgsgRAHLVQSGTAMKKPGASVRVSCQTSGYTF
TAHILFWFRQAPGRGLEWVGWIKPQYGAVNFGGGFRDRVTLTRDVYREIAYMDI
RGLKPDDTAVYYCARDRSYGDSSWALDAWGQGTTVVVSAgsdsnaghasagntsYIHVTQ
SPSSLSVSIGDRVTINCQTSQGVGSDLHWYQHKPGRAPKLLIHHTSSVEDGVPSRFSGSG
FHTSFNLTISDLQADDIATYYCQVLQFFGRGSRLHIKgsgsgsgVPTATLVRVVGTELVIPC
NVSDYDGPSEQNFDWSFSSLGSSFVELASTWEVGFPAQLYQERLQRGEILLRRTANDAV
ELHIKNVQPSDQGHYKCSTPSTDATVQGNYEDTVQVKVLADSLHVGPSARPPPSLSLRE
GEPFELRCTAASASPLHTHLALLWEVHRGPARRSVLALTHEGRFHPGLGYEQRYHSGD
VRLDTVGSDAYRLSVSRALSADQGSYRCIVSEWIAEQGNWQEIQEKAVEVATVVIQPSV
LRAAVPKNVSVAEGKELDLTCNITTDRADDVRPEVTWSFSRMPDSTLPGSRVLARLDR
DSLVHSSPHVALSHVDARSYHLLVRDVSKENSGYYYCHVSLWAPGHNRSWHKVAEAV
SSPAGVGVTWLEPDYQVYLNASKVPGFADDPTELACRVVDTKSGEANVRFTVSWYYR
MNRRSDNVVTSELLAVMDGDWTLKYGERSKQRAQDGDFIFSKEHTDTFNFRIQRTTEE
DRGNYYCVVSAWTKQRNNSWVKSKDVFSKPVNIFWALEDSVLVVKARQPKPFFAAGN
TFEMTCKVSSKNIKSPRYSVLIMAEKPVGDLSSPNETKYIISLDQDSVVKLENWTDASRV
DGVVLEKVQEDEFRYRMYQTQVSDAGLYRCMVTAWSPVRGSLWREAATSLSNPIEIDF
QTSGPIFNASVHSDTPSVIRGDLIKLFCIITVEGAALDPDDMAFDVSWFAVHSFGLDKAP
VLLSSLDRKGIVTTSRRDWKSDLSLERVSVLEFLLQVHGSEDQDFGNYYCSVTPWVKSP
TGSWQKEAEIHSKPVFITVKMDVLNAFKYPLLIGVGLSTVIGLLSCLIGYCSSHWCCKKE
VQETRRERRRLMSMEMDypydvpdya SEQ ID NO: 9 PTGFRN-N6 version 2 amino acid sequence
Lamp2b = capital letters; N6 heavy chain variable fragment = bold, underlined, capital letters;
N6 light chain variable fragment = underlined capital letters; IgG = bold capital letters; Peptide
linker = lower case letters; HA tag = lower case underlined letters.
MGRLASRPLLLALLSLALCRGRVVRgsgRAHLVQSGTAMKKPGASVRVSCQTSGYTF
TAHILFWFRQAPGRGLEWVGWIKPQYGAVNFGGGFRDRVTLTRDVYREIAYMDI
RGLKPDDTAVYYCARDRSYGDSSWALDAWGQGTTVVVSAgsdsnaghasagntsYIHVTQ
SPSSLSVSIGDRVTINCQTSQGVGSDLHWYQHKPGRAPKLLIHHTSSVEDGVPSRFSGSG
FHTSFNLTISDLQADDIATYYCQVLQFFGRGSRLHIKESKYGPPCPPCPAPEFEGGPSVF
LFPPKPKDTLMISRTPEVTCVVVDVSQEDPEVQFNWYVDGVEVHNAKTKPREEQF
QSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDGSFFLYS
RLTVDKSRWQEGNVFSCSVMHEALHNHYTQKSLSLSLGKLLIGVGLSTVIGLLSCLI
GYCSSHWCCKKEVQETRRERRRLMSMEMDypydvpdya -continued

| Informal Sequence Listing |
|---|

SEQ ID NO: 10 CD63-CCR4-ScFv Ex2.4 amino acid sequence
CD63 = capital letters; CCR4 heavy chain variable fragment = bold, underlined, capital letters; CCR4 light chain variable fragment = underlined capital letters; Peptide linker = lower case letters.
MAVEGGMKCVKFLLYVLLLAFCACAVGLIAVGVGAQLVLSQTIIQGATPGSLLPVVIIA
VGVFLFLVAFVGCCGACKENYCLMITFAIFLSLIMLVEVAAAIAGYVFRDKVMSEFNNN
FRQQMENYPKNNHTASILDRMQADFKCCGAANYTDWEKIPSMSKNRVPDSCCgggsggg
sgggsgggsEVQLVESGGDLVQPGRSLRLSCAASGFIFSNYGMSWVRQAPGKGLEWVA
TISSASTYSYYPDSVKGRFTISRDNAKNSLYLQMNSLRVEDTALYYCGRHSDGNFAF
GYWGQGTLVTVSSgggsgggsgggsgggsDVLMTQSPLSLPVTPGEPASISCRSSRNIVHINGD
TYLEWYLQKPGQSPQLLIYKVSNRFSGVPDRFSGSGSGTDFTLKISRVEAEDVGVYYCF
QGSLLPWTFGQGTKVEIKgggsgggsgggsgggsGCVEKIGGWLRKNVLVVAAAALGIAFVE
VLGIVFACCLVKSIRSGYEVM SEQ ID NO: 11 CD63-CR3022-ScFv Ex2.4 amino acid sequence
CD63 = capital letters; CR3022 heavy chain variable fragment = bold, underlined, capital letters; CR3022 light chain variable fragment = underlined capital letters; Peptide linker = lower case letters.
MAVEGGMKCVKFLLYVLLLAFCACAVGLIAVGVGAQLVLSQTIIQGATPGSLLPVVIIA
VGVFLFLVAFVGCCGACKENYCLMITFAIFLSLIMLVEVAAAIAGYVFRDKVMSEFNNN
FRQQMENYPKNNHTASILDRMQADFKCCGAANYTDWEKIPSMSKNRVPDSCCgggsggg
sgggsgggsQMQLVQSGTEVKKPGESLKISCKGSGYGFITYWIGWVRQMPGKGLEW
MGIIYPGDSETRYSPSFQGQVTISADKSINTAYLQWSSLKASDTAIYYCAGGSGISTP
MDVWGQGTTVTVgsdsnaghasagntsDIQLTQSPDSLAVSLGERATINCKSSQSVLYSSINK
NYLAWYQQKPGQPPKLLIYWASTRESGVPDRFSGSGSGTDFTLTISSLQAEDVAVYYCQ
QYYSTPYTFGQGTKVEIKgggsgggsgggsgggsGCVEKIGGWLRKNVLVVAAAALGIAFVEV
LGIVFACCLVKSIRSGYEVM SEQ ID NO: 12 CD63-VHH72-VHH-72 Ex2.4 amino acid sequence
CD63 = capital letters; VHH-72 heavy chain variable fragment = bold, underlined, capital letters; Peptide linker = lower case letters.
MAVEGGMKCVKFLLYVLLLAFCACAVGLIAVGVGAQLVLSQTIIQGATPGSLLPVVIIA
VGVFLFLVAFVGCCGACKENYCLMITFAIFLSLIMLVEVAAAIAGYVFRDKVMSEFNNN
FRQQMENYPKNNHTASILDRMQADFKCCGAANYTDWEKIPSMSKNRVPDSCCgggsggg
sgggsgggsQVQLQESGGGLVQAGGSLRLSCAASGRTFSEYAMGWFRQAPGKEREFV
ATISWSGGSTYYTDSVKGRFTISRDNAKNTVYLQMNSLKPDDTAVYYCAAAGLGT
VVSEWDYDYDYWGQGTQVTVSSgggsgggsgggsgggsQVQLQESGGGLVQAGGSLRLS
CAASGRTFSEYAMGWFRQAPGKEREFVATISWSGGSTYYTDSVKGRFTISRDNAK
NTVYLQMNSLKPDDTAVYYCAAAGLGTVVSEWDYDYDYWGQGTQVTVSSgggsggg
sgggsgggsGCVEKIGGWLRKNVLVVAAAALGIAFVEVLGIVFACCLVKSIRSGYEVM SEQ ID NO: 13 CD63-ACE2-peptide Ex2.4 amino acid sequence
CD63 = capital letters; ACE2 peptide = bold, underlined capital letters.
MAVEGGMKCVKFLLYVLLLAFCACAVGLIAVGVGAQLVLSQTIIQGATPGSLLPVVIIA
VGVFLFLVAFVGCCGACKENYCLMITFAIFLSLIMLVEVAAAIAGYVFRDKVMSEFNNN
FRQQMENYPKNNHTASILDRMQADFKCCGAANYTDWEKIPSMSKNRVPDSCCIEEQA
KTFLDKFNHEAEDLFYQSGCVEKIGGWLRKNVLVVAAAALGIAFVEVLGIVFACCLV
KSIRSGYEVM AMINO ACID SEQUENCES OF EXOSOME MEMBRANE PROTEINS
SEQ ID NO: 14 CD63 Ex1.1 amino acid sequence
MAVEGGMKCVKFLLYVLLLAFCACAVGLIAVGVGAQLVLIIQGATPGSLLPVVIIAVGV
FLFLVAFVGCCGACKENYCLMITFAIFLSLIMLVEVAAAIAGYVFRDKVMSEFNNNFRQ
QMENYPKNNHTASILDRMQADFKCCGAANYTDWEKIPSMSKNRVPDSCCINVTVGCGI
NFNEKAIHKEGCVEKIGGWLRKNVLVVAAAALGIAFVEVLGIVFACCLVKSIRSGYEV
M SEQ ID NO: 15 CD63 Ex2.2 amino acid sequence
MAVEGGMKCVKFLLYVLLLAFCACAVGLIAVGVGAQLVLSQTIIQGATPGSLLPVVIIA
VGVFLFLVAFVGCCGACKENYCLMITFAIFLSLIMLVEVAAAIAGYVFRDKVMSEFNNN
FRQQMENYPKNNHTASILDRMQADFKCCGGCVEKIGGWLRKNVLVVAAAALGIAFVE
VLGIVFACCLVKSIRSGYEVM SEQ ID NO: 16 CD63 Ex2.3 amino acid sequence
MAVEGGMKCVKFLLYVLLLAFCACAVGLIAVGVGAQLVLSQTIIQGATPGSLLPVVIIA
VGVFLFLVAFVGCCGACKENYCLMITFAIFLSLIMLVEVAAAIAGYVFRDKVMSEFNNN
FRQQMENYPKNNHTASILDRMQADFKCCGCCINVTVGCGINFNEKAIHKEGCVEKIGG
WLRKNVLVVAAAALGIAFVEVLGIVFACCLVKSIRSGYEVM SEQ ID NO: 17 CD63 Ex2.4 amino acid sequence
MAVEGGMKCVKFLLYVLLLAFCACAVGLIAVGVGAQLVLSQTIIQGATPGSLLPVVIIA
VGVFLFLVAFVGCCGACKENYCLMITFAIFLSLIMLVEVAAAIAGYVFRDKVMSEFNNN
FRQQMENYPKNNHTASILDRMQADFKCCGAANYTDWEKIPSMSKNRVPDSCCGCVEK
IGGWLRKNVLVVAAAALGIAFVEVLGIVFACCLVKSIRSGYEVM -continued Informal Sequence Listing SEQ ID NO: 18 Lamp2b amino acid sequence
MVCFRLFPVPGSGLVLVCLVLGAVRSYAGNSTMGSSLELNLTDSENATCLYAKWQMN
FTVRYETTNKTYKTVTISDHGTVTYNGSICGDDQNGPKIAVQFGPGFSWIANFTKAAST
YSIDSVSFSYNTGDNTTFPDAEDKGILTVDELLAIRIPLNDLFRCNSLSTLEKNDVVQHY
WDVLVQAFVQNGTVSTNEFLCDKDKTSTVAPTIHTTVPSPTTTPTPKEKPEAGTYSVNN
GNDTCLLATMGLQLNITQDKVASVININPNTTHSTGSCRSHTALLRLNSSTIKYLDFVFA
VKNENRFYLKEVNISMYLVNGSVFSIANNNLSYWDAPLGSSYMCNKEQTVSVSGAFQI
NTFDLRVQPFNVTQGKYSTAQECSLDDDTILIPIIVGAGLSGLIIVIVIAYVIGRRKSYAGY
QTL SEQ ID NO: 19 PTGFRN amino acid sequence
MGRLASRPLLLALLSLALCRGRVVRVPTATLVRVVGTELVIPCNVSDYDGPSEQNFDW
SFSSLGSSFVELASTWEVGFPAQLYQERLQRGEILLRRTANDAVELHIKNVQPSDQGHY
KCSTPSTDATVQGNYEDTVQVKVLADSLHVGPSARPPPSLSLREGEPFELRCTAASASPL
HTHLALLWEVHRGPARRSVLALTHEGRFHPGLGYEQRYHSGDVRLDTVGSDAYRLSV
SRALSADQGSYRCIVSEWIAEQGNWQEIQEKAVEVATVVIQPSVLRAAVPKNVSVAEG
KELDLTCNITTDRADDVRPEVTWSFSRMPDSTLPGSRVLARLDRDSLVHSSPHVALSHV
DARSYHLLVRDVSKENSGYYYCHVSLWAPGHNRSWHKVAEAVSSPAGVGVTWLEPD
YQVYLNASKVPGFADDPTELACRVVDTKSGEANVRFTVSWYYRMNRRSDNVVTSELL
AVMDGDWTLKYGERSKQRAQDGDFIFSKEHTDTFNFRIQRTTEEDRGNYYCVVSAWT
KQRNNSWVKSKDVFSKPVNIFWALEDSVLVVKARQPKPFFAAGNTFEMTCKVSSKNIK
SPRYSVLIMAEKPVGDLSSPNETKYIISLDQDSVVKLENWTDASRVDGVVLEKVQEDEF
RYRMYQTQVSDAGLYRCMVTAWSPVRGSLWREAATSLSNPIEIDFQTSGPIFNASVHSD
TPSVIRGDLIKLFCIITVEGAALDPDDMAFDVSWFAVHSFGLDKAPVLLSSLDRKGIVTT
SRRDWKSDLSLERVSVLEFLLQVHGSEDQDFGNYYCSVTPWVKSPTGSWQKEAEIHSK
PVFITVKMDVLNAFKYPLLIGVGLSTVIGLLSCLIGYCSSHWCCKKEVQETRRERRRLMS
MEMD AMINO ACID SEQUENCES OF TARGET PROTEINS
SEQ ID NO: 20 N6 heavy chain variable fragment
RAHLVQSGTAMKKPGASVRVSCQTSGYTFTAHILFWFRQAPGRGLEWVGWIKPQYGA
VNFGGGFRDRVTLTRDVYREIAYMDIRGLKPDDTAVYYCARDRSYGDSSWALDAWGQ
GTTVVVSA SEQ ID NO: 21 N6 light chain variable fragment
YIHVTQSPSSLSVSIGDRVTINCQTSQGVGSDLHWYQHKPGRAPKLLIHHTSSVEDGVPS
RFSGSGFHTSFNLTISDLQADDIATYYCQVLQFFGRGSRLHIK SEQ ID NO: 22 D1D2 CD4
MVRGVPFRHLLLVLQLALLPAATQGKKVVLGKKGDTVELTCTASQKKSIQFHWKNSN
QIKILGNQGSFLTKGPSKLNDRADSRRSLWDQGNFPLIIKNLKIEDSDTYICEVEDQKEEV
QLLVFGLTANSDTHLLQGQSLTLTLESPPGSSPSVQCRSPRGKNIQGGKTLSVSQLELQD
SGTWTCTVLQNQKKVEFKIDIVVLAFQKAS SEQ ID NO: 23 CD4 Transmembrane Domain
MALIVLGGVAGLLLFIGLGIFF SEQ ID NO: 24 IgG
ESKYGPPCPPCPAPEFEGGPSVFLFPPKPKDTLMISRTPEVTCVVVDVSQEDPEVQFNWY
VDGVEVHNAKTKPREEQFQSTYRVVSVLTVLHQDWLNGKEYKCKVSNKGLPSSIEKTI
SKAKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSLGK SEQ ID NO: 25 CCR4 heavy chain variable fragment
EVQLVESGGDLVQPGRSLRLSCAASGFIFSNYGMSWVRQAPGKGLEWVATISSASTYSY
YPDSVKGRFTISRDNAKNSLYLQMNSLRVEDTALYYCGRHSDGNFAFGYWGQGTLVT
VSS SEQ ID NO: 26 CCR4 light chain variable fragment
DVLMTQSPLSLPVTPGEPASISCRSSRNIVHINGDTYLEWYLQKPGQSPQLLIYKVSNRFS
GVPDRFSGSGSGTDFTLKISRVEAEDVGVYYCFQGSLLPWTFGQGTKVEIK SEQ ID NO: 27 CR3022 heavy chain variable fragment
QMQLVQSGTEVKKPGESLKISCKGSGYGFITYWIGWVRQMPGKGLEWMGIIYPGDSET
RYSPSFQGQVTISADKSINTAYLQWSSLKASDTAIYYCAGGSGISTPMDVWGQGTTVTV SEQ ID NO: 28 CR3022 light chain variable fragment
DIQLTQSPDSLAVSLGERATINCKSSQSVLYSSINKNYLAWYQQKPGQPPKLLIYWASTR
ESGVPDRFSGSGSGTDFTLTISSLQAEDVAVYYCQQYYSTPYTFGQGTKVEIK SEQ ID NO: 29 VHH72 heavy chain variable fragment
QVQLQESGGGLVQAGGSLRLSCAASGRTFSEYAMGWFRQAPGKEREFVATISWSGGST
YYTDSVKGRFTISRDNAKNTVYLQMNSLKPDDTAVYYCAAAGLGTVVSEWDYDYDY
WGQGTQVTVSS -continued

| Informal Sequence Listing |
| --- |
| SEQ ID NO: 30 ACE2 Peptide<br>IEEQAKTFLDKFNHEAEDLFYQS |
| PEPTIDE LINKERS<br>SEQ ID NO: 31<br>GGGSGGGSGGGSGGGS |
| SEQ ID NO: 32<br>GGGGSGGGGS |
| SEQ ID NO: 33<br>GGGGS |
| SEQ ID NO: 34<br>GSG |
| SEQ ID NO: 35<br>GSGSGSG |
| SEQ ID NO: 36<br>GSDSNAGHASAGNTS |
| HA Tag<br>SEQ ID NO: 37<br>YPYDVPDYA |

EXAMPLES

The following examples are for purposes of illustration only and are not intended to limit the spirit or scope of the disclosure or claims.

Exosomes can be taken up by cells in a non-specific manner, but they generally have a predilection for being taking up by cells similar to their origin. One means to skew exosome uptake to particular cell types is by embedding specific receptor agonists or a single-chain fragment variable (ScFv) into the extracellular membrane of the CD63 exosome-associated protein. The inventors developed a method to convert cell expressed exosomes into receptor targeted exosomes. Three approaches are being developed, whereby any antibody-derived scFvs, or receptor targeted peptides (for instance to embed Dynorphin to target the D1 receptor or Enkephalin to target the D2 dopaminergic receptors in neurons), cytokines or chemokines (for targeting cell specific chemokine or cytokine receptors) is embedded into the exosome-enriched membrane receptor proteins, such as CD63, Lamp2b, or PTGFRN.

Example 1

Figure 1B:
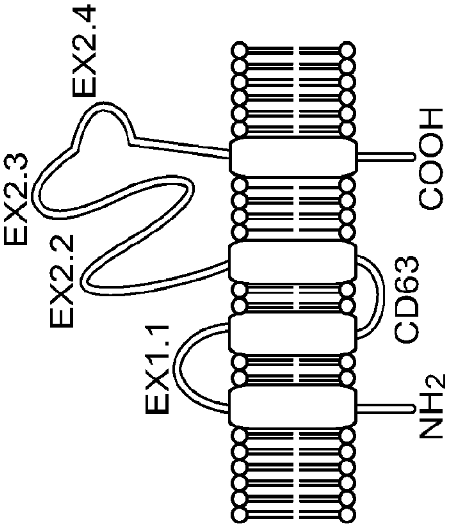
Figure 2:
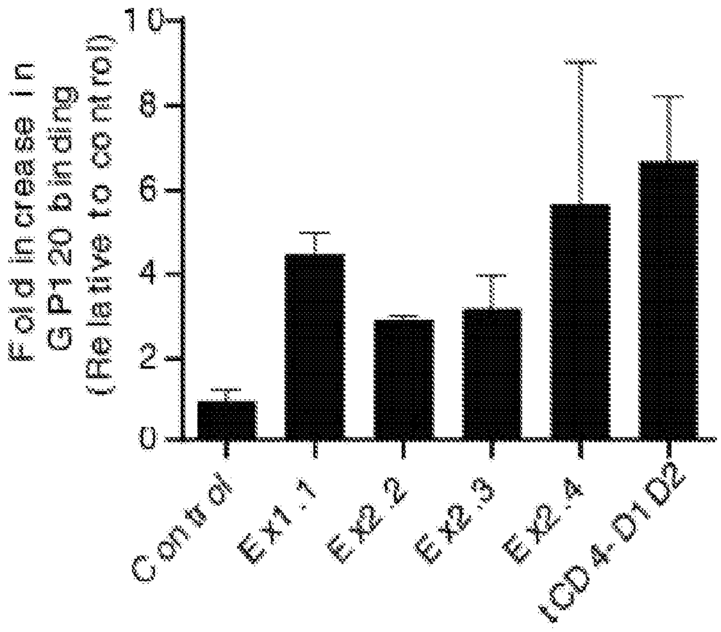
FIG. 2. N6-CD63 exosomes can bind gp120 coated beads. Exosomes were purified from 293HEK cell supernatant following transfection with vectors expressing the N6 ScFv incorporated into various external loops (Ex1.1-2.4) or the control truncated CD4 containing domain 1 and 2 (tCD4-D1D2) fused to the N-terminus of CD63. The control is a vector expressing CD63. Aldehyde/Sulfate latex beads were coated with recombinant HIV gp120 and then mixed with purified exosomes stained with a fluorescent dye. The beads were washed, and bound exosomes determined by flow cytometry. These data are presented as percentage positive signal relative to the CD63 control. Error bars represent SEM from triplicate experiments.
Figure 3A:
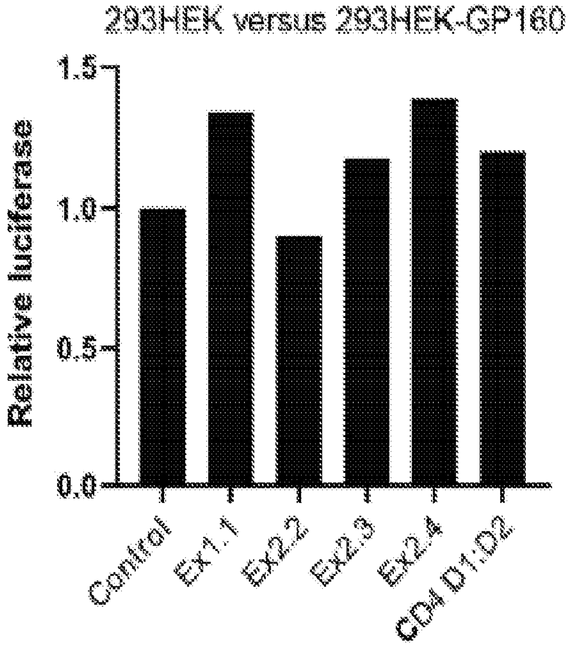
FIGS. 3A-3B show uptake of N6-CD63 exosomes in GP160 expressing cells.
Figure 3B:
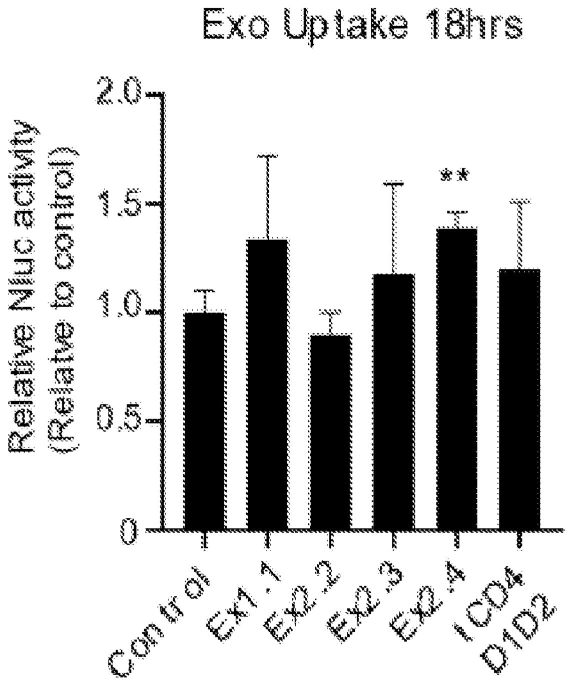
Figure 4A:
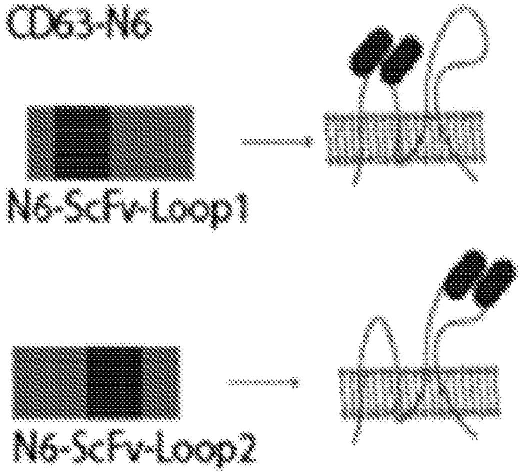
FIGS. 4A-4C are schematics depicting the three approaches developed to target exosomes to specific receptor bearing cells. Examples are depicted to contain the broadly neutralizing anti-HIV ScFv (N6) fused to various exosome-associated membrane and transmembrane spanning proteins, CD63, Lamp2b and PTGFRN. Note that any receptor targeted ScFv could be utilized in place of N6.
Figure 4B:
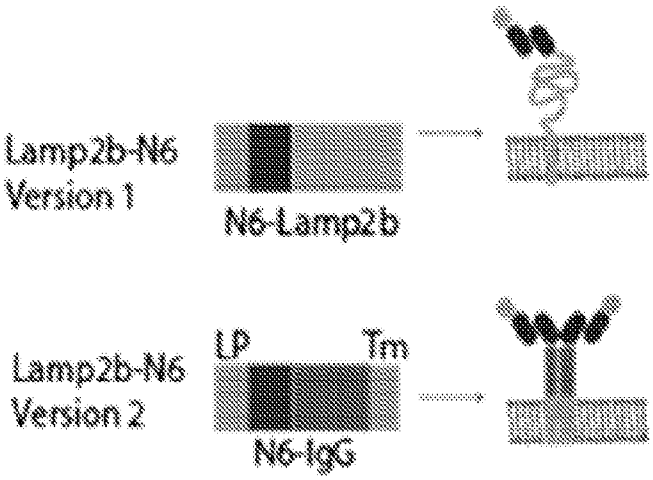
Figure 4C:
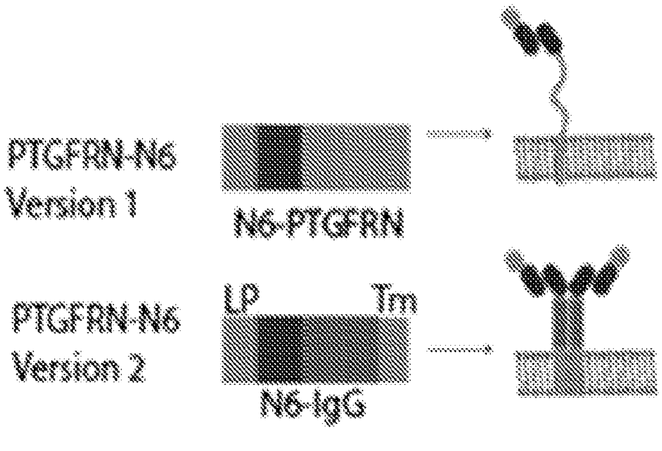
Figure 5A:
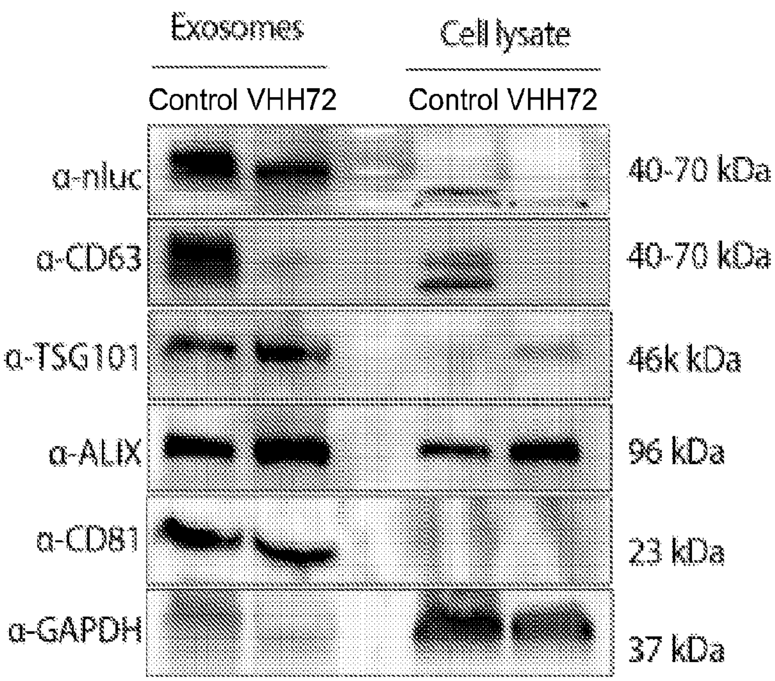
FIGS. 5A-5D are a characterization of VHH72-CD63 exosomes.
Figure 5B:
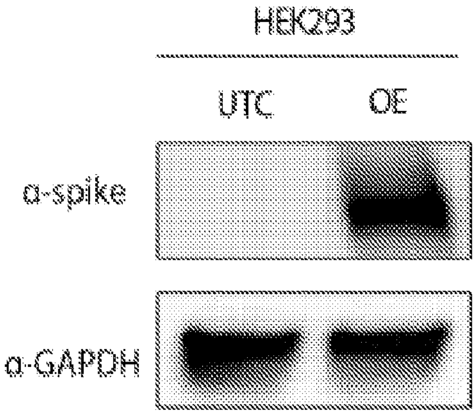
Figure 5C:
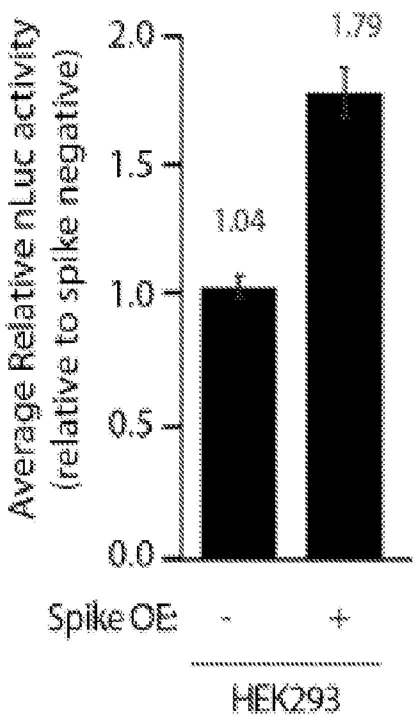
Figure 5D:
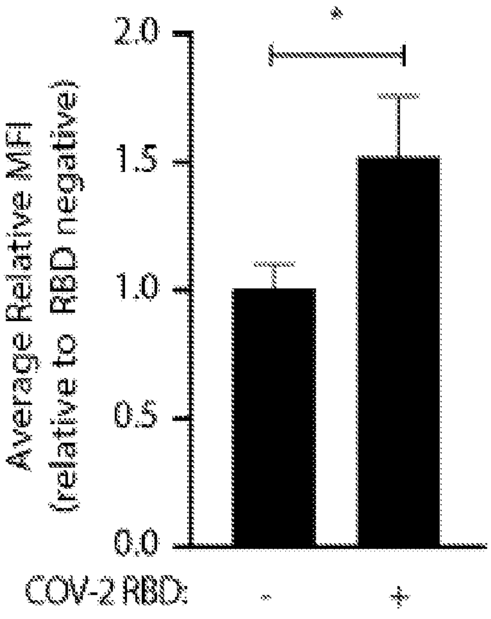
Figure 6A:
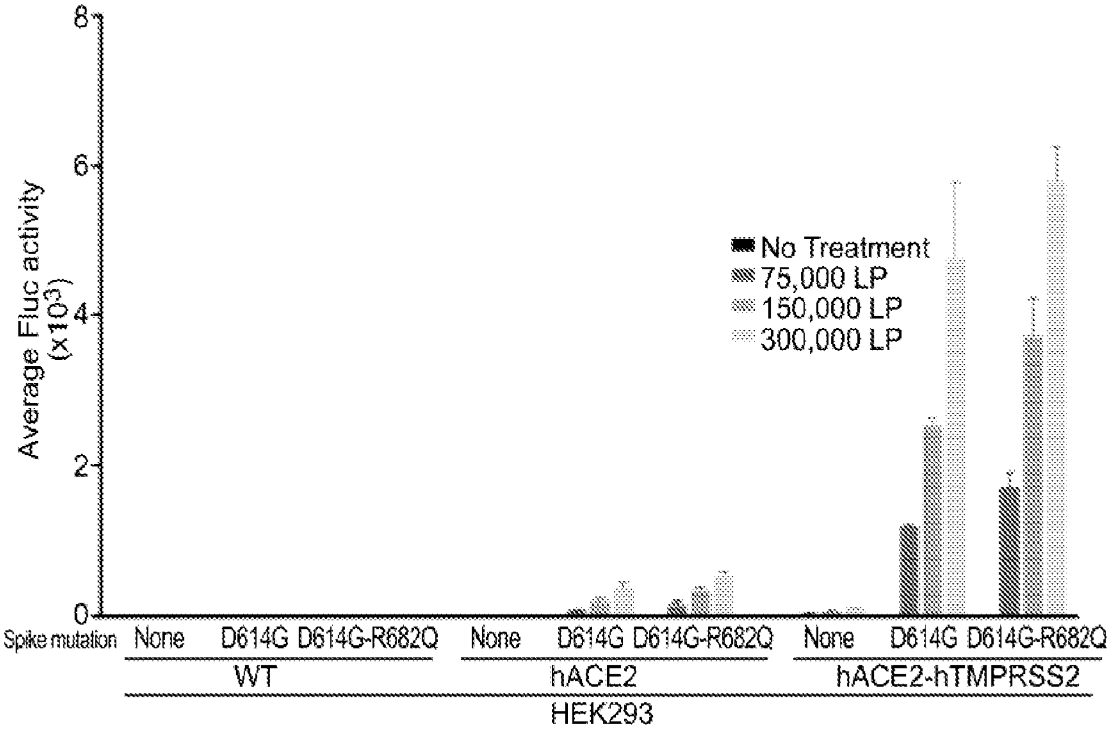
FIGS. 6A-6C: VHH72-CD62 exosomes neutralize pseudotyped spike lentiviral particles.
Figure 6B:
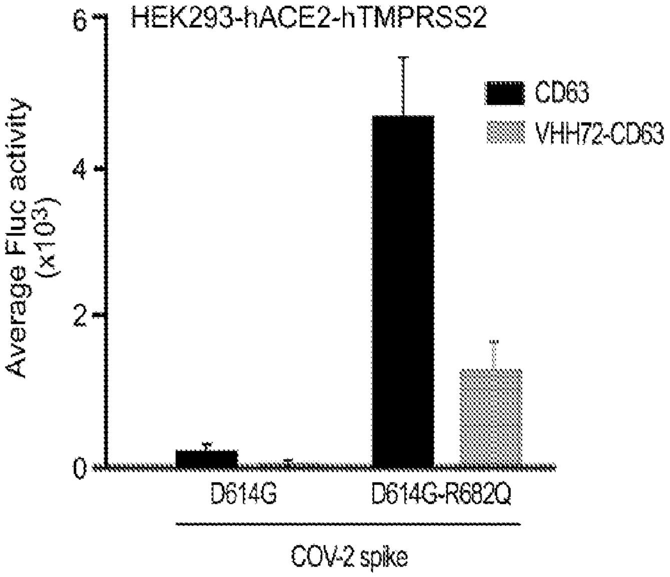
Figure 6C:
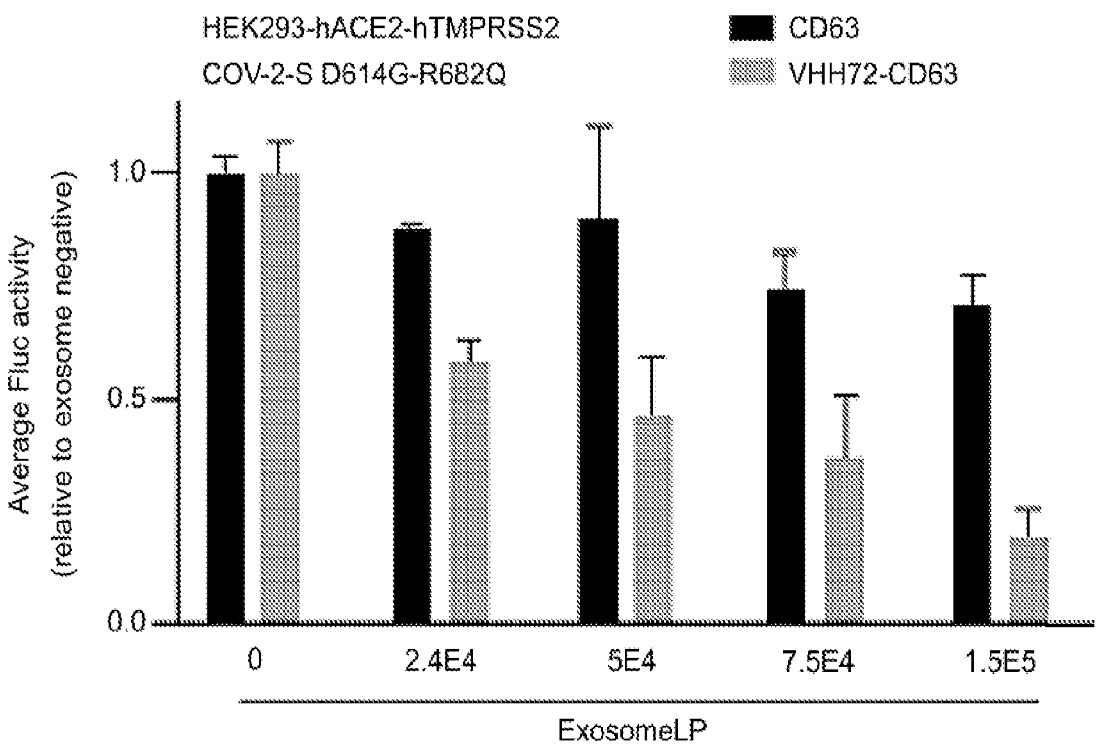
Figure 7:
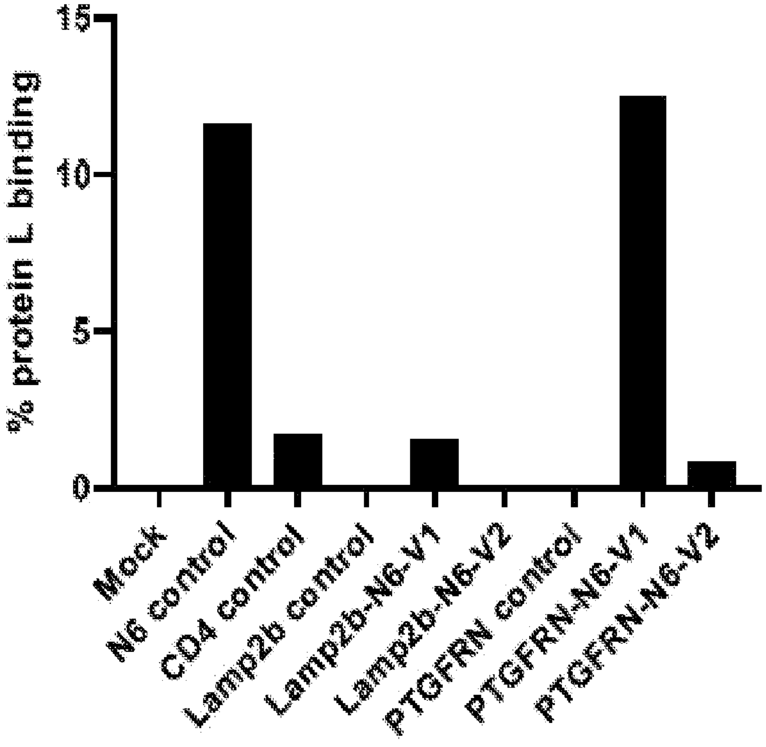
FIG. 7 shows that N6 exosomes can bind L protein beads. Aldehyde/Sulfate latex beads were coated with protein L, which binds scFvs, and used to bind the N6 scFv on the surface of exosomes produced from cells expressing the Lamp2b-N6 and PTGFRN-N6 receptors. An N6 antibody was included as positive binding control, and CD4 protein as a negative control.

To determine the best extracellular loop in CD63 (FIG. 1B) for embedding receptor targeting proteins, the inventors turned to embedding the ScFv of the N6 HIV gp160 receptor targeted broadly neutralizing antibody on the surface of the therapeutic exosomes (FIG. 1A). See Walker et al, Nature, 477(7365):466-470 (2011). To determine the best loop to embed receptor targeting moieties the inventors screened all the available extra-cellular exosome exposed regions for tolerating the N6 broadly neutralizing ScFv (FIG. 1B). See Gobbo et al, Journal of the National Cancer Institute, 108(3) (2016). Notably, the inventors found that one region, Ex2.4 tolerated functional N6, as determined by the binding to gp120 coated beads (FIG. 2) and facilitated exosome uptake and expression of luciferase, from luciferase mRNA EXOtic packaged exosomes in gp120 expressing cells (FIG. 3). These data demonstrate the best locus in CD63 for embedding targeting moieties to redirect exosomes to particular receptor bearing cell types.

The approaches outlined here will be used in multiple ways (both by ex vivo or in vivo manipulation of any cell of interest, e.g. CD4+ T cells, CD8+ T cells, macrophages, liver sinusoidal endothelial cells (LSECs), CD34+ Hematopoietic stem cells (HSCs), CD133+ cells, mesenchymal stem cells (MSCs) are some examples): (1) to deliver exosome packaged drugs to target cells; (2) to deliver RNAs both coding and non-coding to target cells (including regulatory non-coding RNA, like RNAi effectors (e.g., miRNA)); (3) to deliver CRISPR/gRNA complexes to target cells; and (4) to deliver recombinant gene editing protein modalities (Zinc Finger Nucleases) to specific receptor targeted cells. These approaches could also be used with lentiviral vectors to transduce particular cell types in vivo or ex vivo and converting a particular cell type, tissue or organ into a receptor-targeted exosome producing machine.

Example 2

The inventors will develop and test SARS-CoV-2 cell-specific receptor targeted exosomes. A highly innovative receptor targeted exosome approach will be developed that incorporates a SARS-CoV-2 spike S protein specific single-chain fragment variable into the exosome to enhance exosome targeting of those cells infected with SARS-CoV-2. The specificity of this SARS-CoV-2 spike S protein directed exosome approach for targeting infected cells and neutralizing virus infectivity will be determined.

Development of SARS-CoV-2 specific cell targeted exosomes. SARS-CoV-2 appears to infect cells by interactions of spike and envelope with ACE2. Being able to direct exosomes to those cells that are infected with SARS-CoV-2 would be advantageous in increased specificity of targeting the virus and at the same time reducing off-target side-effects. As discussed in Example 1, the Ex2.4 locus in CD63 is a good location for inserting various targeting ligands or ScFv fusions.

The incorporation of the SARS-CoV-2 S protein spike targeted ScFv (Huang et al, Immunity. 2016; 45(5):1108-21) into the Ex2.4 locus of CD63 will be developed and tested. The ScFv will be embedded into the Ex2.4 locus in CD63 (FIG. 1B). The resultant spike targeted ScFv containing CD63 fusions will be used with Nanoluc or mCherry and the EXOtic system, as described in Reshke et al, Nat Biomed Eng. 2020; 4(1):52-68, to develop Nanoluc or mCherry packaged exosomes from 293HEK cells. The collected exosomes will be analyzed using the nanoparticle tracking analysis, dynamic light scattering, and transmission electron Microscopy (TEM). The exosome markers will also be determined by western blot. Collectively these assays will allow for the quantification of exosome particles. Next, the resultant exosomes will be exposed, in varying concentrations (ranging from 0 exosomes/cell to 3.0×10^5 exosomes per cell) to cultured VERO cells containing the psi-check 2.1 system, as a proxy to measure siRNA repression of the targeted 5' UTR or the essential protein M, with and without SARS-CoV-2 S protein spike expression, as described in Adedeji et al, J Virol. 2013; 87(14):8017-28. The exosome exposed cells will be assessed for luciferase expression. These studies should allow for the specificity of CD63-Spike to target S protein Spike expressing cells relative to non-targeted exosomes to be determined.

Screening of SARS-CoV-2 specific cell targeted exosomes. The top-candidate SARS-CoV-2 targeted exosomes, both containing the spike protein targeted ScFv and control non-spike containing exosomes will be screened for their ability to repress virus expression. The various RNAi and ScFv containing and control non-ScFv containing exosomes will be exposed, in varying concentrations (ranging from 0 exosomes/cell to 3.0×10^5 exosomes/cell, based on previous studies), to cultured SARS-CoV-2 infected A549 lung epithelial and VERO cells in vitro. The exosome exposed cells will be assessed for virus expression by digital droplet qRT-PCR. These studies will allow for the specificity, efficacy, and relative dosage of CD63-ScFv relative to control exosomes to target and inhibit SARS-CoV-2 virus expression in virus infected cells.

The effects of ScFv containing exosomes on cellular transcriptomic programs. Binding and internalization of the anti-SARS-CoV-2 exosomes in virus infected and control cells as well as the expression of anti-SARS-CoV-2 siRNAs in human cells may have confounding effects on cellular transcriptional networks. For instance it is known that engaging the SARS-CoV-2 targeted ACE2 receptor can induce internal cellular changes, including in the transcriptomic program of the cell (Kamel et al, Mol Neurobiol. 2018; 55(10):8188-202). To determine those transcriptional changes in target cells the various exosome formulations (both the ScFv fusion containing exosomes or CD63 (Control) exosomes with and without the anti-SARS-CoV-2 siRNAs) will be exposed to SARS-CoV-2 spike expressing and null cells. The cells will be treated with the various exosomes and aliquots of these cells will be characterized at 30 min, 1, 4, 8, and 24 hrs post-exosome treatment for changes in transcriptome expression by RNA high-throughput deep sequencing of the isolated exosomes and RNA from the treated cultures. The resulting cellular RNAs will be mapped to the genome and differential expression in the various treated and control cultures determined using the Tophat-Cufflinks pipelines, as described by Hewson et al, Noncoding RNA Res. 2016; 1(1):3-11; and Trakman et al, PloS one. 2016; 11(4):e0152424. Collectively, these studies will identify to what extent the CD63-ScFv, control exosomes, and SARS-CoV-2 spike expression induces various transcriptional networks in human kidney cell as well as Vero cells.

These experiments will demonstrate that exosomes can be generated to specifically target those cells expressing S protein spike from SARS-CoV-2 and SARS-CoV-2 infected cells and that these spike targeted ScFv containing exosomes will transcriptionally alter the target cell.

In vivo characterization of SARS-CoV-2 targeted exosomes. To confirm the efficacy of the exosome approach outlined herein in vivo, the inventors we will develop a lentiviral vector that expresses the SARS-CoV-2 spike as well as a luciferase psi-check transgene system which contains both the SARS-CoV-2 target sites (e.g., 5' UTR and protein M) as well as the SARS-CoV-2 spike; described by Weinberg et al, Nucleic acids research. 2007; 35(21):7303-12. This vector, and control vectors, which contain the SARS-CoV-2 5' UTR and protein M target sequences in reverse orientation, will be used to infect K18-hACE2 mice, as described in McCray et al, J Virol. 2007; 81(2):813-21. and the ability to target these cells and repress luciferase by each SARS-CoV-2 directed siRNA containing exosomes will be determined. Specifically, after viable infection of the K18-hACE2 mice with the SARS-CoV-2-luciferase virus the infected mice will be treated with the anti-SARS-CoV-2 containing exosomes or control exosomes, containing a scrambled siRNA or scrambled polycistronic siRNAs. The exosomes will be administered intranasally, intravenously or intraperitoneally (80 billion exosomes/mouse) weekly and the animals monitored for luciferin expression from live animal imaging. After 3 weeks the animals will be euthanized and the expression of SARS-CoV luciferase fusion transcript expression and detection of the anti-SARS-CoV-2 siRNAs will be determined in the tumor by qRT-PCR.

These in vivo studies will demonstrate that anti-SARS-CoV-2 exosomes can be administered systemically to repress virus expression.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An exosome comprising a recombinant fusion protein, wherein the recombinant fusion protein comprises an exosome membrane-associated protein and an exogenous target protein; wherein (i) the exosome membrane-associated protein is CD63, and (ii) the recombinant fusion protein comprises the exogenous target protein within extracellular loop 2.4 of CD63; wherein extracellular loop 2.4 of CD63 has an amino acid sequence that is at least 90% identical to SEQ ID NO:17.

2. The exosome of claim 1, wherein the exogenous target protein is a N6 single chain variable fragment.

3. The exosome of claim 1, wherein the exogenous target protein is N6 single chain variable fragment, CR3022 single chain variable fragment, CCR4 single chain variable fragment, CCL17 single chain variable fragment, or VHH-72 heavy chain variable fragment.

4. The exosome of claim 1, wherein the exogenous target protein is an RNA binding protein; wherein the RNA binding protein is L7ae, L30e, RBM5, RBM6, RBM7, RMB22, RMB32, RBM41, YBX1, YBX2, CSDE1, PTBP1, ZC3H3, ZC3H15, MATR3, SAMD4A, YTHDC2, CUGBP2, PUM2, RC3H2, ZC3H11A, PARP12, CSDA, SFRS8, EIF4B, U2AF2, SFRS14, SPEN, ELVAL1, THUMPD1, DHX8, SRBD1, PABPC1, DAZAP1, IFG2PB2, ZNF638, SART3, MKRN2, MBNL3, SNRPA, SYNJ2, A2BP1, DDX43, KIAA0020, CNOT4, YTHDC1, PPIE, CHERP, KHSRP, or FUS.

5. A pharmaceutical composition comprising the exosome of claim 1 and a pharmaceutically acceptable excipient.

6. A cell comprising the exosome of claim 1, wherein the cell is a CD4+ T cell, CD8+ T cell, macrophage, liver sinusoidal endothelial cell, CD34+ hematopoietic stem cell, CD133+ cell, or a stem cell.

7. The exosome of claim 1, wherein extracellular loop 2.4 of CD63 has an amino acid sequence of SEQ ID NO:17.

8. The exosome of claim 2, wherein the N6 single chain variable fragment comprises a heavy chain variable fragment having at least 95% sequence identity to the amino acid sequence of SEQ ID NO:20 and a light chain variable fragment having at least 95% sequence identity to the amino acid sequence of SEQ ID NO:21.

9. The exosome of claim 8, wherein the N6 single chain variable fragment comprises a heavy chain variable fragment having SEQ ID NO:20 and a light chain variable fragment having SEQ ID NO:21.

10. The exosome of claim 1, wherein the exogenous target protein is ACE2 peptide, wherein the ACE2 peptide comprises SEQ ID NO:30.

11. The exosome of claim 1, wherein the exogenous target protein is an ACE2 peptide, CCL22, D1D2 domain of CD4, CD4 transmembrane domain, MIP-1-α, SDF-1, or IL-8.

12. The exosome of claim 1, wherein the exogenous target protein is (i) D1D2 domain of CD4, wherein D1D2 domain of CD4 has at least 95% sequence identity to the amino acid sequence of SEQ ID NO:22, or (ii) CD4 transmembrane domain, wherein CD4 transmembrane domain has SEQ ID NO: 23.

13. The exosome of claim 1, wherein the exogenous target protein is CCR4 single chain variable fragment, wherein the CCR4 single chain variable fragment comprises a heavy chain variable fragment having at least 95% sequence identity to the amino acid sequence of SEQ ID NO: 27 and a light chain variable fragment having at least 95% sequence identity to the amino acid sequence of SEQ ID NO:26.

14. The exosome of claim 1, wherein the exogenous target protein is CR3022 single chain variable fragment, wherein the CR3022 single chain variable fragment comprises a heavy chain variable fragment having at least 95% sequence identity to the amino acid sequence of SEQ ID NO: 29 and a light chain variable fragment having at least 95% sequence identity to the amino acid sequence of SEQ ID NO:28.

15. The exosome of claim 1, wherein the exogenous target protein is VHH-72 heavy chain variable fragment, wherein VHH-72 heavy chain variable fragment has at least 95% sequence identity to the amino acid sequence of SEQ ID NO:29.

16. The exosome of claim 1, wherein the exogenous target protein is:

(i) CCR4 single chain variable fragment, wherein the CCR4 single chain variable fragment comprises a heavy chain variable fragment having SEQ ID NO:27 and a light chain variable fragment having SEQ ID NO:26;

(ii) CR3022 single chain variable fragment, wherein the CR3022 single chain variable fragment comprises a heavy chain variable fragment having SEQ ID NO:29 and a light chain variable fragment having SEQ ID NO:28; or (iii) VHH-72 heavy chain variable fragment, wherein VHH-72 heavy chain variable fragment has SEQ ID NO:29.

17. The exosome of claim 1, wherein the recombinant fusion protein comprises an amino acid sequence having at least 90% sequence identity to the amino acid sequence of SEQ ID NO: 4.

18. The exosome of claim 1, wherein the recombinant fusion protein comprises an amino acid sequence having at least 90% sequence identity to the amino acid sequence of SEQ ID NO: 10, SEQ ID NO:11, SEQ ID NO: 12, or SEQ ID NO: 13.

* * * * *